United States Patent
Kalnik et al.

(10) Patent No.: US 12,318,433 B2
(45) Date of Patent: Jun. 3, 2025

(54) NICOTINE DEGRADING ENZYME VARIANTS

(71) Applicant: ANTIDOTE THERAPEUTICS, INC., Bethesda, MD (US)

(72) Inventors: Matthew W. Kalnik, Bethesda, MD (US); Thomas Thisted, New Market, MD (US); Charles C. Reed, Souderton, PA (US)

(73) Assignee: ANTIDOTE THERAPEUTICS, INC., Bethesda, MD (US)

( * ) Notice: Subject to any disclaimer, the term of this patent is extended or adjusted under 35 U.S.C. 154(b) by 1071 days.

(21) Appl. No.: 17/265,169

(22) PCT Filed: Jul. 2, 2019

(86) PCT No.: PCT/US2019/040345
§ 371 (c)(1),
(2) Date: Feb. 1, 2021

(87) PCT Pub. No.: WO2020/027970
PCT Pub. Date: Feb. 6, 2020

(65) Prior Publication Data
US 2022/0031814 A1    Feb. 3, 2022

Related U.S. Application Data

(60) Provisional application No. 62/713,814, filed on Aug. 2, 2018.

(51) Int. Cl.
*A61K 38/44* (2006.01)
*A61P 25/34* (2006.01)
*C12N 9/06* (2006.01)

(52) U.S. Cl.
CPC .............. *A61K 38/44* (2013.01); *A61P 25/34* (2018.01); *C12N 9/0022* (2013.01)

(58) Field of Classification Search
None
See application file for complete search history.

(56) References Cited

U.S. PATENT DOCUMENTS

| | | |
|---|---|---|
| 11,279,916 B2 | 3/2022 | Xu et al. |
| 11,597,916 B2 | 3/2023 | Kalnik et al. |
| 2019/0153403 A1 | 5/2019 | Xu et al. |
| 2020/0224176 A1 | 7/2020 | Kalnik et al. |
| 2022/0031814 A1 | 2/2022 | Kalnik et al. |

FOREIGN PATENT DOCUMENTS

| | | |
|---|---|---|
| WO | WO-2017/023904 A2 | 2/2017 |
| WO | WO-2017/167250 A1 | 10/2017 |
| WO | WO-2018/144879 A1 | 8/2018 |
| WO | WO-2019/126364 A2 | 6/2019 |
| WO | WO-2020/027970 A1 | 2/2020 |

OTHER PUBLICATIONS

Qiu et al., "Cloning of a Novel Nicotine Oxidase Gene from *Pseudomonas* sp. Strain HZN6 Whose Product Nonenantioselectively Degrades Nicotine to Pseudooxynicotine," Applied and Environmental Microbiology, vol. 79, No. 7, 99. 2164-2171 (Apr. 2013).
Tararina et al., "Crystallography Coupled with Kinetic Analysis Provides Mechanistic Underpinnings of a Nicotine-Degrading Enzyme," Biochemistry, vol. 57, No. 26, pp. 3741-3751 (Jul. 2018).
Tararina et al., "Structural Analysis Provides Mechanistic Insight into Nicotine Oxidoreductase from Pseudomonas putida," Biochemistry, vol. 55, pp. 6595-6598 (Nov. 2016).
Thisted et al., "Optimization of a nicotine degrading enzyme for potential use in treatment of nicotine addiction," BMC Biotechnology, vol. 19, No. 56, pp. 1-16 (Aug. 2019).
Xia et al., "Genome-wide investigation of the genes involved in nicotine metabolism in Pseudomonas putida J5 by Tn5 transposon," Appl. Microbiol. Biotechnol., vol. 99, pp. 6503-6514 (Mar. 2015).
Xue et al., "A New Strategy for Smoking Cessation: Characterization of a Bacterial Enzyme for the Degradation of Nicotine," J. Am. Chem. Soc., vol. 137, pp. 10136-10139 (Aug. 2015).

*Primary Examiner* — Michelle F. Paguio Frising
*Assistant Examiner* — Grant C Currens
(74) *Attorney, Agent, or Firm* — Foley & Lardner LLP

(57) ABSTRACT

Described are nicotine-degrading enzyme variants that exhibit increased nicotine-degrading activity and/or decreased immunogenicity relative to the wild-type NicA2 enzyme, compositions comprising the variants, and methods using them.

27 Claims, 21 Drawing Sheets

Specification includes a Sequence Listing.

FIG 4A

Relative Activities of Epitope 1 Variants

(Bar chart with y-axis 0–9000, x-axis categories: I262A, A264Q; I262K, L266D; I262T; I262S; I262D, L266K; I262A; I262T, A264L; I262T, N263R; M265H; I262A, A264N; wt)

FIG 4B

Relative Activities of Epitope 2 Variants

(Bar chart with y-axis 0–9000, x-axis categories: V303T, V304N, M306I; V304A, M306Q; V304A, M306N; V304A; V304A, M306H; V304N, M306H; V304Q, M306H; V304N, M306I; V304T, M306I; M306I, L310R; wt)

FIG 4E

Relative Activities of Epitope B Variants

Variants (left to right): L74N, Y77R; L74N, Y77K; L74Q, Y77R; L74Q, Y77N; L74N, Y77Q; L74N, Y77H; L74N, L80H; L80F; Y77R; R78Q; wt Enzyme Activity in Serum Monitored by GC

NICOTINE DEGRADING ENZYME VARIANTS

RELATED APPLICATION

This application is the U.S. National Stage of International Application No. PCT/US2019/040345, and claims priority under 35 U.S.C. § 119(e) to U.S. Provisional Application 62/713,814 filed Aug. 2, 2018, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Nov. 14, 2019, is named 105894-0114_SL.txt and is 136,278 bytes in size.

FIELD

The present disclosure relates generally to the field of treating nicotine addiction or nicotine poisoning. Described are nicotine-degrading enzyme variants that exhibit increased nicotine-degrading activity and/or decreased immunogenicity relative to the wild-type NicA2 enzyme, compositions comprising them, and methods using them.

BACKGROUND

The following discussion is provided to aid the reader in understanding the disclosure and is not admitted to describe or constitute prior art thereto.

Smoking is a global healthcare problem. The World Health Organization estimates that there are 1.3 billion smokers worldwide today and nearly five million tobacco-related deaths each year. If current smoking patterns continue, smoking will cause some 10 million deaths each year by 2020. According to the U.S. Center for Disease Control (CDC), tobacco use is the single leading preventable cause of death in the U.S., responsible for approximately 438,000 deaths each year. In addition, it is estimated that smoking results in an annual health-related economic cost of approximately $157 billion. The CDC estimates that, among the 45 million adult smokers in the U.S., 70% want to quit, but less than five percent of those who try to quit remain smoke-free after 12 months.

One reason it is difficult to quit smoking is addiction to the nicotine in cigarettes and other tobacco products. Nicotine is a small molecule that upon inhalation into the body quickly passes into the bloodstream and subsequently reaches the brain by crossing the blood-brain barrier. Once in the brain, the nicotine binds to nicotinic receptors, which results in the release of stimulants, such as dopamine, activating the reward system and providing the smoker with a positive and pleasurable re-enforcing experience, which leads to addiction.

In addition to the detrimental health effects associated with smoking and other tobacco use, nicotine poisoning, which results from ingestion or inhalation of too much nicotine, is another nicotine-related health problem. The $LD_{50}$ of nicotine is 50 mg/kg for rats and 3 mg/kg for mice. A dose as low as 30-60 mg (0.5-1.0 mg/kg) may be lethal for adult humans, while children may become ill following ingestion of one cigarette, and ingestion of more than this may cause a child to become severely ill. On the other hand, some evidence suggests that a lethal dose may be as high as 500 mg or more (1.0-7.1 mg/kg) for a human adult. In either case, acute nicotine poisoning usually occurs in children who accidentally chew on nicotine gum or patches or ingest the "e-liquid" of electronic cigarettes. In rare instances, children have also been known to become ill after ingesting cigarettes. There are several hundred cases of acute nicotine poisoning reported every month in the United States alone.

Typically, initial treatment of nicotine poisoning may include the administration of activated charcoal to try to reduce gastrointestinal absorption, while additional treatment may address the symptoms that result from nicotine poisoning.

The use of the wild-type NicA2 enzyme for smoking cessation has been proposed (see, e.g., Xue et al., *J. Am. Chem. Soc.* 137: 10136-39 (2015)). Nevertheless, there remains a need for additional agents, compositions and methods for treating nicotine addiction, as well as for agents, compositions, and methods for treating nicotine poisoning.

SUMMARY

Described herein are nicotine-degrading enzyme variants that exhibit increased nicotine-degrading activity and/or decreased immunogenicity relative to the wild-type NicA2 enzyme, compositions comprising them, and methods using them.

In some embodiments, the nicotine-degrading enzyme variant comprises an amino acid sequence that is a variant of the amino acid sequence of the wild-type NicA2 enzyme set forth in SEQ ID NO: 1, wherein the variant sequence has at least one substitution, addition, or deletion at one or more of positions 104, 106, 107, 249, 355, and 426 of SEQ ID NO: 1 that increases the nicotine-degrading activity.

In some embodiments, the variant exhibits increased nicotine-degrading activity relative to the wild-type NicA2 enzyme. In some embodiments, the variant of the wild-type NicA2 sequence comprises one or more of the substitutions F104R, F104K, F104I, F104L, F104S, F104T, G106S, G106A, A107T, A107G, A107H, A107P, E249W, E249D, F355H, F355K, F355E, A426Q, A426W, A426P, or A426C. In some embodiments, the variant sequence comprises an amino acid sequence selected from any one of SEQ ID NOs: 5-12 or 15-28. In preferred embodiments, the variant may comprise one or more of an F104R substitution, an F104I substitution, an F104S substitution, an F104T substitution, a G106A substitution, an A107T substitution, an A107G substitution, an F355H substitution, or an A426C substitution. In some embodiments, the nicotine-degrading activity of the variant is at least about 200%, at least about 300%, at least about 400%, at least about 500%, at least about 600%, at least about 700%, at least about 800%, at least about 900%, or at least about 1000% of the nicotine-degrading activity of the wild-type NicA2 enzyme. In some embodiments, the variant sequence comprises substitutions at least one, at least two, or at least three positions selected from position 104, 106, 107, 249, 355, and 426 of SEQ ID NO:1. In some embodiments, the variant may have a deletion of 1-52 amino acids at the N-terminus of the peptide. For example, a variant derived from SEQ ID NO:1 may comprise a deletion of 5, 10, 15, 20, 25, 30, 35, 40, 45, 50, 51, or 52 amino acids from the N-terminus of the peptide. In some embodiments, the variant additionally or alternatively may have a deletion of 1 or more amino acids from the C-terminus of the peptide, such as a deletion of the C-terminal residue. In some embodiments, the variant may further comprise a conservative substitution, non-conservative substitution, addition, or deletion at one or more of positions 91, 217, 250, 340, 366, 381, 427, 462, or 463 of SEQ ID NO:1. In some embodiments, the variant may further comprise one or more substitutions selected from F104L, G106S, A107H, A107P, A107R, A107K, A107T, F355C, F355V, W427Q, W427E, W427S, W427M, W427H, W427L, W427R, R91A, R91Q, R91F, R91G, R91T, R91L, R91S, R91N, T250G, T250L, T250R, T250V, T250P, K340P, K340I, K340V, K340D, K340E, Q366K, Q366E, Q366V, Q366L, Q366I, Q366Y, T381P, T381I, T381V, T381Q, T381N, T381L, T381M, N462L, N462Y, N462S, N462F, N462G, N462E, N462A, N462M, I463F, I463Y, I463A, I463V, I463L, L217Q, L217G, L217E, L217I, L217C, and L217S.

In some embodiments, the NicA2 variant additionally exhibits reduced immunogenicity relative to the wild-type NicA2 enzyme. In some embodiments, the immunogenicity relative to the wild-type NicA2 enzyme is reduced by 75% or more. In some embodiments, the variant sequence further comprises at least one substitution, addition, or deletion in an immunogenic T-cell epitope within a region selected from amino acids 10-32, 68-94, 189-225, 248-285, 296-327, 336-391, or 435-459 of SEQ ID NO: 1. In some embodiments, the variant sequence further comprises at least one substitution, addition, or deletion in an immunogenic T-cell epitope selected from amino acids 16-24, 73-81, 258-266, 302-310, 373-381, or 447-455 of SEQ ID NO: 1. In some embodiments, the variant sequence further comprises at least one substitution, addition, or deletion at a position selected from (a) amino acid residues 74, 77, 78, or 80 of SEQ ID NO: 1; (b) amino acid residues 262, 263, 264, or 266 of SEQ ID NO: 1; (c) amino acid residues 303, 304, 306, or 310 of SEQ ID NO: 1; (d) amino acid residues 374, 377, 378, 382, or 383 of SEQ ID NO: 1; and/or (e) amino acid residues 450, 451, 452, or 457 of SEQ ID NO: 1. In some embodiments, the variant sequence further comprises at least one substitution or substitution combination selected from those listed for Epitope B in Table 2. Additionally or alternatively, in some embodiments, the variant sequence further comprises at least one substitution or substitution combination selected from those listed for Epitope 1 in Table 2. Additionally or alternatively, in some embodiments, the variant sequence further comprises at least one substitution or substitution combination selected from those listed for Epitope 2 in Table 2. Additionally or alternatively, in some embodiments, the variant sequence further comprises at least one substitution or substitution combination selected from those listed for Epitope 3 in Table 2. Additionally or alternatively, in some embodiments, the variant sequence further comprises at least one substitution or substitution combination selected from those listed for Epitope 4 in Table 2. In some embodiments, the variant further comprises at least one substitution or substitution combination selected from (a) I262T; (b) I262S; (c) I262A; (d) I262T and A264L; and/or (e) I262T and N263R.

Additionally or alternatively, in some embodiments, the variant further comprises a deletion of at least amino acids 1-38 of SEQ ID NO: 1, or of amino acids 1-50 of SEQ ID NO: 1, or amino acids 1-51 of SEQ ID NO: 1, or amino acids 1-52 of SEQ ID NO: 1. In some embodiments, the variant may further comprises a His-tag, such as a His-tag comprising the amino acid sequence of SEQ ID NO: 32. Additionally or alternatively, in some embodiments, the variant comprises a deletion of one or more C-terminal amino acids, such as a deletion of the residue corresponding to S482 of the wild-type sequence. In any of the embodiments, the variant may be a long-acting variant, such as wherein the variant is conjugated to an albumin-binding peptide, an albumin-binding protein domain, human serum albumin, or an inert polypeptide, such as recombinant PEG (XTEN®), a homo-amino acid polymer (HAP), a proline-alanine serine polymer (PAS), or an elastin-like peptide (ELP). In specific embodiments, the long-acting variant is conjugated to polyethylene glycol (i.e., the variant is PEGylated).

Additionally or alternatively, in some embodiments, the variant may further comprise one or more mutations (e.g., 1, 2, 3, 4, 5, 6, 7, 8, 9, or 10) selected from the group consisting of F163A, Y214A, Y218A, Y242A, M246A, E249A, F353V, F355V, W364V, F353A, F355A, and W364A. In another aspect, the present disclosure provides nicotine-degrading enzyme variants comprising an amino acid sequence that is a variant of the amino acid sequence of the wild-type NicA2 enzyme set forth in SEQ ID NO: 1, wherein the variant sequence has at least one substitution selected from the group consisting of F163A, Y214A, Y218A, Y242A, M246A, E249A, F353V, F355V, W364V, F353A, F355A, and W364A, and comprises an N-terminal deletion of 1-52 amino acids. In some embodiments, the N-terminal deletion may be, for example, 25, 38, or 50 amino acids.

In some embodiments, there are provided pharmaceutical compositions comprising a nicotine-degrading enzyme variant described herein and a pharmaceutically acceptable carrier. In some embodiments, the composition is formulated for injection or infusion. In some embodiments the composition is formulated for oral administration.

In some embodiments, there are provided methods of treating nicotine addiction or facilitating smoking cessation, comprising administering to a mammalian subject in need thereof a therapeutically effective amount of a nicotine-degrading enzyme variant or composition as described herein. In some embodiments, the mammalian subject is a human subject. In some embodiments, the nicotine addiction is associated with the ingestion of a nicotine product selected from tobacco products and electronic cigarettes.

In some embodiments, there are provided methods of treating nicotine poisoning, comprising administering to a mammalian subject in need thereof a therapeutically effective amount of a nicotine-degrading enzyme variant or composition as described herein. In some embodiments, the mammalian subject is a human subject, or, more specifically, a human child. In some embodiments, the nicotine poisoning is associated with the consumption of a nicotine product selected from tobacco products and electronic cigarettes.

Also provided are nicotine-degrading enzyme variants and compositions as described herein for use in treating nicotine addiction or facilitating smoking cessation.

Also provided are uses of nicotine-degrading enzyme variants and compositions as described herein in the manufacture of a medicament for the treatment of nicotine addiction or facilitation of smoking cessation.

The foregoing general description and following detailed description are exemplary and explanatory and are intended to provide further explanation of the invention.

BRIEF DESCRIPTION OF THE DRAWINGS

FIG. 1 shows SDS-PAGE analysis of His-tagged versions of wild-type NicA2 (SEQ ID NO:1) and NicA2A50 (SEQ ID NO:2). Lane 1: MW marker (Blue Plus2; Invitrogen); Lane 2: wild-type NicA2 (SEQ ID NO:1); and Lane 3: NicA2A50 (SEQ ID NO:2).

FIG. 2 shows results of a nicotine-degrading activity assay comparing wild-type NicA2 with variant nicotine-degrading enzymes as described herein. The assays used purified proteins at a final concentration of 80 nM.

FIG. 3 shows the residues around the active site in the NicA2 crystal structure (adapted from Tararina et al., *Biochem.* 55:6595-98 (2016)). Shell one is shown in dark grey and shell two is shown in light grey. The residues making up the first and second shell are shown in Table 2.

FIGS. 4A-E show the relative activities of specific NicA2 variants carrying mutations of Epitopes B (FIG. 4E), 1 (FIG. 4A), 2 (FIG. 4B), 3 (FIG. 4C) and 4 (FIG. 4D) (as listed in Table 2), predicted to reduce the immunogenic potential compared to wild-type NicA2.

Figure 8:
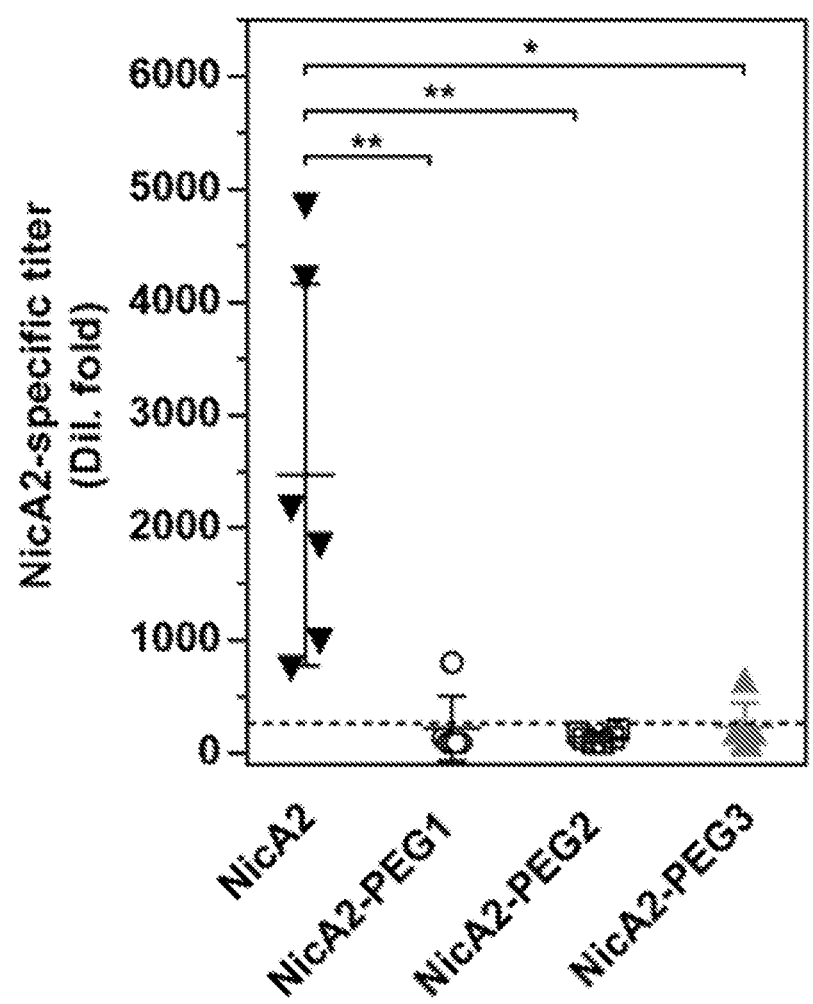

FIG. 8 shows PEGylation can decrease titers of NicA2-specific antibodies in a transgenic HLA-DR4 mouse model of immunogenicity. PEGylation of NicA2 led to a significant (≥10-fold) decrease in average NicA2-specific antibody titers in transgenic DR4 mice (4, 2, and 2, animals from groups NicA2-PEG1, -PEG2, and -PEG3, respectively, had titers below the limit of detection (LOD)), suggesting a lower immunogenic potential in a clinical setting. *=$p<0.01$, =$p<0.001$ and *=$p<0.0001$.

Figure 9:
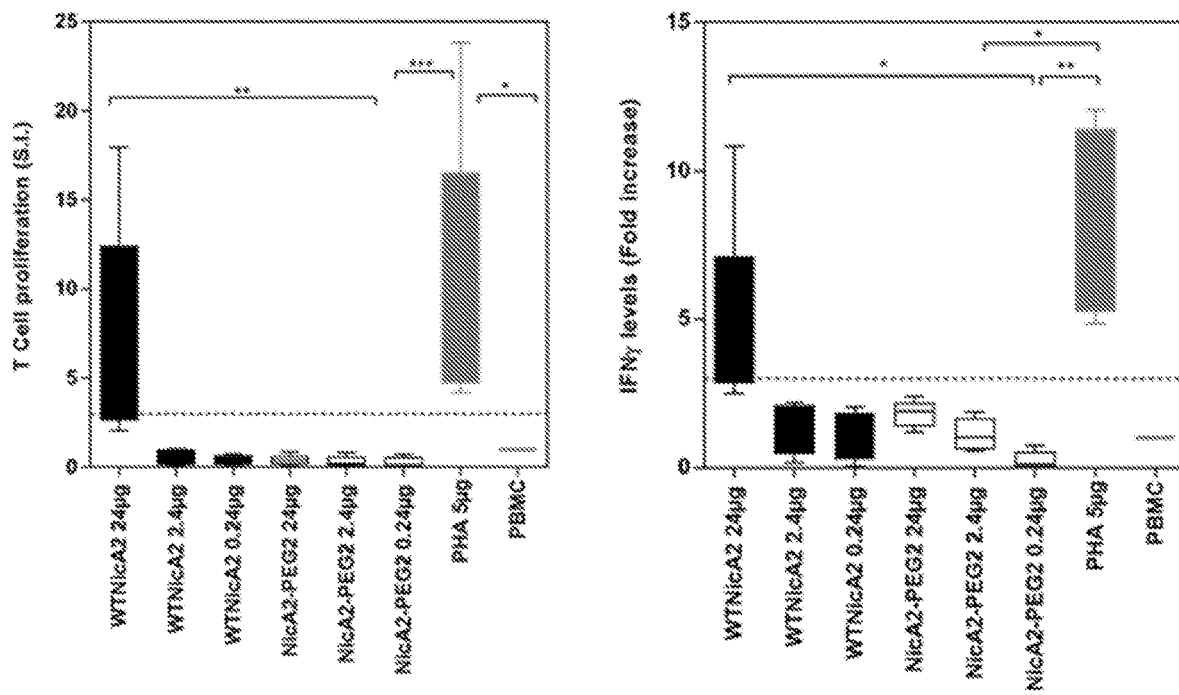
Figure 10:
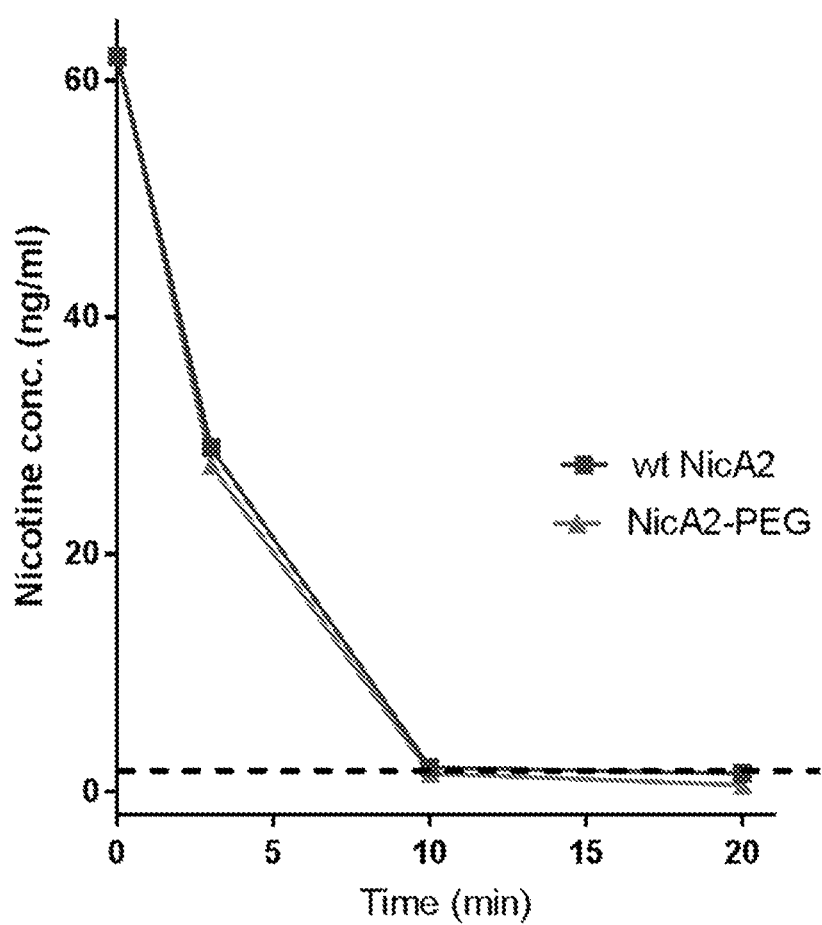
Figure 11A:
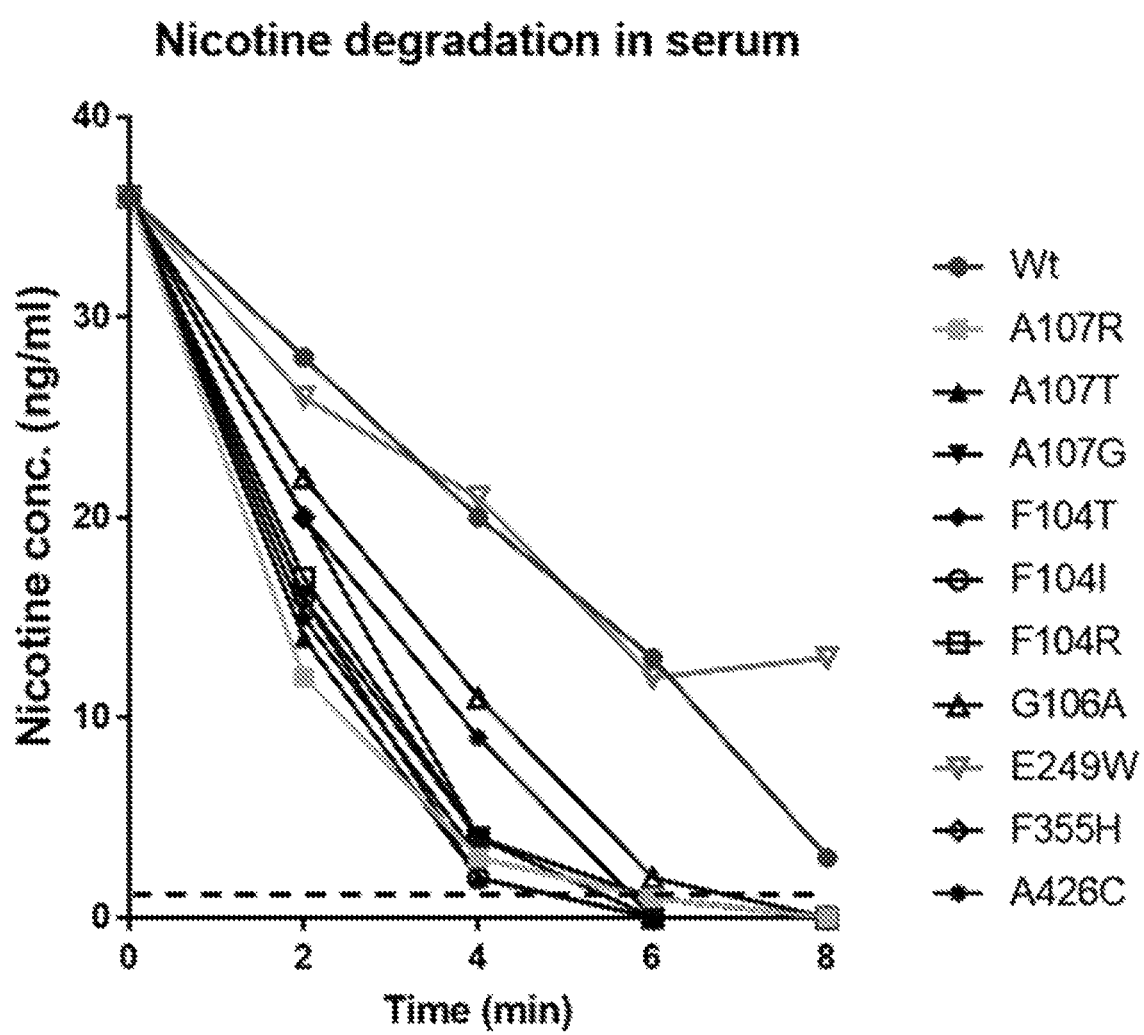
Figure 11B:
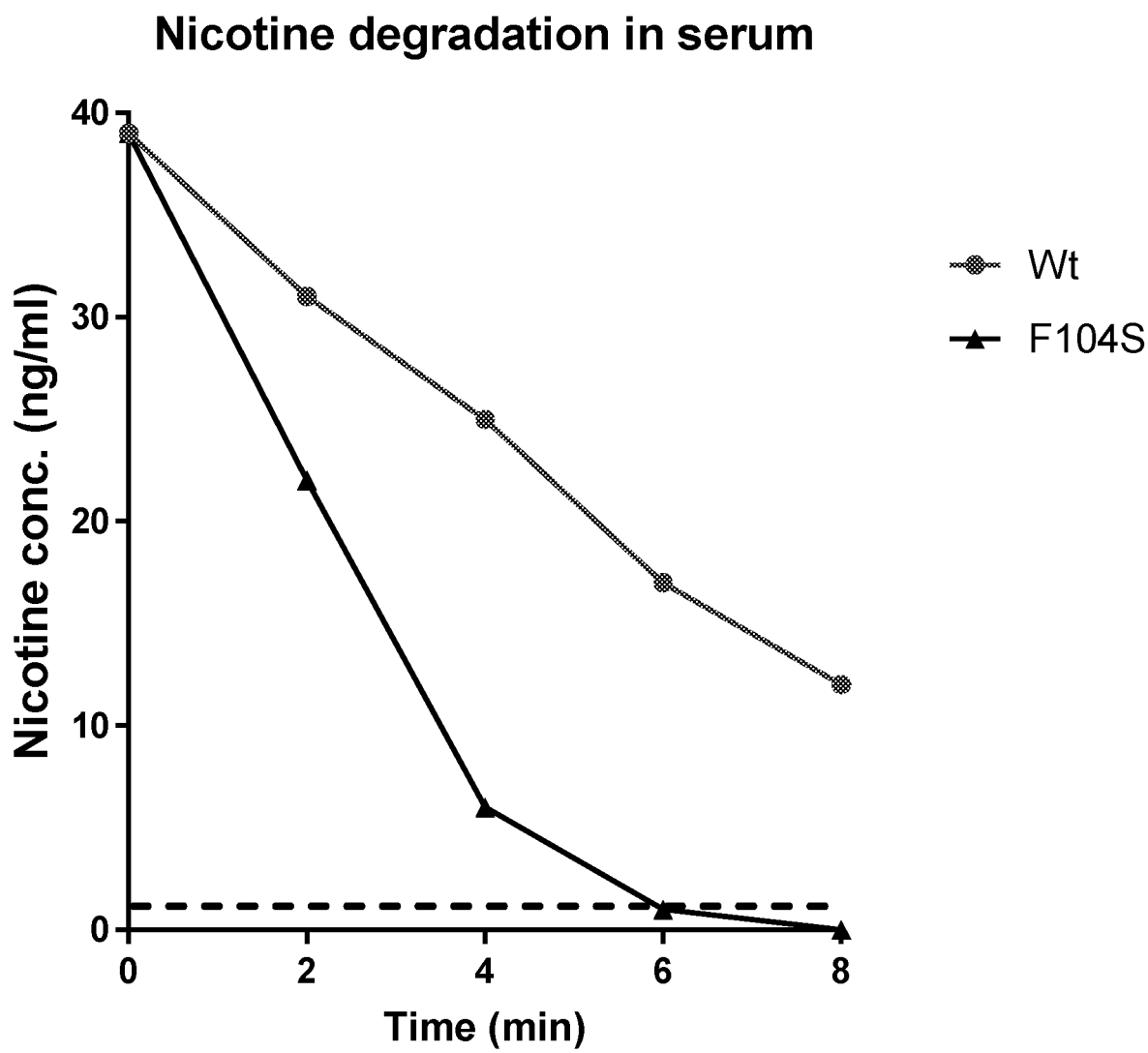

FIG. 9 shows PEGylation attenuates the human T-cell proliferation response and cytokine TNFγ release mediated by exposure to NicA2. PEGylation of NicA2 led to a significant decrease in average T Cell proliferation Stimulation Index (left panel) as well as a decrease in IFNγ secretion levels (right panel). An increase of 3≥ (dashed line) is considered a significant increase and a positive response. *=$ The terms "treatment" or "treating" as used herein with reference to nicotine addiction or smoking cessation refer to one or more of: reducing, ameliorating or eliminating one or more symptoms or effects of nicotine withdrawal; reducing the number of cigarettes or the amount of nicotine consumed by a subject; and/or reducing the subject's plasma levels of nicotine and/or reducing the amount of nicotine localized in specific tissues of the subject (e.g., brain/central nervous system, heart and vasculature, etc.).

The terms "treatment" or "treating" as used herein with reference to nicotine poisoning refer to reducing, ameliorating or eliminating one or more symptoms or effects of nicotine and/or reducing the subject's plasma levels of nicotine and/or reducing the amount of nicotine localized in specific tissues of the subject (e.g., brain/central nervous system, heart and vasculature, etc.).

The terms "individual," "subject," and "patient" are used interchangeably herein, and refer to any individual mammal subject, e.g., bovine, canine, feline, equine, or human.

In accordance with FDA guidance, as used herein, "child" refers to a human subject from 0 through about 19 years of age. A child can be a subject that begins a course of treatment prior to turning about 19 years of age, even if the subject continues treatment beyond 19 years of age.

II. Nicotine, Nicotine Addiction, and Nicotine Toxicity

Nicotine is a nitrogen-containing chemical made by several types of plants including tobacco and other members of the nightshade family. When humans, mammals and most other types of animals are exposed to nicotine, it increases their heart rate, heart muscle oxygen consumption rate, and heart stroke volume. The consumption of nicotine is also linked to raised alertness, euphoria, and a sensation of being relaxed. However, nicotine is highly addictive.

By binding to nicotinic acetylcholine receptors in the brain, nicotine elicits its psychoactive effects and increases the levels of several neurotransmitters in various brain structures. Nicotine has a higher affinity for nicotinic receptors in the brain than those in skeletal muscle, though at toxic doses it can induce contractions and respiratory paralysis. Nicotine's selectivity is thought to be due to a particular amino acid difference on these receptor subtypes. The structure of nicotine is shown in Formula I below.

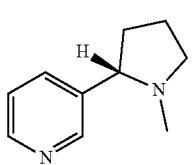

Formula I

People who regularly consume nicotine and then suddenly stop experience withdrawal symptoms, which may include cravings, a sense of emptiness, anxiety, depression, moodiness, irritability, and inattentiveness. The American Heart Association says that nicotine (from smoking tobacco) is one of the hardest substances to quit—at least as hard as heroin.

Nicotine poisoning can occur when an individual consumes loose tobacco, cigarettes, nicotine gum, patches, or the "e-liquid" of electronic cigarettes (e.g., the nicotine-containing liquid that is used in electronic cigarettes and other vaporizing devices) or other products containing tobacco or tobacco extracts, or other products, supplies or intermediates containing nicotine. Indeed, a recent study showed that the incidence of nicotine poisoning from exposure to e-cigarettes increased 1492.9% between January 2012 and April 2015 (Kamboj et al. PEDIATRICS 137(6): e20160041 (2016)). Although exposure can occur through inhalation of tobacco smoke (either primary or second hand), nicotine poisoning or nicotine overdose more commonly results when a subject (typically a child) ingests nicotine, for example by chewing or ingesting nicotine gum, ingesting cigarettes or other tobacco leaf products, ingesting nicotine patches, or ingesting e-liquid. Additionally, nicotine can be dermally absorbed, and therefore nicotine poisoning can result from toxic levels of nicotine coming into direct contact with the skin.

Nicotine poisoning can produce neurological symptoms (convulsions, coma, depression, confusion, fainting, headache), cardiovascular symptoms (rapid heartbeat, high blood pressure), respiratory symptoms (difficulty breathing, rapid breathing), gastrointestinal symptoms (increased salivation, abdominal cramps, vomiting), and musculoskeletal symptoms (Muscular twitching, weakness), as well as death.

III. Nicotine-Degrading Enzyme Variants

Described herein are nicotine-degrading enzyme variants comprising an amino acid sequence that is a variant of the amino acid sequence of the wild-type NicA2 enzyme set forth in SEQ ID NO: 1, wherein the variant sequence has at least one substitution, addition, or deletion relative to SEQ ID NO: 1 that increases the nicotine-degrading activity and/or decreases the immunogenicity of the variant relative to the wild-type NicA2 enzyme.

NicA2 (nicotine oxidoreductase; PPS_4081; GenBank accession number: AEJ14620.1), was isolated from *Pseudomonas putida* strain S16. See, e.g., Tang et al., PLOS GENETICS, 9(10): e1003923 (2013). The activity of NicA2 is the first committed step of S16's degradation of nicotine, catalyzing the oxidation of nicotine to N-methylmyosmine. It is reported to be an essential enzyme in the *P. puida* S16 metabolic cascade responsible for breaking down nicotine. A structural analysis of the wild-type NicA2 enzyme has been reported in Tararina et al., *Biochem.* 55:6595-98 (2016).

The present disclosure provides variants of wild-type NicA2 with improved activity and/or decreased immunogenicity. In some embodiments, the disclosed variants may have an amino acid identity that is about 80, about 85, about 90, about 95, about 96, about 97, about 98, or about 99 percent of wild-type NicA2. In some embodiments, the disclosed variants may share about 80, about 85, about 90, about 95, about 96, about 97, about 98, or about 99 percent homology with wild-type NicA2. For instance, in some embodiments, the disclosed variants may comprise the amino acids residues conserved between NicA2.

The amino acid sequence of wild-type NicA2 and exemplary variants thereof are set forth in Table 1 below. The disclosed variants were produced with a linker and His-tag (GGGGSGSGHHHHHH, SEQ ID NO: 32) at the C-terminal end, which was subsequently removed. The His-tag was used to assist in purification of the variants, but other means or methods of purification that do not require a His-tag may also be used.

TABLE 1

Amino Acid Sequences of NicA2 and Exemplary Variants

| Enzyme | SEQ ID NO. | Sequence |
|---|---|---|
| Wild-Type NicA2 | 1 | M\*SDKTKTNEGFSRRSFIGSAAVVTAGVAGLGAIDAASATQKTNRASTV KGGFDYDVVVVGGGFAGATAARECGLQGYRTLLLEARSRLGGRTFTSR FAGQEIEFGGAWVHWLQPHVWAEMQRYGLGVVEDPLTNLDKTLIMYN DGSVESISPDEFGKNIRIAFEKLCHDAWEVFPRPHEPMFTERARELDKSSV LDRIKTLGLSRLQQAQINSYMALYAGETTDKFGLPGVLKLFACGGWNYD AFMDTETHYRIQGGTIGLINAMLTDSGAEVRMSVPVTAVEQVNGGVKIK TDDDEIITAGVVVMTVPLNTYKHIGFTPALSKGKQRFIKEGQLSKGAKLY VHVKQNLGRVFAFADEQQPLNWVQTHDYSDELGTILSITIARKETIDVN DRDAVTREVQKMFPGVEVLGTAAYDWTADPFSLGAWAAYGVGQLSRL KDLQAAEGRILFAGAETSNGWHANIDGAVESGLRAGREVKQLLS\*\*† |
| NicA2Δ50 (N-terminal deletion of residues 1-50) | 2 | GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2Δ25 (N-terminal deletion of residues 1-25) | 3 | GVAGLGAIDAASATQKTNRASTVKGGFDYDVVVVGGGFAGATAARECG LQGYRTLLLEARSRLGGRTFTSRFAGQEIEFGGAWVHWLQPHVWAEMQ RYGLGVVEDPLTNLDKTLIMYNDGSVESISPDEFGKNIRIAFEKLCHDAW EVFPRPHEPMFTERARELDKSSVLDRIKTLGLSRLQQAQINSYMALYAGE TTDKFGLPGVLKLFACGGWNYDAFMDTETHYRIQGGTIGLINAMLTDSG AEVRMSVPVTAVEQVNGGVKIKTDDDEIITAGVVVMTVPLNTYKHIGFT PALSKGKQRFIKEGQLSKGAKLYVHVKQNLGRVFAFADEQQPLNWVQT HDYSDELGTILSITIARKETIDVNDRDAVTREVQKMFPGVEVLGTAAYDW TADPFSLGAWAAYGVGQLSRLKDLQAAEGRILFAGAETSNGWHANIDG AVESGLRAGREVKQLLS |
| NicA2Δ38 (N-terminal deletion of residues 1-38) | 4 | TQKTNRASTVKGGFDYDVVVVGGGFAGATAARECGLQGYRTLLLEARS RLGGRTFTSRFAGQEIEFGGAWVHWLQPHVWAEMQRYGLGVVEDPLTN LDKTLIMYNDGSVESISPDEFGKNIRIAFEKLCHDAWEVFPRPHEPMFTER ARELDKSSVLDRIKTLGLSRLQQAQINSYMALYAGETTDKFGLPGVLKLF ACGGWNYDAFMDTETHYRIQGGTIGLINAMLTDSGAEVRMSVPVTAVE QVNGGVKIKTDDDEIITAGVVVMTVPLNTYKHIGFTPALSKGKQRFIKEG QLSKGAKLYVHVKQNLGRVFAFADEQQPLNWVQTHDYSDELGTILSITI ARKETIDVNDRDAVTREVQKMFPGVEVLGTAAYDWTADPFSLGAWAA YGVGQLSRLKDLQAAEGRILFAGAETSNGWHANIDGAVESGLRAGREVK QLLS |
| NicA2F104R (F104R substitution) | 5 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIERGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2F104K (F104K substitution) | 6 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEKGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2F104I (F104I substitution) | 7 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEIGGAWVHWLQPHVWAEMQRYGLGVVEDPLTNLDKTLIMYNDGSV ESISPDEFGKNIRIAFEKLCHDAWEVFPRPHEPMFTERARELDKSSVLDRIK TLGLSRLQQAQINSYMALYAGETTDKFGLPGVLKLFACGGWNYDAFMD TETHYRIQGGTIGLINAMLTDSGAEVRMSVPVTAVEQVNGGVKIKTDDD EIITAGVVVMTVPLNTYKHIGFTPALSKGKQRFIKEGQLSKGAKLYVHVK QNLGRVFAFADEQQPLNWVQTHDYSDELGTILSITIARKETIDVNDRDAV |

TABLE 1-continued

Amino Acid Sequences of NicA2 and Exemplary Variants

| Enzyme | SEQ ID NO. | Sequence |
|---|---|---|
| | | TREVQKMFPGVEVLGTAAYDWTADPFSLGAWAAYGVGQLSRLKDLQA<br>AEGRILFAGAETSNGWHANIDGAVESGLRAGREVKQLLS |
| NicA2F104L<br>(F104L<br>substitution) | 8 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIELGGAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2F104S<br>(F104S<br>substitution) | 9 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIESGGAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2F104T<br>(F104T<br>substitution) | 10 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIETGGAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2G106S<br>(G106S<br>substitution) | 11 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGSAWVHWLQPHVWAEMQRYGLGVVEDPLTNLDKTLIMYNDGSV<br>ESISPDEFGKNIRIAFEKLCHDAWEVFPRPHEPMFTERARELDKSSVLDRIK<br>TLGLSRLQQAQINSYMALYAGETTDKFGLPGVLKLFACGGWNYDAFMD<br>TETHYRIQGGTIGLINAMLTDSGAEVRMSVPVTAVEQVNGGVKIKTDDD<br>EIITAGVVVMTVPLNTYKHIGFTPALSKGKQRFIKEGQLSKGAKLYVHVK<br>QNLGRVFAFADEQQPLNWVQTHDYSDELGTILSITIARKETIDVNDRDAV<br>TREVQKMFPGVEVLGTAAYDWTADPFSLGAWAAYGVGQLSRLKDLQA<br>AEGRILFAGAETSNGWHANIDGAVESGLRAGREVKQLLS |
| NicA2G106A<br>(G106A<br>substitution) | 12 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGAAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2A107R<br>(A107R<br>substitution) | 13 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGRVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2Δ50A107R<br>(A107R<br>substitution;<br>N-terminal | 14 | GFDYDVVVVGGGFAGATAARECGLQGYRTLLLEARSRLGGRTFTSRFAG<br>QEIEFGGRVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM |

TABLE 1-continued

Amino Acid Sequences of NicA2 and Exemplary Variants

| Enzyme | SEQ ID NO. | Sequence |
|---|---|---|
| deletion of residues 1-50) | | DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2A107K (A107K substitution) | 36 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGKWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2A107T (A107T substitution) | 15 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGTWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2A107G (A107G substitution) | 16 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGGWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2A107H (A107H substitution) | 17 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGHWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2A107P (A107P substitution) | 18 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGPWVHWLQPHVWAEMQRYGLGVVEDPLTNLDKTLIMYNDGSV<br>ESISPDEFGKNIRIAFEKLCHDAWEVFPRPHEPMFTERARELDKSSVLDRIK<br>TLGLSRLQQAQINSYMALYAGETTDKFGLPGVLKLFACGGWNYDAFMD<br>TETHYRIQGGTIGLINAMLTDSGAEVRMSVPVTAVEQVNGGVKIKTDDD<br>EIITAGVVVMTVPLNTYKHIGFTPALSKGKQRFIKEGQLSKGAKLYVHVK<br>QNLGRVFAFADEQQPLNWVQTHDYSDELGTILSITIARKETIDVNDRDAV<br>TREVQKMFPGVEVLGTAAYDWTADPFSLGAWAAYGVGQLSRLKDLQA<br>AEGRILFAGAETSNGWHANIDGAVESGLRAGREVKQLLS |
| NicA2E249W (E249W substitution) | 19 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTWTHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |

TABLE 1-continued

Amino Acid Sequences of NicA2 and Exemplary Variants

| Enzyme | SEQ ID NO. | Sequence |
|---|---|---|
| NicA2E249D (E249D substitution) | 20 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTDTHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2F355H (F355H substitution) | 21 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAHADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2F355K (F355K substitution) | 22 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAKADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2F355E (F355E substitution) | 23 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAEADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2F355C (F355C substitution) | 37 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFACADEQQPLNWVQTHDYSDELGTILSITIARKETIDVNDRDA VTREVQKMFPGVEVLGTAAYDWTADPFSLGAWAAYGVGQLSRLKDLQ AAEGRILFAGAETSNGWHANIDGAVESGLRAGREVKQLLS |
| NicA2A426Q (A426Q substitution) | 24 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV KQNLGRVFAFADEQQPLNWVQTHDYSDELGTILSITIARKETIDVNDRDA VTREVQKMFPGVEVLGTAAYDWTADPFSLGQWAAYGVGQLSRLKDLQ AAEGRILFAGAETSNGWHANIDGAVESGLRAGREVKQLLS |
| NicA2A426W (A426W substitution) | 25 | SDKTKTNEGFSRRSFIGSAAVVTAGVAGLGAIDAASATQKTNRASTVKG GFDYDVVVVGGGFAGATAARECGLQGYRTLLLEARSRLGGRTFTSRFAG QEIEFGGAWVHWLQPHVWAEMQRYGLGVVEDPLTNLDKTLIMYNDGS VESISPDEFGKNIRIAFEKLCHDAWEVFPRPHEPMFTERARELDKSSVLDRI KTLGLSRLQQAQINSYMALYAGETTDKFGLPGVLKLFACGGWNYDAFM DTETHYRIQGGTIGLINAMLTDSGAEVRMSVPVTAVEQVNGGVKIKTDD DEIITAGVVVMTVPLNTYKHIGFTPALSKGKQRFIKEGQLSKGAKLYVHV |

TABLE 1-continued

Amino Acid Sequences of NicA2 and Exemplary Variants

| Enzyme | SEQ ID NO. | Sequence |
|---|---|---|
| | | KQNLGRVFAFADEQQPLNWVQTHDYSDELGTILSITIARKETIDVNDRDA<br>VTREVQKMFPGVEVLGTAAYDWTADPFSLGWWAAYGVGQLSRLKDLQ<br>AAEGRILFAGAETSNGWHANIDGAVESGLRAGREVKQLLS |
| NicA2A426P<br>(A426P<br>substitution) | 26 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGPWAAYGVGQLSRLKDLQ<br>AAEGRILFAGAETSNGWHANIDGAVESGLRAGREVKQLLS |
| NicA2A426C<br>(A426C<br>substitution) | 27 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGAWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAFADEQQPLNWVQTHDYSDELGTILSITIARKETIDVNDRDA<br>VTREVQKMFPGVEVLGTAAYDWTADPFSLGCWAAYGVGQLSRLKDLQ<br>AAEGRILFAGAETSNGWHANIDGAVESGLRAGREVKQLLS |
| NicA2Δ50F104I;<br>A107R<br>(F104I &<br>A107R<br>substitution) | 28 | GFDYDVVVVGGGFAGATAARECGLQGYRTLLLEARSRLGGRTFTSRFAG<br>QEIEIGGRWVHWLQPHVWAEMQRYGLGVVEDPLTNLDKTLIIVIYNDGSV<br>ESISPDEFGKNIRIAFEKLCHDAWEVFPRPHEPMFTERARELDKSSVLDRIK<br>TLGLSRLQQAQINSYMALYAGETTDKFGLPGVLKLFACGGWNYDAFMD<br>TETHYRIQGGTIGLINAMLTDSGAEVRMSVPVTAVEQVNGGVKIKTDDD<br>EIITAGVVVMTVPLNTYKHIGFTPALSKGKQRFIKEGQLSKGAKLYVHVK<br>QNLGRVFAFADEQQPLNWVQTHDYSDELGTILSITIARKETIDVNDRDAV<br>TREVQKMFPGVEVLGTAAYDWTADPFSLGAWAAYGVGQLSRLKDLQA<br>AEGRILFAGAETSNGWHANIDGAVESGLRAGREVKQLLS |
| NicA2F355H;<br>A107R<br>(F355H and<br>A107R<br>substitutions) | 34 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEFGGRWVHWLQPHVWAEMQRYGLGVVEDPLTNLDKTLIMYNDGS<br>VESISPDEFGKNIRIAFEKLCHDAWEVFPRPHEPMFTERARELDKSSVLDRI<br>KTLGLSRLQQAQINSYMALYAGETTDKFGLPGVLKLFACGGWNYDAFM<br>DTETHYRIQGGTIGLINAMLTDSGAEVRMSVPVTAVEQVNGGVKIKTDD<br>DEIITAGVVVMTVPLNTYKHIGFTPALSKGKQRFIKEGQLSKGAKLYVHV<br>KQNLGRVFAHADEQQPLNWVQTHDYSDELGTILSITIARKETIDVNDRDA<br>VTREVQKMFPGVEVLGTAAYDWTADPFSLGAWAAYGVGQLSRLKDLQ<br>AAEGRILFAGAETSNGWHANIDGAVESGLRAGREVKQLLS |
| NicA2F104I;<br>A107R;<br>A426C<br>(F104I,<br>A107R, and<br>A426C<br>substitutions) | 35 | SDKTKTNEGFSRRSFIGSAAVVTAGVAGLGAIDAASATQKTNRASTVKG<br>GFDYDVVVVGGGFAGATAARECGLQGYRTLLLEARSRLGGRTFTSRFAG<br>QEIEIGGRWVHWLQPHVWAEMQRYGLGVVEDPLTNLDKTLIMYNDGSV<br>ESISPDEFGKNIRIAFEKLCHDAWEVFPRPHEPMFTERARELDKSSVLDRIK<br>TLGLSRLQQAQINSYMALYAGETTDKFGLPGVLKLFACGGWNYDAFMD<br>TETHYRIQGGTIGLINAMLTDSGAEVRMSVPVTAVEQVNGGVKIKTDDD<br>EIITAGVVVMTVPLNTYKHIGFTPALSKGKQRFIKEGQLSKGAKLYVHVK<br>QNLGRVFAFADEQQPLNWVQTHDYSDELGTILSITIARKETIDVNDRDAV<br>TREVQKMFPGVEVLGTAAYDWTADPFSLGCWAAYGVGQLSRLKDLQA<br>AEGRILFAGAETSNGWHANIDGAVESGLRAGREVKQLLS |

*The N-terminal methionine residue (M) of SEQ ID NO: 1 is cleaved off in the purified product; however all amino acid position designations disclosed herein take the methionine residue into account for the purpose of maintaining amino acid numbering conventions used in the art for the wild-type NicA2 sequence.
**Underlined sequences in wild-type NicA2 identify the six highest ranked immunogenic regions identified by the online MiFIC-II Binding Predictions tool on the Immune Epitope Database and Analysis Resource website (iedb.org) using the specific human WIC allele HLA DRB1*0401.
†Residues highlighted in grey were identified as MHCII epitopes as disclosed in Example 2.

As noted above the nicotine-degrading enzyme variants may exhibit increased nicotine-degrading activity and/or decreased immunogenicity relative to the wild-type NicA2 enzyme. The variants may comprise one or more mutations to the amino acid sequence of wild-type NicA2, including one or more deletions, additions, or substitutions. A substitution mutation may be "conservative" or "non-conservative." "Conservative" refers to a substitution within the same family of amino acids, while "non-conservative" refers to substitutions across families of amino acids. Families of amino acids and "conservative" and "non-conservative" substitutions relative thereto are known in the art. For example, the naturally occurring amino acids may be divided into the following four families and conservative substitutions will take place within those families, while non-conservative substitutions will take place across different families.
1) Amino acids with basic side chains: lysine, arginine, histidine.
2) Amino acids with acidic side chains: aspartic acid, glutamic acid
3) Amino acids with uncharged polar side chains: asparagine, glutamine, serine, threonine, tyrosine.
4) Amino acids with nonpolar side chains: glycine, alanine, valine, leucine, isoleucine, proline, phenylalanine, methionine, tryptophan, cysteine.

Figure 3:
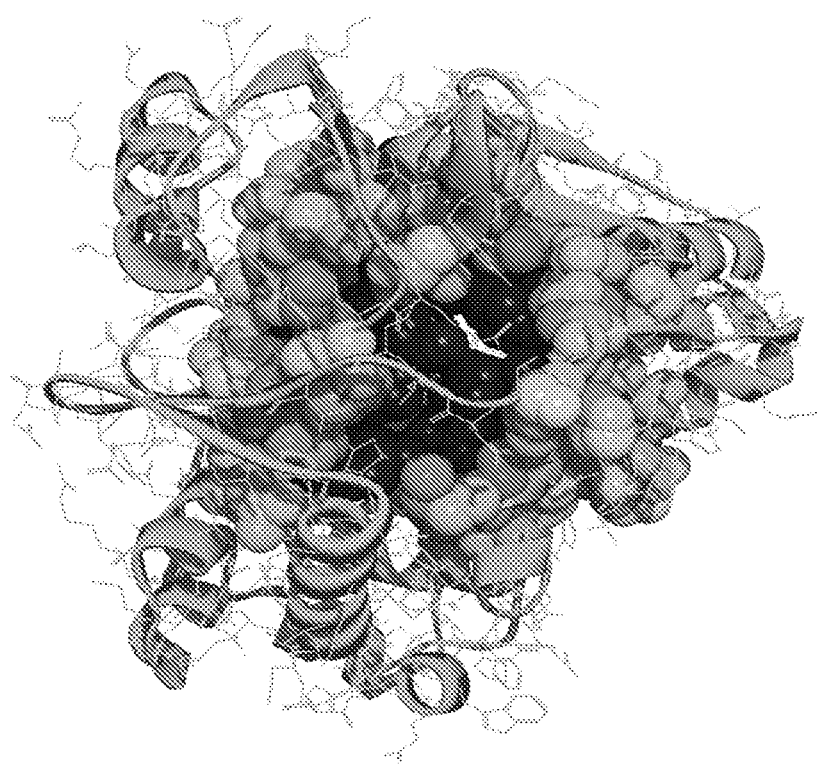
Figure 4C:
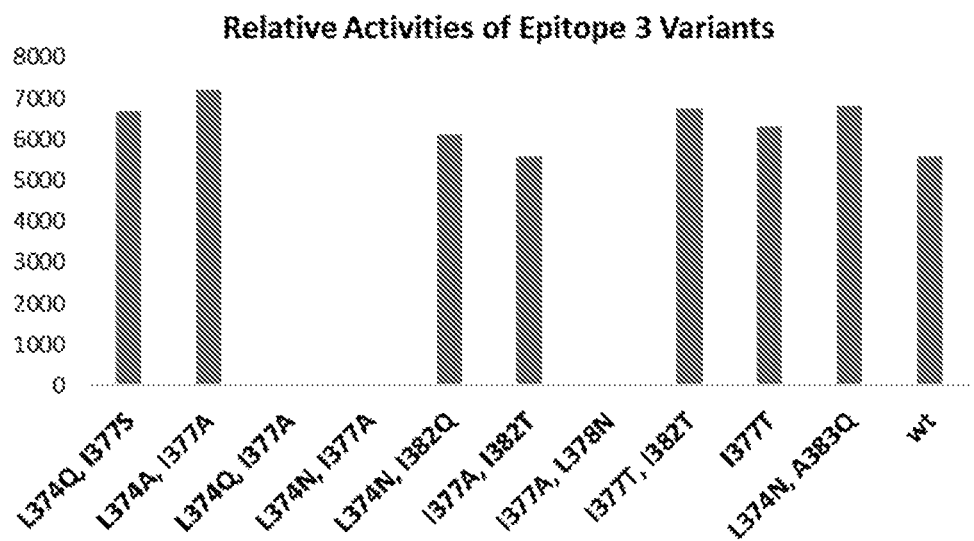
Figure 4D:
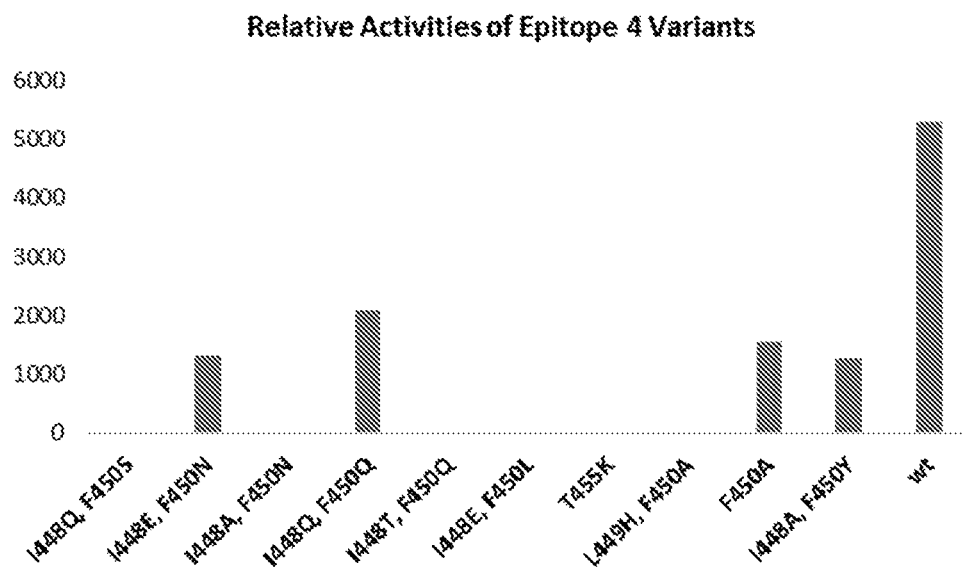

In some embodiments, the nicotine-degrading enzyme variants comprise one or more mutations in an active site of the wild-type NicA2 enzyme relevant to its nicotine-degrading activity, such as a mutation at one or more positions selected from any one of amino acid residues 104, 106, 107, 249, 355, or 426 of SEQ ID NO:1, such as one or more conservative substitutions, non-conservative substitutions, additions, or deletions in positions 104, 106, 107, 249, 355, or 426 and shown on the structure in FIG. 3. The Shell One residues identified in FIG. 3 make up the cavity surface. In some embodiments, the variants may comprise one, two, or three or more substitutions.

In some embodiments, at least one mutation that increases the nicotine-degrading activity or increases the catalytic activity of the enzyme is introduced into the variant, allowing the variant to more rapidly and/or more efficiently break-down nicotine. In some embodiments, such a mutation may improve various measures of enzymatic performance, including but not limited to, increasing $k_{cat}$, lowering $K_M$, increasing $k_{cat}/K_M$ and/or increasing $V_{max}$. Thus, in some embodiments, a variant may comprise 1, 2, 3, 4, 5, 6, 7, 8, 9, or 10 or more mutations in an active site of the wild-type NicA2 enzyme and/or in the aromatic cage, and exhibit increased nicotine-degrading activity as measured by increased $k_{cat}$, lowered $K_M$, increased $k_{cat}/K_M$, and/or increased $V_{max}$, relative to the wild-type NicA2 enzyme.

In some embodiments, the nicotine-degrading enzyme variants comprise one or more mutations including a mutation in the phenylalanine (F) at position 104 of SEQ ID NO:1, the glycine (G) at position 106 of SEQ ID NO:1, the alanine (A) at position 107 of SEQ ID NO:1, the glutamic acid (E) at position 249 of SEQ ID NO: 1, the phenylalanine (F) at position 355 of SEQ ID NO:1, and/or the alanine (A) at position 426 of SEQ ID NO:1, such as one or more conservative substitutions, non-conservative substitutions, additions, or deletions. Thus, in some embodiments, a mutation that increases the nicotine-degrading activity is at one or more of positions 104, 106, 107, 249, 355, or 426 of SEQ ID NO:1, such as a conservative substitution, non-conservative substitution, addition, or deletion at one or more of positions 104, 106, 107, 249, 355, or 426 of SEQ ID NO:1. In preferred embodiments, the variant may comprise one or more of an F104R substitution, an F104I substitution, an F104S substitution, an F104T substitution, a G106A substitution, an A107T substitution, an A107G substitution, an F355H substitution, or an A426C substitution.

In some embodiments, the mutation at position 104 is the substitution F104R, where the phenylalanine (F) at position 104 of SEQ ID NO:1 is substituted with arginine (R). The variant having the amino acid sequence of SEQ ID NO:5 is an example of this type of variant. In some embodiments, the mutation at position 104 is the substitution F104K, where the phenylalanine (F) at position 104 of SEQ ID NO:1 is substituted with lysine (K). The variant having the amino acid sequence of SEQ ID NO:6 is an example of this type of variant. In some embodiments, the mutation at position 104 is the substitution F104I, where the phenylalanine (F) at position 104 of SEQ ID NO:1 is substituted with isoleucine (I). The variants having the amino acid sequences of SEQ ID NOs:7 and 28 are examples of this type of variant. In some embodiments, the mutation at position 104 is the substitution F104L, where the phenylalanine (F) at position 104 of SEQ ID NO: 1 is substituted with leucine (L). The variant having the amino acid sequence of SEQ ID NO:8 is an example of this type of variant. In some embodiments, the mutation at position 104 is the substitution F104S, where the phenylalanine (F) at position 104 of SEQ ID NO:1 is substituted with serine (S). The variant having the amino acid sequence of SEQ ID NO:9 is an example of this type of variant. In some embodiments, the mutation at position 104 is the substitution F104T, where the phenylalanine (F) at position 104 of SEQ ID NO:1 is substituted with threonine (T). The variant having the amino acid sequence of SEQ ID NO:10 is an example of this type of variant.

In some embodiments, the mutation at position 106 is the substitution G106S, where the glycine (G) at position 106 of SEQ ID NO:1 is substituted with serine (S). The variant having the amino acid sequence of SEQ ID NO:11 is an example of this type of variant. In some embodiments, the mutation at position 106 is the substitution G106A, where the glycine (G) at position 106 of SEQ ID NO:1 is substituted with alanine (A). The variant having the amino acid sequence of SEQ ID NO:12 is an example of this type of variant.

In some embodiments, the mutation at position 107 is the substitution A107R, where the alanine (A) at position 107 of SEQ ID NO:1 is substituted with arginine (R). The variants having the amino acid sequences of SEQ ID NOs:13, 14, 28, 34, and 35 are examples of this type of variant. In some embodiments, the mutation at position 107 is the substitution A107T, where the alanine (A) at position 107 of SEQ ID NO:1 is substituted with threonine (T). The variant having the amino acid sequence of SEQ ID NO:15 is an example of this type of variant. In some embodiments, the mutation at position 107 is the substitution A107K, where the alanine (A) at position 107 of SEQ ID NO:1 is substituted with lysine (K). The variant having the amino acid sequence of SEQ ID NO:36 is an example of this type of variant. In some embodiments, the mutation at position 107 is the substitution A107G, where the alanine (A) at position 107 of SEQ ID NO:1 is substituted with glycine (G). The variant having the amino acid sequence of SEQ ID NO:16 is an example of this type of variant. In some embodiments, the mutation at position 107 is the substitution A107H, where the alanine (A) at position 107 of SEQ ID NO:1 is substituted with histidine (H). The variant having the amino acid sequence of SEQ ID NO:17 is an example of this type of variant. In some embodiments, the mutation at position 107 is the substitution A107P, where the alanine (A) at position 107 of SEQ ID NO:1 is substituted with proline (P). The variant having the amino acid sequence of SEQ ID NO:18 is an example of this type of variant.

In some embodiments, the mutation at position 249 is the substitution E249W, where the glutamic acid (E) at position 249 of SEQ ID NO:1 is substituted with tryptophan (W). The variant having the amino acid sequence of SEQ ID NO:19 is an example of this type of variant. In some embodiments, the mutation at position 249 is the substitution E249D, where the glutamic acid (E) at position 249 of SEQ ID NO:1 is substituted with aspartic acid (D). The variant having the amino acid sequence of SEQ ID NO:20 is an example of this type of variant.

In some embodiments, the mutation at position 355 is the substitution F355H, where the phenylalanine (F) at position 355 of SEQ ID NO:1 is substituted with histidine (H). The variant having the amino acid sequence of SEQ ID NO:21 is an example of this type of variant. In some embodiments, the mutation at position 355 is the substitution F355K, where the phenylalanine (F) at position 355 of SEQ ID NO:1 is substituted with lysine (K). The variant having the amino acid sequence of SEQ ID NO:22 is an example of this type of variant. In some embodiments, the mutation at position 355 is the substitution F355E, where the phenylalanine (F) at position 355 of SEQ ID NO:1 is substituted with glutamic acid (E). The variant having the amino acid sequence of SEQ ID NO:23 is an example of this type of variant. In some embodiments, the mutation at position 355 is the substitution F355C, where the phenylalanine (F) at position 355 of SEQ ID NO:1 is substituted with cysteine (C). The variant having the amino acid sequence of SEQ ID NO:37 is an example of this type of variant.

In some embodiments, the mutation at position 426 is the substitution A426Q, where the alanine (A) at position 426 of SEQ ID NO:1 is substituted with glutamine (Q). The variant having the amino acid sequence of SEQ ID NO:24 is an example of this type of variant. In some embodiments, the mutation at position 426 is the substitution A426W, where the alanine (A) at position 426 of SEQ ID NO:1 is substituted with tryptophan (W). The variant having the amino acid sequence of SEQ ID NO:25 is an example of this type of variant. In some embodiments, the mutation at position 426 is the substitution A426P, where the alanine (A) at position 426 of SEQ ID NO:1 is substituted with proline (P). The variant having the amino acid sequence of SEQ ID NO:26 is an example of this type of variant. In some embodiments, the mutation at position 426 is the substitution A426C, where the alanine (A) at position 426 of SEQ ID NO:1 is substituted with cysteine (C). The variant having the amino acid sequence of SEQ ID NO:27 is an example of this type of variant.

Additionally, any of the foregoing substitutions that increase nicotine degrading activity may be combined with one or more additional substitutions in order to further increase nicotine degrading activity. It is believed that combining the disclosed substitutions with additional activity-increasing substitutions may have a synergistic effect on the nicotine degrading activity of a given variant (see, e.g., NicA2A50+F104I; A107R (SEQ ID NO: 28); NicA2+A107R; F355H (SEQ ID NO: 34); NicA2+A107R; F104I; A426C (SEQ ID NO: 35) in Table 1 or Table 3 of Example 1). For instance, in addition to the substitutions disclosed in Table 1, in some embodiments a variant may comprise one or two or three or more substitutions at positions 91, 217, 250, 340, 366, 381, 427, 462, or 463 of SEQ ID NO:1. In some embodiments, the further substitutions may be selected from any one or two or three or more F104L, G106S, A107H, A107P, A107R, A107K, A107T, F355C, F355V, W427Q, W427E, W427S, W427M, W427H, W427L, W427R, R91A, R91Q, R91F, R91G, R91T, R91L, R91S, R91N, T250G, T250L, T250R, T250V, T250P, K340P, K340I, K340V, K340D, K340E, Q366K, Q366E, Q366V, Q366L, Q366I, Q366Y, T381P, T381I, T381V, T381Q, T381N, T381L, T381M, N462L, N462Y, N462S, N462F, N462G, N462E, N462A, N462M, I463F, I463Y, I463A, I463V, I463L, L217Q, L217G, L217E, L217I, L217C, and L217S. In some embodiments, the further substitution may comprise A107R.

Additionally or alternatively, in some embodiments, the disclosed NicA2 variants may comprise a combination of at least one of the substitution and/or deletion mutations disclosed above in combination with one or more additional substitution mutations. In other words, in some embodiments, the disclosed NicA2 variants may comprise a combination of one or more of the substitution and/or deletion mutations disclosed herein in combination with 1, 2, 3, 4, 5, 6, 7, 8, 9, or 10 or more additional substitution mutations. For example, one or more of the nicotine-degrading enzyme disclosed above (e.g., the variants disclosed in Table 1 or in FIGS. 13 and 14) may further comprise one or more other substitutions based on other nicotine-degrading enzymes, including but not limited to, NicA2 variants possessing the mutations F163A, Y214A, Y218A, Y242A, M246A, E249A, F353V, F355V, and W364V (denoted M9 in U.S. 2019/0153403); the mutations F353V, F355V, and W364V (denoted M3V in U.S. 2019/0153403); the mutations F353A, F355A, and W364A (denoted M3A in U.S. 2019/0153403); the mutations F353V, F355V, W364V, Y214A, and Y218A (denoted M5 in U.S. 2019/0153403); or the mutations F353V, F355V, W364V, Y214A, Y218A, F163A, E249A (denoted M7 in U.S. 2019/0153403). Thus, in some embodiments, the nicotine-degrading enzyme variant may comprise, for example, an A107R substitution (e.g., SEQ ID NOs: 13, 14, 28, 34, or 35) plus one or more or all of F163A, Y214A, Y218A, Y242A, M246A, E249A, F353V, F355V, and W364V substitutions. In some embodiments, the nicotine-degrading enzyme variant may comprise, for example, one of the F355 substitutions disclosed herein (e.g., SEQ ID NOs: 21-23, 34, or 37) plus one or more or all of F163A, Y214A, Y218A, Y242A, M246A, E249A, F353V, and W364V substitutions. In some embodiments, the nicotine-degrading enzyme variant may comprise, for example, a double or triple substitution as disclosed above (e.g., SEQ ID NOs: 28, 34, or 35; see, e.g., FIG. 14) plus one or more or all of F163A, Y214A, Y218A, Y242A, M246A, E249A, F353V, and W364V substitutions. In some embodiments, the nicotine-degrading enzyme variant may comprise, for example, the M9, M3V, M3A, M5, or M7 mutations, as described above and denoted in U.S. 2019/0153403, and have an N-terminal deletion of from 1 to 52 amino acid residues, such as a 50 residue deletion (i.e., a A50 backbone), a 25 residue deletion (i.e., a A25 backbone), or a 38 residue deletion (i.e., a A38 backbone).

Additionally or alternatively, one or more of the nicotine-degrading enzyme variants disclosed above (e.g., the variants disclosed in Table 1 or in FIGS. 13 and 14) may further comprise one or more substitution mutations at one or more or all of positions 91, 104, 106, 107, 217, 250, 340, 355, 366, 381, 427, 462, and 463 of SEQ ID NO:1. See WO 2018/144879.

In some embodiments, the nicotine-degrading enzyme variants may further comprise one or more mutations that decrease the immunogenicity of the variant. For example, in some embodiments, the disclosed variants may further comprise one or more additions, substitutions, or deletions within an immunogenic T-cell epitope, such as one or more mutations within an immunogenic T-cell epitope within a region selected from positions 10-32, 68-94, 189-225, 248-285, 296-327, 336-391, or 435-459 of SEQ ID NO:1, such as one or more mutations within an immunogenic T-cell epitope selected from positions 16-24, 73-81, 258-266, 302-310, 373-381, or 447-455 of SEQ ID NO:1, such as one or more conservative substitutions, non-conservative substitutions, additions, or deletions in one or more of these regions. Thus, in some embodiments, a variant may further comprise 1, 2, 3, 4, 5, 6, 7, 8, 9, or 10 or more mutations in 1, 2, 3, 4, 5, 6, or 7, immunogenic T-cells epitopes. In some embodiments, such variants exhibit reduced immunogenicity compared to wild-type NicA2 when administered to a mammalian subject. In some embodiments, such variants exhibit reduced immunogenicity compared to the corresponding variant enzyme without one or more mutations in a T-cell epitope when administered to a mammalian subject.

In some embodiments, the nicotine-degrading enzymes variants may further comprise a mutation in an immunogenic T-cell epitope at one or more positions selected from 74, 77, 78, 80, 262-266, 303, 304, 306, 310, 374, 377, 378, 382, 383, 450-452, or 457 of SEQ ID NO:1, including all permutations and combinations thereof. For example, a variant may further comprise any one or more of the mutations set forth below, including one or more of the exemplary mutations in Epitope B, one or more of the exemplary mutations in Epitope 1, one or more of the exemplary mutations in Epitope 2, one or more of the exemplary mutations in Epitope 3, and/or one or more of the exemplary mutations in Epitope 4.

TABLE 2

Exemplary Mutations in the NicA2 Epitopes (numbering based on SEQ ID NO: 1)

| Epitope B | Epitope 1 | Epitope 2 | Epitope 3 | Epitope 4 |
|---|---|---|---|---|
| L74N Y77R | I262A, A264Q | V303T, V304N, M306I | L374Q, I377S | I448Q, F450S |
| L74N, Y77K | I262K, L266D | V304A, M306Q | L374A, I377A | I448E, F450N |
| L74Q, Y77R | I262T | V304A, M306N | L374Q, I377A | I448A, F450N |
| L74Q, Y77N | I262S | V304A | L374N, I377A | I448Q, F450Q |
| L74N, Y77Q | I262D, L266K | V304A, M306H | L374N, I382Q | I448T, F450Q |
| L74N, Y77H | I262A | V304N, M306H | I377A, I382T | I448E, F450L |
| L74N, L80H | I262T, A264L | V304Q, M306H | I377A, L378N | T455K |
| L80F | I262T, N263R | V304N, M306I | I377T, I382T | L449H, F450A |
| Y77R | M265H | V304T, M306I | I377T | F450A |
| R78Q | I262A, A264N | M306I, L310R | L374N, A383Q | I448A, F450Y |

Additionally or alternatively, in some embodiments, the nicotine-degrading enzyme variants comprise an N-terminal deletion of from 1 to 52 amino acid residues of SEQ ID NO:1. For example, in some embodiments a variant comprises an N-terminal deletion of amino acid residues 1-16, 1-25, 1-38, 1-50, 1-51, or 1-52 of SEQ ID NO:1. Thus, the disclosed variants may comprise an N-terminal deletion of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 consecutive amino acids.

In some embodiments, the disclosed variants may additionally or alternatively comprise a deletion at the C-terminus of the peptide. For example, the disclosed variants may comprise a deletion of one or more amino acids at the C-terminus of the peptide. For example, in a NicA2 variant, the amino acid corresponding to S482 of the wild-type sequence may be deleted.

In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the wild-type NicA2 enzyme (SEQ ID NO:1), or to an N-terminal deletion variant thereof having a deletion of up to 52 N-terminal amino acid residues of SEQ ID NO:1.

In some embodiments, a nicotine-degrading enzyme variant as described herein is or comprises SEQ ID NO:5. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:5.

In some embodiments, a nicotine-degrading enzyme variant as described herein is or comprises SEQ ID NO:6. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:6.

In some embodiments, a nicotine-degrading enzyme variant as described herein is or comprises SEQ ID NO:7. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:7.

In some embodiments, a nicotine-degrading enzyme variant as described herein is or comprises SEQ ID NO:8. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:8.

In some embodiments, a nicotine-degrading enzyme variant as described herein is or comprises SEQ ID NO:9. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:9.

In some embodiments, a nicotine-degrading enzyme variant as described herein is or comprises SEQ ID NO:10. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:10.

In some embodiments, a nicotine-degrading enzyme variant as described herein is or comprises SEQ ID NO:11. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:11.

In some embodiments, a nicotine-degrading enzyme variant as described herein is or comprises SEQ ID NO:12. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:12.

In some embodiments, a nicotine-degrading enzyme variant as described herein is or comprises SEQ ID NO:15. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:15.

In some embodiments, a nicotine-degrading enzyme variant as described herein is or comprises SEQ ID NO:16. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:16.

In some embodiments, a nicotine-degrading enzyme variant as described herein is or comprises SEQ ID NO:17. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:17.

In some embodiments, a nicotine-degrading enzyme variant as described herein is or comprises SEQ ID NO:18. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:18.

In some embodiments, a nicotine-degrading enzyme variant as described herein is or comprises SEQ ID NO:19. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:19.

In some embodiments, a nicotine-degrading enzyme variant as described herein is or comprises SEQ ID NO:20. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:20.

In some embodiments, a nicotine-degrading enzyme variant as described herein is or comprises SEQ ID NO:21. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:21.

In some embodiments, a nicotine-degrading enzyme variant as described herein is or comprises SEQ ID NO:22. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:22.

In some embodiments, a nicotine-degrading enzyme variant as described herein is or comprises SEQ ID NO:23. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:23.

In some embodiments, a nicotine-degrading enzyme variant as described herein is or comprises SEQ ID NO:24. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:24.

In some embodiments, a nicotine-degrading enzyme variant as described herein is or comprises SEQ ID NO:25. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:25.

In some embodiments, a nicotine-degrading enzyme variant as described herein is or comprises SEQ ID NO:26. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:26.

In some embodiments, a nicotine-degrading enzyme variant as described herein is or comprises SEQ ID NO:27. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:27.

In some embodiments, a nicotine-degrading enzyme variant as described herein is or comprises SEQ ID NO:28. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:28.

In some embodiments, a nicotine-degrading enzyme variant as described herein is or comprises SEQ ID NO:34. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:34.

In some embodiments, a nicotine-degrading enzyme variant as described herein is or comprises SEQ ID NO:35. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:35.

In some embodiments, a nicotine-degrading enzyme variant as described herein is or comprises SEQ ID NO:36. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:36.

In some embodiments, a nicotine-degrading enzyme variant as described herein is or comprises SEQ ID NO:37. In some embodiments, a nicotine-degrading enzyme variant as described herein has at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity with the variant sequence of SEQ ID NO:37.

In some embodiments, a variant as described herein exhibits increased nicotine-degrading activity relative to the wild-type NicA2 enzyme, such that its activity is at least about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, about 500%, about 550%, about 600%, about 650%, about 700%, about 750%, about 800%, about 850%, about 900%, about 950%, about 1000%, about 1100%, about 1200%, about 1300%, about 1400%, about 1500%, about 1600%, about 1700%, about 1800%, about 1900%, about 2000%, about 2250%, about 2500%, about 2750%, about 3000%, about 3250%, about 3500%, about 3750%, about 4000%, about 4250%, about 4500%, about 4750%, or about 5000% or more than that of the wild-type NicA2 enzyme, as determined by an assay such as an AMPLEX® Red assay (Thermo Fisher Scientific) . 10099 In some embodiments, a variant as described herein exhibits increased nicotine-degrading activity relative to the wild-type NicA2 enzyme, such that its activity is at least about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, about 500%, about 550%, about 600%, about 650%, about 700%, about 750%, about 800%, about 850%, about 900%, about 950%, about 1000%, about 1100%, about 1200%, about 1300%, about 1400%, about 1500%, about 1600%, about 1700%, about 1800%, about 1900%, about 2000%, about 2250%, about 2500%, about 2750%, about 3000%, about 3250%, about 3500%, about 3750%, about 4000%, about 4250%, about 4500%, about 4750%, or about 5000% or more than that of the wild-type NicA2 enzyme as determined by an assay where residual nicotine concentrations are measured using Gas Chromatography (G C; Hieda et al.: Immunization of rats reduces nicotine distribution to brain. Psychopharmacology, 143, 150-157, 1999) after incubation with a fixed concentration of enzyme in either buffer or rat serum at 37° C. and quenching activity at fixed time points by mixing with MeOH.

In some embodiments, a variant as described herein exhibits decreased immunogenicity in a mammalian subject relative to wild-type NicA2, such that it is at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% less immunogenic than the wild-type NicA2 enzyme. Unless otherwise specified, "decreased immunogenicity" as compared to the wild-type NicA2 enzyme as used herein refers decreased immunogenicity as shown by one or more of in silico approaches, in vitro assays, in vivo studies (e.g., using transgenic animals), ex vivo studies using human T-cells, or clinical studies with human subjects.

IV. Pharmaceutical Compositions

The nicotine-degrading enzyme variants disclosed herein can be formulated into pharmaceutical compositions suitable for administration to the target subject (i.e., a human or other mammal) via a predetermined route of administration, as discussed in more detail below.

Pharmaceutical compositions may include one or more variants as described herein and a pharmaceutically acceptable carrier or diluent.

The compositions may be formulated for intravenous, subcutaneous, intraperitoneal, intramuscular, oral, nasal, pulmonary, ocular, vaginal, or rectal administration. In some embodiments, the compositions are formulated for intravenous, subcutaneous, intraperitoneal, or intramuscular administration, such as in a solution, suspension, emulsion, liposome formulation, etc. The pharmaceutical compositions can be formulated to be an immediate-release composition, sustained-release composition, delayed-release composition, etc., using techniques known in the art Pharmaceutically acceptable carriers for various dosage forms are known in the art. For example, excipients, lubricants, binders, and disintegrants for solid preparations are known; solvents, solubilizing agents, suspending agents, isotonicity agents, buffers, and soothing agents for liquid preparations are known. In some embodiments, the pharmaceutical compositions include one or more additional components, such as one or more preservatives, antioxidants, colorants, sweetening/flavoring agents, adsorbing agents, wetting agents and the like.

In some embodiments, the composition is formulated for administration by injection or infusion. In some embodiments, the composition is formulated for oral administration.

In some embodiments, the nicotine-degrading enzyme variant is a long-acting variant that has been modified in order to extend its half-life in vivo (after administration). Various techniques are known in the art for extending the circulating half-life of peptides. For example, in some embodiments the variant is conjugated to polyethylene glycol (PEG) or a similar polymer that prolongs half-life. Conjugating PEG to the disclosed nicotine-degrading enzyme variants can improve the pharmacokinetic properties of the variant. In some embodiments PEGylation has one or more effects selected from masking one or more immunogenic epitopes of the variant, decreasing variant-specific antibody titers, and attenuating T-cell proliferation and/or cytokine responses. Additionally or alternatively, in some embodiments, conjugating the variants to PEG does not decrease the enzymatic activity of the nicotine-degrading enzyme variants, or does not significantly decrease the enzymatic activity, or does not eliminate the enzymatic activity.

The PEG chain length and architecture (i.e. linear vs. branched) may be selected and varied to impact, impart, or promote different properties, as illustrated in the examples below. PEG can be conjugated to the variants by methods known for conjugating PEG to proteins, including those illustrated in the examples below. Any of the variants described herein can be PEGylated, including variants defined by or comprising any of SEQ ID NOs: 5-12 and 15-28. For the purposes of conjugating PEG to the disclosed enzyme variants, the size or length of the PEG polymers can vary. For example, linear PEG conjugated to the disclosed enzyme variants may be in the range of 1-50 kDa, 5-40 kDa, or 10-20 kDa, such as 1, 2, 3, 4, 5, 6, 7, 8, 9, 10, 11, 12, 13, 14, 15, 16, 17, 18, 19, 20, 25, 30, 35, 40, 45, or 50 kDa. Additionally, the PEG polymers may be branched, with size in the range of 20-80 kDa, such as 20, 40, 60 or 80 kDa.

In some embodiments, the variant is fused to an albumin-binding peptide, an albumin-binding protein domain, human serum albumin, or an inert polypeptide. Exemplary inert polypeptides that have been used to increase the circulating half-life of peptides include, but are not limited to, XTEN® (also known as recombinant PEG or "rPEG"), a homo-amino acid polymer (HAP; HAPylation), a proline-alanine serine polymer (PAS; PASylation), or an elastin-like peptide (ELP; ELPylation). As used herein, "fused to" includes genetic fusion, directly or through a linker, resulting in a single polypeptide containing multiple domains, unless otherwise specified.

V. Methods of Treating Nicotine Addiction or Facilitating Smoking Cessation

As noted above, the variants described herein are useful in methods of treating nicotine addiction and/or facilitating smoking cessation (or the cessation of use of other tobacco products) or preventing relapse of smoking (or consumption of other tobacco products) in a mammalian subject in need thereof. (For convenience, in the discussion that follows, these methods are referred to collectively as treating nicotine addiction or facilitating smoking cessation.) In some embodiments, the subject is a human subject addicted to nicotine or desiring to quit smoking or maintain abstinence from smoking or consumption of other nicotine products, or prevent relapse of smoking or consumption of other nicotine products.

The methods generally involve administering a therapeutically effective amount of a nicotine-degrading enzyme variant as described herein (or a pharmaceutical composition comprising the same) to the subject. However, in some embodiments, the methods comprise administering a nucleic acid encoding the nicotine-degrading enzyme variant in a construct that expresses the variant in vivo. For example, in such embodiments, the nucleic acid can be provided in a suitable vector, such as an adeno-associated virus (AAV) gene transfer vector. Other exemplary vectors that are suitable for use in such methods are known in the art. See, e.g., Lukashev and Zamyatnin, Biochem., 81(7): 700-8 (2016)). Exemplary vectors may include one or more enhancers (e.g., a cytomegalovirus (CMV) enhancer), promoters (e.g., chicken β-actin promoter), and/or other elements enhancing the properties of the expression cassette. Methods of making suitable vectors and general methods of using expression vectors in vivo are known in the art. See, e.g., Hicks et al., Sci. Transl. Med., 4(140): 140ra87 (2012).

In some embodiments, a subject in need of treatment for nicotine addiction or facilitation of smoking cessation is a human subject who consumes nicotine products, such as smoking tobacco, chewing tobacco, electronic cigarettes, and/or other nicotine delivery devices. Such a subject may or may not be physically addicted to nicotine and/or psychologically addicted to consuming nicotine products. Typical subjects in need of smoking cessation treatment smoke or use tobacco or other nicotine products daily, such as smoking at least 1 cigarette a day, or more, such as at least about 5, at least about 10, at least about 15, at least about 20, or more, cigarettes per day, including fewer than 10, 10-20, 20-30, 30-40, or 40 or more (or the equivalent use of other tobacco or nicotine products).

In some embodiments, a therapeutically effective amount of a nicotine-degrading enzyme variant is an amount effective to reduce plasma levels of nicotine, to reduce levels of nicotine localized in the brain, or both.

Nicotine exerts many of its significant effects after it crosses the blood brain barrier. In some embodiments, the methods and uses described herein reduce or prevent nicotine from crossing the blood-brain-barrier. Thus, in some embodiments, administration of a nicotine-degrading enzyme variant as described herein degrades nicotine circulating in the bloodstream of the subject, thereby reducing or preventing the nicotine from crossing the blood-brain-barrier. Thus, in some embodiments, the methods described herein reduce or prevent the physiological and psychological effects of nicotine that originate in the brain. Because the subject will experience a lessening or cessation of these effects, he/she will lose the desire to consume nicotine products. Additionally or alternatively, the disclosed nicotine-degrading enzyme variants may exert an effect by affecting the ability of nicotine to stimulate the peripheral nervous system.

The specific amount of a nicotine-degrading enzyme that is administered may depend on one or more of the age and/or weight of the subject, the amount of nicotine routinely consumed (e.g., smoked, chewed. or inhaled), and/or the level of nicotine in the subject's brain or plasma at the time of treatment. In some embodiments, a variant is administered at a dose of from about 0.01 to about 20 mg/kg, about 0.1 mg/kg to about 18 mg/kg, about 1 mg/kg to about 16 mg/kg, about 2 mg/kg to about 14 mg/kg, or about 5 mg/kg to about 10 mg/kg. In some embodiments, a variant is administered at a dose of about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8/5 mg/kg, about 9 mg/kg, about 9.5 mg/kg, about 10 mg/kg, about 10.5 mg/kg, about 12 mg/kg, about 12.5 mg/kg, about 13 mg/kg, about 13.5 mg/kg, about 14 mg/kg, about 14.5 mg/kg, about 15 mg/kg, about 15.5 mg/kg, about 16 mg/kg, about 16.5 mg/kg, about 17 mg/kg, about 17.5 mg/kg, about 18 mg/kg, about 18.5 mg/kg, about 19 mg/kg, about 19.5 mg/kg, or about 20 mg/kg. In some embodiments, a variant is administered at a dose of about 0.5 mg, about 1 mg, about 2.5 mg, about 5 mg, about 10 mg, about 15 mg, about 20 mg, about 25 mg, about 50 mg, about 75 mg, about 100 mg, about 150 mg, about 200 mg, about 250 mg, about 300 mg, about 350 mg, about 400 mg, about 450 mg, about 500 mg, about 550 mg, about 600, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100, about 2150 mg, about 2200 mg, about 2250 mg, about 2300 mg, about 2350 mg, about 2400 mg, about 2450 mg, or about 2500 mg. When more than one variant is administered, the total amount of variants administered may be in accordance with the foregoing guidance.

In some embodiments, the methods comprise administering a single dose of a nicotine-degrading enzyme variant(s) (or composition comprising the same). In some embodiments, the method comprises administering repeated doses, such as for a predetermined period of time of until the symptoms or effects of nicotine addiction are reduced, ameliorated, or eliminated or until the subject has ceased smoking or otherwise consuming nicotine. In some embodiments, treatment is repeated with additional doses of the variant(s) if signs/symptoms/effects persist or if the subject continues to have nicotine cravings or experiences them anew.

In some embodiments, the methods comprise administering a nicotine-degrading enzyme variant(s) (or composition comprising the same) three or more times a day, twice a day, or once a day. In some embodiments, the methods comprise administering a nicotine-degrading enzyme variant(s) (or composition comprising the same) once every other day, three times a week, twice a week, once a week, once every other week, once every three weeks, once a month, or less frequently. In such embodiments, the nicotine-degrading enzyme variant may be a long-acting nicotine-degrading enzyme variant as described above.

In some embodiments, treatment may continue for 1, 2, 3, 4, 5, 6, 7, 8, 9, 10, 11, 12, 13, 14, 15, 16, 17, 18, 19, 20, or 21 or more days; 1, 2, 3, 4, 5, 6, 7, 8, 9, 10, 11, 12, 13, 14, 15, 16, 17, or 18 or weeks months; or 1, 2, 3, 4, 5, 6, 7, 8, 9, 10, 11, or 12 or more months; or 1, 2, or 3 or more years or until the subject no long experiences nicotine cravings or other nicotine withdrawal symptoms, or has ceased smoking or using other tobacco products.

VI. Methods of Treating Nicotine Poisoning

The disclosed nicotine-degrading enzyme variants may be used to treat nicotine poisoning, nicotine overdose, or nicotine toxicity. For convenience, these methods are referred to herein collecting as treating nicotine poisoning. In some aspects, the methods of treating nicotine poisoning described herein comprise administering to a mammalian subject in need thereof a nicotine-degrading enzyme variant as disclosed herein, or a pharmaceutical composition comprising the same. In some embodiments, the methods comprise administering a nicotine-degrading enzyme variant to a subject that has ingested or consumed a toxic amount of nicotine. In some embodiments, the methods may comprise administering both a nicotine-degrading enzyme variant and another compound that is useful for treating nicotine poisoning, such as activated charcoal or another agent. In such embodiments, the enzyme variant and the second compound (e.g., activated charcoal) can be administered sequentially or simultaneously, from the same or different compositions. Thus, the treatment may include administering activated charcoal and/or other supportive treatments to address the symptoms and/or effects of nicotine poisoning.

In some embodiments, the therapeutically effective amount of the nicotine-degrading enzyme variant is effective to reduce, ameliorate, or eliminate one or more symptoms or effects of nicotine poisoning or overdose. The specific amount administered may depend on one or more of the age and/or weight of the subject, the amount of nicotine believed to have been ingested, and/or the subject's plasma level of nicotine at the time of treatment, and/or the subject's brain level of nicotine at the time of treatment. In some embodiments, the subject that is being treated for nicotine poisoning is an adult, while in some embodiments, the subject is a child (i.e., less than 19 years of age). In some embodiments, a therapeutically effective amount of a nicotine-degrading enzyme variant is an amount effective to reduce plasma levels of nicotine, and/or to reduce the amount of nicotine localized in specific tissues of the subject (e.g., brain/central nervous system, heart and vasculature, etc.). In specific embodiments, a therapeutically effective amount of a nicotine-degrading enzyme variant is an amount effective to reduce plasma levels of nicotine, to reduce levels of nicotine localized in the brain, or both.

The specific amount of a nicotine-degrading enzyme that is administered may depend on one or more of the age and/or weight of the subject, the amount of nicotine that was acutely consumed, and/or the level of nicotine in the subject's brain or plasma at the time of treatment. In some embodiments, a variant is administered at a dose of from about 0.01 to about 20 mg/kg, about 0.1 mg/kg to about 18 mg/kg, about 1 mg/kg to about 16 mg/kg, about 2 mg/kg to about 14 mg/kg, or about 5 mg/kg to about 10 mg/kg. In some embodiments, a variant is administered at a dose of about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8/5 mg/kg, about 9 mg/kg, about 9.5 mg/kg, about 10 mg/kg, about 10.5 mg/kg, about 12 mg/kg, about 12.5 mg/kg, about 13 mg/kg, about 13.5 mg/kg, about 14 mg/kg, about 14.5 mg/kg, about 15 mg/kg, about 15.5 mg/kg, about 16 mg/kg, about 16.5 mg/kg, about 17 mg/kg, about 17.5 mg/kg, about 18 mg/kg, about 18.5 mg/kg, about 19 mg/kg, about 19.5 mg/kg, or about 20 mg/kg. In some embodiments, a variant is administered at a dose of about 0.5 mg, about 1 mg, about 2.5 mg, about 5 mg, about 10 mg, about 15 mg, about 20 mg, about 25 mg, about 50 mg, about 75 mg, about 100 mg, about 150 mg, about 200 mg, about 250 mg, about 300 mg, about 350 mg, about 400 mg, about 450 mg, about 500 mg, about 550 mg, about 600, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, or about 2500 mg. When more than one variant is administered, the total amount of variants administered may be in accordance with the foregoing guidance.

Because nicotine poisoning is associated with vomiting, a non-oral route of administration may be used. Moreover, intravenous administration may be more effective than intraperitoneal administration. Thus, in some embodiments of methods of treating nicotine poisoning, a nicotine-degrading enzyme variant(s) (or composition comprising the same) is administered intravenously.

In some embodiments, the methods comprise administering a single dose of a nicotine-degrading enzyme variant(s) (or composition comprising the same). In some embodiments, the method comprises administering repeated doses, such as for a predetermined period of time or until the symptoms or effects of nicotine poisoning or toxicity are reduced, ameliorated, or eliminated or until the subject has ceased smoking or otherwise consuming nicotine. In some embodiments, treatment is repeated with additional doses of the variant(s) if signs/symptoms/effects persist.

In some embodiments, treatment may continue for one or more days following overdose, such as for 1-3 days, or 1-5 days, or for 1, 2, 3, 4, or 5 days following overdose. In some embodiments, treatment may continue until the subject no long experiences any symptoms of nicotine poisoning or toxicity or until the levels of nicotine in the subject's plasma and/or brain have decreased to a sufficiently safe level. In some embodiments, the nicotine-degrading enzyme variant may be a long-acting nicotine-degrading enzyme variant as described above.

One skilled in the art will readily appreciate that the present disclosure is well adapted to carry out the objects and obtain the ends and advantages mentioned, as well as those inherent therein. Modifications therein and other uses will occur to those skilled in the art. These modifications are encompassed within the spirit of the disclosure. The following examples are given to illustrate the present invention. It should be understood, however, that the invention is not limited to the specific conditions or details of these examples.

EXAMPLES

Example 1—Development and Testing of Nicotine-Degrading Enzyme Variants

3D Molecular Graphical Visualization

The NicA2 protein was visualized using Discovery Studio 4.5 (Dassault Systemes, BIOVIA Corp., San Diego CA) to determine active site residues. Based on inspection of the structure (PDB ID #5TTJ), location of FAD and reporting of putative critical active site residues, a presumed active site cavity was defined. All residues making up the exposed surface of this cavity, including both side chains and backbone atoms, were classified as active site residues: ARG9, PHE104, GLY105, GLY106, ALA107, TRP108, LEU217, TYR214, TYR218, GLU249, THR250, LYS340, PHE355, TRP364, GLN366, THR381, TRP417, ALA426, TRP427, ALA461, ASN462, ILE463.

Expression and Purification of NicA2

Wt NicA2 and variants were expressed with a C-terminal $His_6$-tag (SEQ ID NO: 38) from a pET-22b(+) (NOVAGEN) based expression plasmid transformed into E. coli BL21 (DE3). Purification was performed by Immobilized Metal Affinity Chromatography (IMAC) using Cobalt TALON™ His-Tag Purification Resin (CLONTECH) according to the manufacturer's protocol.

Primary Screening Assays

A synthetic gene (custom DNA synthesis by GeneArt/Invitrogen), codon optimized for E. coli expression of wild-type (wt) NicA2 amino acid sequence (GenBank accession number: AEJ14620.1) with a C-terminal $His_6$-tag (SEQ ID NO: 38) was cloned into the NdeI-XhoI sites of pET-22b(+) (Novagen), and the expression plasmid transformed into E. coli BL21(DE3). The predicted wild-type NicA2 amino acid sequence as expressed from this construct is shown in Table 1 (SEQ ID NO:1).

Figure 1:
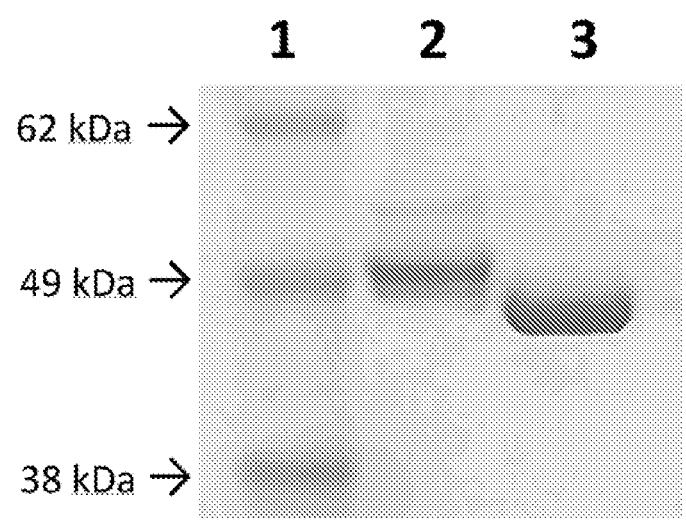

A heterogeneity in size was identified by SDS-PAGE of protein expressed from the construct encoding SEQ ID NO: 1 and purified by Immobilized Metal Affinity Chromatography (IMAC) using Cobalt TALON™ His-Tag Purification Resin (Clontech) according to the manufacturers protocol (FIG. 1; major and minor band around 49 kDa marker). As the protein was purified via the His-tag, the heterogeneity was inferred to be at the N-terminus. Utilizing the online search tool PRED-TAT (compgen.org/tools/PRED-TAT; Pantelis et al., *Combined prediction of Tat and Sec signal peptides with Hidden Markov Models,* 2010 BIOINFORMATICS), a putative TAT-leader sequence with an associated cleavage site following the alanine (A) residue at position 37 of SEQ ID NO:1 was identified.

In an effort to eliminate any non-essential bacterial sequence (including a specific in silico predicted T-cell epitope sequence at positions 16-24 of SEQ ID NO:1), to reduce immunogenic risk, as well as to eliminate the putative N-terminal cleavage site and the associated product heterogeneity, a deletion construct was made removing the first 50 N-terminal residues (NicA2Δ50; SEQ ID NO:2).

It was believed that this region could potentially be deleted without compromising catalytically activity; consequently NicA2Δ50 (SEQ ID NO: 2) was expressed in E. coli and purified as described above. As seen in FIG. 1, the purified NicA2Δ50 (SEQ ID NO: 2) appears homogeneous by SDS-PAGE analysis.

Analysis of enzymatic activity on purified protein was conducted using an Amplex Red assay (Reszka, et al., *Effects of peroxidase substrates on the Amplex red/peroxidase assay: Antioxidant properties of anthracyclines,* ANALYTICAL BIOCHEMISTRY 342: 327-337 (2005)). Briefly, the oxidation of nicotine by NicA2 results in generation of $H_2O_2$ which is coupled to the conversion of the colorless Amplex Red reagent into its red-fluorescent product, resorufin by HRP (horseradish peroxidase). The assay was performed essentially as recommended by the supplier of the assay kit (Thermo; Cat #A22188) with the exception of addition of S-Nicotine (Sigma) to a final assay concentration of 10 μM. Assays were run in a total volume of 100 μL/well in a black half-area flat bottom 96-well assay plate (Corning Cat #3993). Development of fluorescence was detected in a SpectraMax M2 multimode microplate plate reader (Molecular Devices) using the settings Ex at 555 nm; Em at 590 nm, employing a "Plate Blank" well to subtract values derived from a no enzyme control for each time point in the SoftMax Pro data evolution package (Molecular Devices). Activities were expressed as the relative slopes of increase in fluorescence plotted as a function of time compared to the wild-type NicA2 enzyme, which was run in parallel.

Figure 2:
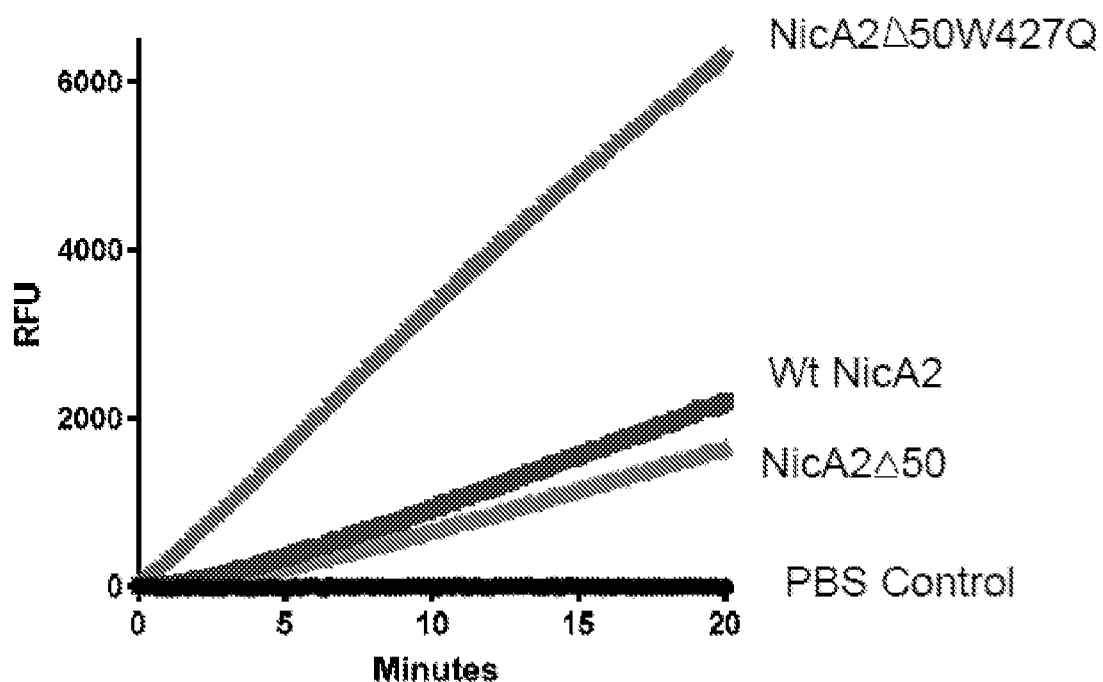

The Amplex Red assay revealed that the purified NicA2Δ50 protein showed a 23% reduction in activity relative to wild-type NicA2 (FIG. 2). Two shorter deletion constructs (NicA2Δ25 (SEQ ID NO:3) and NicA2Δ38 (SEQ ID NO:4) were generated and tested, but similarly showed decreases in activity compared to the wild-type enzyme. In summary, all three deletion mutants showed reduced activity relative to wild-type.

Thus, it was decided to design and identify NicA2 and NicA2Δ50 variants that would exhibit nicotine-degrading activity at least equivalent to the wild-type. A library of novel variants was prepared and tested according to methods shown in application PCT/US2018/016664, which is hereby incorporated by reference in its entirety. Screening of this library in the Amplex Red screening assay as described earlier lead to identification of improved variants with mutations at positions 104, 106, 107, 249, 355, and/or 426 (Table 3; SEQ ID NO's 5-28).

A custom Comprehensive Saturation Mutagenesis (CSM) library was supplied by Revolve Biotechnologies, Inc. (Firnberg et al., PLoS One, 7:e52031 (2012)), probing all single amino acid (aa) substitutions (one mutation per variant) in positions 104, 106, 107, 249, 355, and/or 426 of SEQ ID NO:1. These positions are a subset of positions constituting the active site of NicA2.

The library was transformed into BL21 Gold(DE3) (Agilent Technologies), and single colonies picked and grown overnight in a 96-well plate in LB media containing Carbenicillin (100 µg/ml). Overnight LB cultures were diluted into a new 96-well deep well plate containing 475 µl of auto-inducing Magic Media (Invitrogen)+Carbenicillin (100 µg/ml) and grown for 18 h at room temperature with vigorous shaking. Bacteria were harvested in the plate by centrifugation at 4000 rpm for 15 minutes, and pellets frozen at −80° C. Pellets were lysed by dissolving in 100 µl of room temperature Bug Buster HT Reagent (Novagen) containing 1 KU of r-Lysozyme (Novagen) per 1 ml and incubating on a shaking platform for 20 min at room temperature. Cleared lysates were prepared by diluting 1:1 (vol.:vol.) with Bug Buster HT Reagent and removing insoluble cell debris by centrifugation at 4400 rpm for 20 min at 4° C. 25 µl of cleared lysates were transferred to a new 96 well plate and diluted 1:1 (vol.:vol.) in 2% milk in PBS. Diluted lysates were transferred to the assay plate (black 96-well half area high binding plate (Corning) coated o/n at 4° C. with 5 µg/ml of anti-His Tag antibody (R&D Systems) in PBS; 50 µl per well; then blocked with 4% milk (in PBS) for 2 h at RT) and incubated at room temperature gently shaking for 3 h to ensure saturation of the immobilized anti-His mAb with the molar excess of expressed His-tagged enzyme. This step essentially results in normalizing any differences in concentration afforded by differences in growth, induction conditions, intrinsic expression levels, etc., and ensures a consistent amount of enzyme is assayed for activity in each well in the subsequent steps. This also ablates the need for quantification of enzyme in individual wells to precisely measure and compare relative activity of variants. Plate was washed 6× with PBST (PBS+0.1% Tween-20) and 1× with Amplex Red Reagent Buffer (Thermo) to remove unbound material. Enzyme assay was conducted by adding 50 µl of Amplex Red Solution (Thermo) including 10 µM S-Nicotine to each well and monitoring development of fluorescence over time.

Clones with assay activities enhanced compared to values from included colonies expressing wild-type NicA2 were isolated from the master plate with overnight LB culture, and 8 individual random colonies re-grown and rescreened in the Amplex Red assay as described above). Plasmid DNA was prepared and sequenced for identification of the mutation(s) leading to increased activity. A list of the activities of the identified variants in the Amplex Red assay (average for 8 individual colonies of each variant re-assayed as described above) is shown in Table 3. Sequences of these variants are disclosed in Table 1.

TABLE 3

Relative Activities of NicA2 Variants (purified proteins)

| Variant | Activity in Amplex Red assay (rel. to wt NicA2) |
|---|---|
| Wt NicA2 (SEQ ID NO: 1) | 100% |
| NicA2Δ50 (SEQ ID NO: 2) | 68% |
| NicA2F104R (SEQ ID NO: 5) | 635% |
| NicA2F104K (SEQ ID NO: 6) | 593% |
| NicA2F104I (SEQ ID NO: 7) | 378% |
| NicA2F104L (SEQ ID NO: 8) | 354% |
| NicA2F104S (SEQ ID NO: 9) | 320% |
| NicA2F104T (SEQ ID NO: 10) | 231% |
| NicA2G106S (SEQ ID NO: 11) | 385% |
| NicA2G106A (SEQ ID NO: 12) | 376% |
| NicA2A107R (SEQ ID NO: 13) | 1900% |
| NicA2Δ50A107R (SEQ ID NO: 14) | 1730% |
| NicA2A107K (SEQ ID NO: 36) | 670% |
| NicA2A107T (SEQ ID NO: 15) | 590% |
| NicA2A107G (SEQ ID NO: 16) | 490% |
| NicA2A107H (SEQ ID NO: 17) | 480% |
| NicA2A107P (SEQ ID NO: 18) | 350% |
| NicA2E249W (SEQ ID NO: 19) | 554% |
| NicA2E249D (SEQ ID NO: 20) | 273% |
| NicA2F355H (SEQ ID NO: 21) | 1344% |
| NicA2F355K (SEQ ID NO: 22) | 460% |
| NicA2F355E (SEQ ID NO: 23) | 146% |
| NicA2F355C (SEQ ID NO: 37) | 260% |
| NicA2A426Q (SEQ ID NO: 24) | 518% |
| NicA2A426W (SEQ ID NO: 25) | 487% |
| NicA2A426P (SEQ ID NO: 26) | 186% |
| NicA2A426C (SEQ ID NO: 27) | 160% |
| NicA2Δ50F104I; A107R (SEQ ID NO: 28) | 2422% |

As shown in Table 3, all these exemplary mutations provided activity enhancement in the full-length enzyme. Correspondingly, the high activity of the NicA2A107R variant (SEQ ID NO: 13) was retained in the NicA2Δ50A107R variant (SEQ ID NO: 14). Consequently, it is expected that all mutations listed in Table 3 will improve activity in the context of both full-length NicA2 and a deletion variant such as NicA2Δ50, NicA2Δ25, NicA2Δ38, or any similar deletion up to and including at least the first 50 N-terminal residues of NicA2, or any N- or C-terminal deletion variant provided this has an enzymatic activity of at least 20% of full-length wt NicA2.

Specific variants carrying mutations in multiple residues chosen from Table 3 can be generated by site-specific mutagenesis, and libraries consisting of multiple mutations in multiple positions chosen from Table 3 can be generated and screened as described above. These efforts could allow for the identification of variants with mutations in several positions in the same molecule with enzymatic activities higher than any of the individual single mutations listed in Table 3.

A combinatorial library was generated including the following single mutations shown to provide enhanced catalytic activity in serum at low nicotine concentration (see Table 3):
F104R,S,I,T
G106A
A107R,T,G (as subset of codons encoded by NNK)
F355H The mutations were introduced into a pETNicA2Δ50 expression construct (producing variants with an N-terminal deletion of the first 50 amino acids; see Table 1, SEQ ID NO. 2) by overlap PCR using the following oligos (all 3 degenerate oligos encode G106G/A and A107NNK):

```
Combi-1:
                            (wt F104; SEQ ID NO: 29)
5'-GCAGGTCAAGAAATTGAATTTGGTGSCNNKTGGGTTCATTGGTTACA
GC-3'

Combi-2:
                            (F104R; SEQ ID NO: 30)
5'-GCAGGTCAAGAAATTGAACGTGGTGSCNNKTGGGTTCATTGGTTACA
GC-3'

Combi-3:
                            (F104TSI; SEQ ID NO: 31)
5'-GCAGGTCAAGAAATTGAAABCGGTGSCNNKTGGGTTCATTGGTTACA
GC-3'
```

By mixing the purified PCR fragments containing the mutations for the overlap PCR in ratio 1:1:3, equal representation of the 5 codons in position F104 was obtained. The product of the overlap PCR fragment was cloned into two different vector fragments, one encoding the NicA2Δ50 wt sequence, one the NicA2Δ50F355H mutation. The final library was obtained by combining an equal number of transformants in BL21 Gold(DE3) from these two ligations. The library was screened in the Amplex Red primary assay as described in Example 1, using NicA2Δ50A107R as reference on the screening plates. Sequencing of hits revealed the NicA2Δ50F104I, A107R as a variant containing two mutations, with an activity better than either single mutation by itself, i.e., 1.4-fold increased over NicA2Δ50A107R (Table 3). The Δ50 N-terminal deletion removes a potential immunogenic region of the NicA2 enzyme, while only causing a modest decrease in activity (Table 3).

Having shown with the variants having SEQ ID NOs 2-4 that it is possible to delete the first epitope with only moderate effect on activity, the data provided in Table 3 shows that this decrease in activity could be mitigated or overcome by mutations listed in Table 3.

Variants based on mutations in four other epitopes set forth in Table 2 were prepared and assessed as described above for Epitope B, Epitope 2, Epitope 3, and Epitope 4. As seen in FIGS. 4A-E, 2, 4, and 7 variants were identified with assay values >=90% of the activity of the wild-type NicA2 enzyme from Epitope B, 2, and 3, respectively, indicating that these variants (L74N & Y77R, R78Q, V304A & M306Q, V394A, V304T & M306I, M306I & L310R, L374Q & I377S, L374A & I377A; L374N & I382Q, I377A & I382T, I377T & I382T, I377T, and L374N & A383Q; see FIG. 4) have enzymatic activity similar to wild-type, and, based on in silico predictions, are predicted to have lower immunogenic potential. Interestingly, none of the variants proposed for Epitope 4 showed more than 40% activity compared to wt NicA2 (see FIG. 4D). The mutations identified in this Example (one mutation from each epitope) can be introduced into the NicA2 backbone, or combined with any of the other identified single mutation variants described in Table 3, or any number of mutations resulting from combination of mutations, to produce a single de-immunized enzyme variant with enzymatic activity equal to or better than wt NicA2.

Example 2—Identifying NicA2 MHCII Epitopes

An in silico search of NicA2 MHCII epitopes was performed based on the 8 most common HLA-DR alleles (Cantoret et al., *PNAS* 108: 1272-1277 (2011); DRB1*0101, DRB1*1501, DRB1*1301, DRB1*1101, DRB1*0801, DRB1*0701, DRB1*0401, and DRB1*0301). The search was done using the immune epitope database (Vita et al., *Nucleic acids research,* 43: D405-D412 (2015)) and percentile consensus rank method to assess the predicted immunogenic potential of NicA2. The percentile consensus score for each overlapping 15-mer NicA2 peptide was averaged across all the 8 HLA-DR alleles. The immunogenic potential of NicA2 was then determined by selecting all NicA2 sequences that were >1 standard deviation in tighter predicted binding to MHCII as compared to the overall averaged binding score. This method revealed eight contiguous sequences across 45% of the NicA2 sequence reflective of residues 10-32, 68-94, 189-225, 248-285, 296-327, 336-391 and 435-459 of SEQ ID NO:1 (highlighted in grey in Table 1) that are predicted to be broadly immunogenic.

A more narrow search using only the DRB1*0401 allele was performed in silico. This search yielded the six highest ranked immunogenic T-cell epitopes underlined in SEQ ID NO:1 of Table 1.

Example 3—PEGylation of Nicotine-Degrading Enzymes

PEGylation of NicA2

Random PEGylation of wt NicA2 was performed at a protein concentration of 5 mg/mL and using 10 or 20 kDa NHS-PEG reagent (SUNBRIGHT® ME-100TS or ME-200TS; NOF America Corporation) at 7- or 20-fold molar excess in 100 mM $Na_3PO_4$, pH 7.6 on ice for ≥2 h. Elimination of unconjugated PEG reagent was performed using Amicon Ultra-15 centrifugal filter units with a 50 kDa cutoff. Samples corresponding to 2 μg protein were analyzed on SDS-PAGE gels run in MOPS running buffer and stained using SimplyBlue SafeStain (Invitrogen).

Analysis of PEGylated NicA2

Experiments were undertaken to develop protocols for conjugating polyethylene glycol (PEG) to NicA2 and other nicotine-degrading enzymes, such as the disclosed variants, and to determine the effect of PEGylation on activity and half-life.

Figure 5:
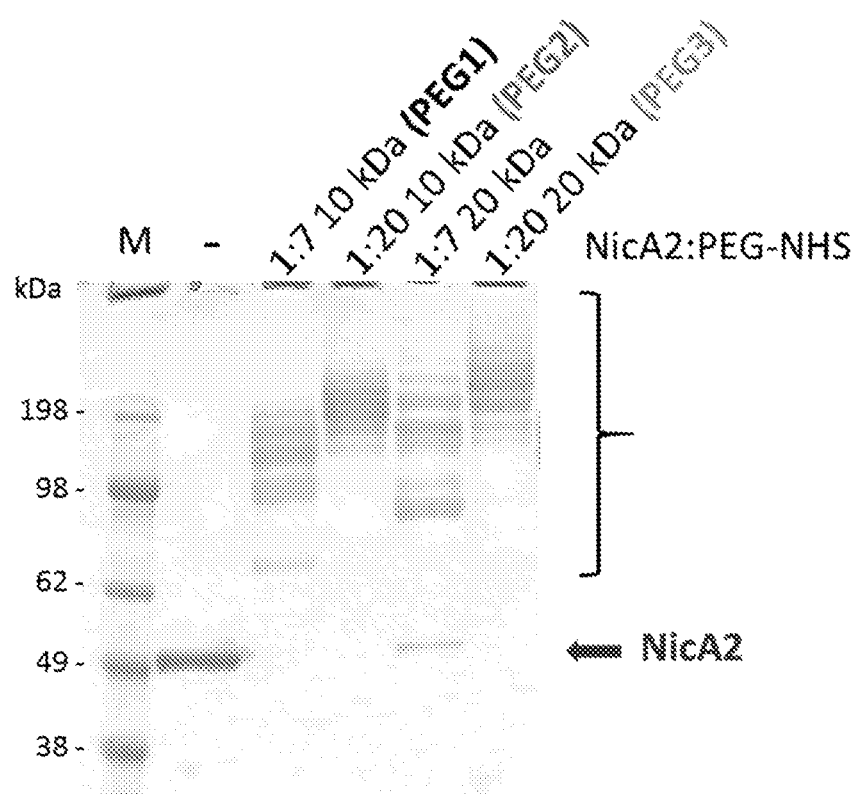
FIG. 5 shows random PEGylation of NicA2 using SDS-PAGE analysis. These results indicate that PEGylation can be increased by an increase in molar excess of PEGylation reagent and PEG chain length.

SDS-PAGE analysis indicated that the degree of PEGylation increases as the molar excess of PEGylation reagent and PEG chain length increases. Random PEGylation of wild-type (wt) NicA2 was performed at a protein concentration of 5 mg/mL and using 10 or 20 kDa NHS-PEG reagent (SUNBRIGHT® ME-100TS or ME-200TS; NOF America Corporation) at 7- or 20-fold molar excess in 100 mM $Na_3PO_4$, pH 7.6 on ice for ≥2 hours. Elimination of unconjugated PEG reagent was performed using Amicon Ultra-15 centrifugal filter units with a 50 kDa cutoff. Samples corresponding to 2 μg protein were loaded on an SDS-PAGE gel run in MOPS running buffer, and stained using SimplyBlue SafeStain (Invitrogen). As seen in FIG. 5, the degree of PEGylation could be controlled by controlling the excess molar ratios of PEGylation reagent. Preparations NicA2-PEG1, -PEG2, and -PEG3 where no residual unconjugated protein was detected by SDS-PAGE were chosen for further analysis.

Figure 6:
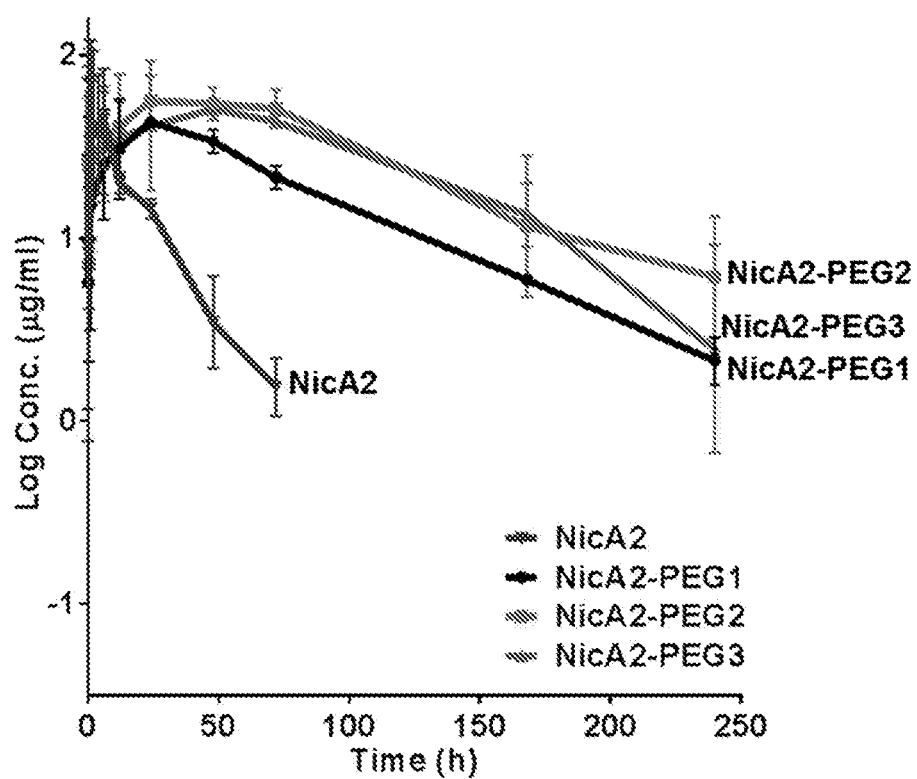
FIG. 6 shows PEGylation enhances the pharmacokinetic (PK) properties of NicA2 in the serum of animals administered PEGylated NicA2.

In order to determine whether PEGylation could enhance the pharmacokinetic (PK) properties of NicA2, serum concentrations were determined as a function of time after intravenous (i.v.) dosing in rats (5 mg/mL; N=4; 2M+2F). The data from these experiments are shown in FIG. 6. Briefly, MaxiSorp ELISA plates (Nunc) were coated overnight with anti-His tag antibody (R&D Systems), which could bind to the C-terminal His-tag on the NicA2 and PEGylated NicA2 proteins. Plates were blocked with 1% non-fat dry milk (NFDM) in phosphate buffered saline (PBS) for approximately 1 hour. Dilutions of NicA2 and NicA2-PEG1-3 standards and serum samples in 1% NFDM in PBS+0.1% Tween-20 were added to the plates and incubated for 2 hours at room temperature. After washing away unbound substances (all wash steps performed in PBS+0.1% Tween-20), rabbit anti-NicA2 polyclonal primary detection antibody was added to the wells for a 1 hour incubation. A wash step was followed by addition of horseradish peroxidase (HRP)-conjugated goat anti-rabbit IgG (Fc) (KPL International). Plates were washed, and the remaining binding complex was detected with TMB substrate (3,3',5,5'-tetramethylbenzidine; KPL International). Once stopped with acid, plates were read on a spectrophotometer at 450 nm and data analyzed in SoftMax® Pro, version 5.4 (Molecular Devices).

Figure 7:
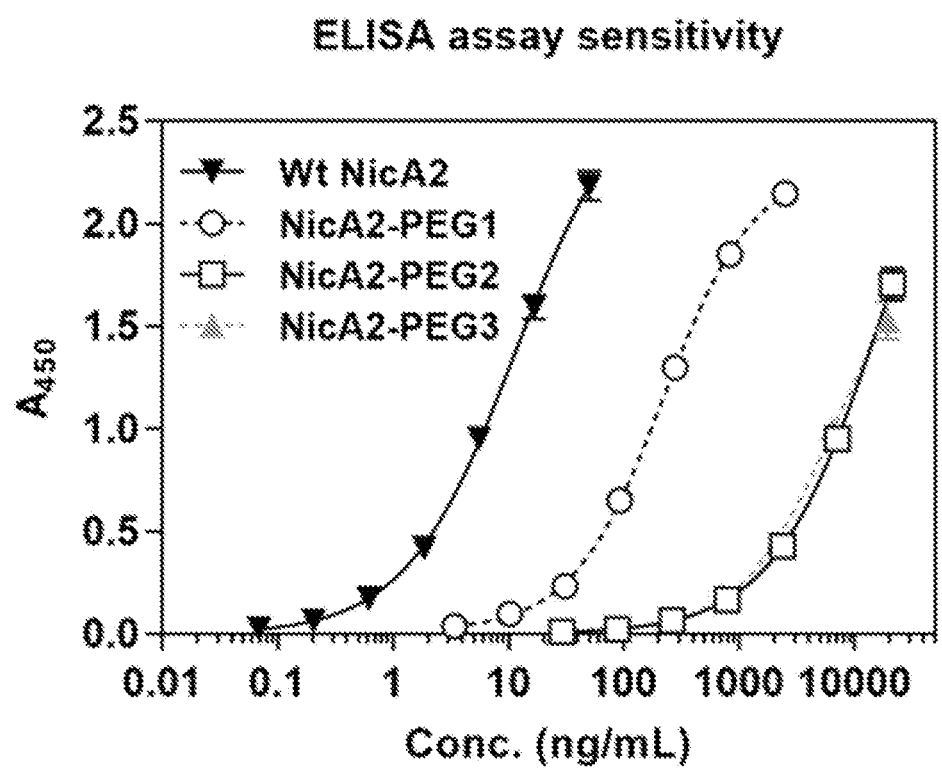
FIG. 7 shows PEGylation can mask potentially immunogenic epitopes on NicA2, using detection of unconjugated NicA2 or various preparations of PEGylated NicA2 in a sandwich ELISA format.

Additional experiments were performed to determine whether PEGylation masks epitopes on NicA2. Serial dilutions in PBS of unPEGylated or PEGylated preparations of NicA2 were tested in the same sandwich ELISA assay used for measurement of serum concentrations in the PK experiment described above (FIG. 6), and signal (A450) plotted as a function of concentration. Assay sensitivity is dramatically reduced with increasing degree of PEGylation (approx. 1000-fold higher concentration of NicA2-PEG2 and -PEG3 required to obtain an A450 of 1.0 relative to unPEGylated molecule), indicating that epitopes recognized by the detection antibody reagents are less accessible in the PEGylated molecules. These results are shown in FIG. 7.

PEGylation was shown to decrease titers of NicA2-specific antibodies in a transgenic HLA-DR4 mouse model of immunogenicity. In particular, the reduction of NicA2-specific antibody titers 10 days after subcutaneous (s.c.) injection in Freunds Incomplete Adjuvant in human DR4 transgenic mice (N=6; 3M+3F; Taconic Biosciences) was studied. This mouse model carries a hybrid MHC class II molecule with the antigen binding domains of human HLA-DRA and HLA-DRB*0401 (representative of the DR4 supertype) and does not express endogenous mouse MHC class II molecules. Titer was defined as serum dilution to achieve OD450=0.5 in ELISA using NicA2 coated plates, and detection by goat α-mouse IgG-γ-HRP. The lowest serum dilution tested was 50-fold (Limit Of Detection (LOD); indicated by a dashed line in FIG. 8). PEGylation of NicA2 led to a significant ≥10-fold decrease in average NicA2-specific antibody titers in transgenic DR4 mice (FIGS. 8; 4, 2, and 2, animals from groups NicA2-PEG1, -PEG2, and -PEG3, respectively, had titers below LOD), indicating that PEGylated variants may exhibit lower immuogenicity in a clinical setting.

It was also observed that PEGylation attenuates the human T-cell proliferation response and cytokine TNFγ release mediated by exposure to NicA2, as shown in FIG. 9. PEGylation of NicA2 led to a significant decrease in average T Cell proliferation Stimulation Index (FIG. 9, left panel) as well as decrease in IFNγ secretion levels (FIG. 9, right panel) (Independent experiments from five healthy volunteers). Positive control: phytohaemagglutinin (PHA). Test results for five independent experiments are shown for T cell proliferation response stimulation indexes (SI; measured by 3H-Thymidine uptake) (left) and fold increase in IFNγ secretion levels (measured by flow cytometry and a Cytometric Bead Array kit (BD Biosciences)) (right) for NicA2 and NicA2-PEG2 at three test concentrations in comparison to baseline responses (PBMC). An increase of 3≥(dashed line) is considered a significant increase and a positive response.

It also was shown that PEGylated enzymes retained full nicotine degrading activity in serum, as shown in FIG. 10. Wt NicA2 or NicA2-PEG2 was added to a final concentration of 0.075 mg/ml into rat serum containing 40 ng/mL S-nicotine (250 nM, which is equivalent to plasma levels observed in a typical smoker) pre-incubated at 37° C. Samples were withdrawn at various time points, and enzymatic activity immediately quenched by addition of methanol and rapid mixing. Residual nicotine concentrations were determined by gas chromatography (GC). LOD of the GC assay was 2 ng/mL indicated by the dashed line. PEGylation did not appear to impede NicA2's ability to degrade nicotine.

Example 4—Nicotine Degrading Activity in Serum

To investigate whether activity was improved not only in assay buffer and at the high (10 μM) nicotine concentration of the Amplex Red assay (see Table 3), but also in serum using nicotine concentrations more relevant to those encountered in a typical smoker, exemplary variants improved in the Amplex Red assay were purified and assessed in an assay utilizing serum rather than a buffer solution. Purification by Immobilized Metal Affinity Chromatography (IMAC) was performed using Cobalt TALON™ His-Tag Purification Resin (Clontech) according to the manufacturer's protocol, and concentration after dialysis into PBS was calculated based on the absorbance at 280 nm and the theoretical extinction coefficient of each variant.

Purified enzyme was added to a final concentration of 1.5 μg/ml into rat serum containing 40 ng/ml of S-(−)-nicotine (250 nM, which is equivalent to plasma levels observed in a typical smoker) pre-incubated at 37° C. Samples were withdrawn at various time points, and enzymatic activity immediately quenched by addition of methanol and rapid mixing. Residual nicotine concentrations were determined by gas chromatography (G C; Hieda et al.: *Immunization of rats reduces nicotine distribution to brain*, Psychopharmacology, 143: 150-157 (1999)). Level of detection of the GC assay was 2 ng/mL. As seen in FIGS. 11A and 11B, variants NicA2A107R (positive control disclosed in PCT/US2018/016664), A107T, A107G, F104T, F104I, F104R, F104S, G106A, F355H, and A426C have increased nicotine degrading activity under these conditions compared to wt NicA2. In contrast, variant E249W does not appear to have improved nicotine degrading activity in this assay, even though activity at a substrate concentration of 10 μM in the Amplex Red assay was 5.5-fold increased over wt (Table 3).

While not being bound by theory, it is believed that at 10 μM the effects on Vmax (and kcat) are being observed, and the reason why higher activity seen in the Amplex Red assay does not always translate to corresponding results observed with low nicotine concentrations (<=250 nM) is that the mutations may negatively impact Km (i.e., increase Km) so the rate at low substrate concentrations ends up lower or similar to that observed for wt NicA2. However, this is simply a hypothesis based on the observations made to date, and further studies may show that activity in the Amplex Red assay will generally tend to predict activity in serum degradation activity as well.

Example 5—Secondary Enzyme Screening Assays

Nicotine biosensor assay: The experiments were conducted using a BiOptix 404pi enhanced SPR instrument. Nicotine-specific mAb, ATI-1119, an IgG1 with a suitable $K_D$ in the middle of the concentration range to be measured (66 nM for S-(-)-nicotine) was immobilized on a BiOptix CMD200m sensor chip using standard EDC/NHS amine coupling with blocking of the remaining active esters with ethanolamine. For standard curves, S-(-)-nicotine was injected at different concentrations (3× serial dilutions) in running buffer (10 mM HEPES (pH 7.4), 150 mM NaCl, 3 mM EDTA, 0.05% Tween-20). Each injection was followed by buffer flow at 25° C. for 20 min to dissociate nicotine from the mAb and prepare the chip for the next sample injection. Three (3) independent randomized injections were conducted for each nicotine concentration. Response units at steady state was determined using the Scrubber2 software.

For the assay of enzyme activity, crude lysates were prepared as described for the primary screening assay. Enzyme was captured from lysates using immobilized anti-His tag mAb (one well per assay point). After washing off unbound material, the assay was started by adding 100 µl running buffer with a starting nicotine concentration of 250 nM to mimic the blood concentration encountered in a typical smoker (40 ng/mL). Reactions were stopped by transferring 90 µl into prelabelled PCR-tubes and heated to 90° C./10 min to inactivate potential residual enzyme activity. Samples were transferred to a 96 well sample plate, which was subsequently loaded into the autosampler (kept at 10° C.) of the BiOptix instrument.

Results

Figure 12A:
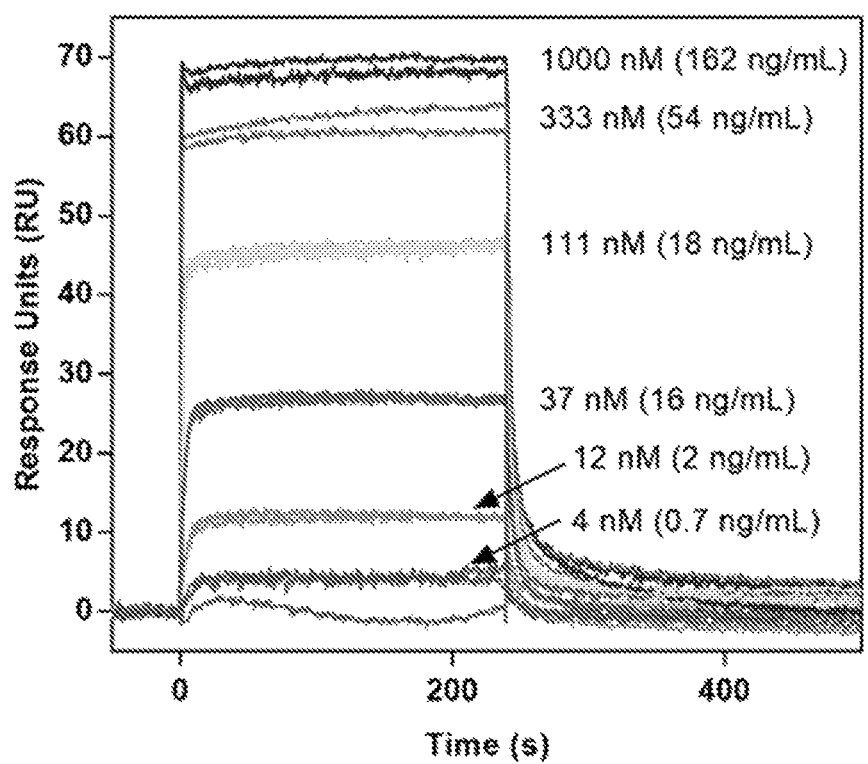
Figure 12B:
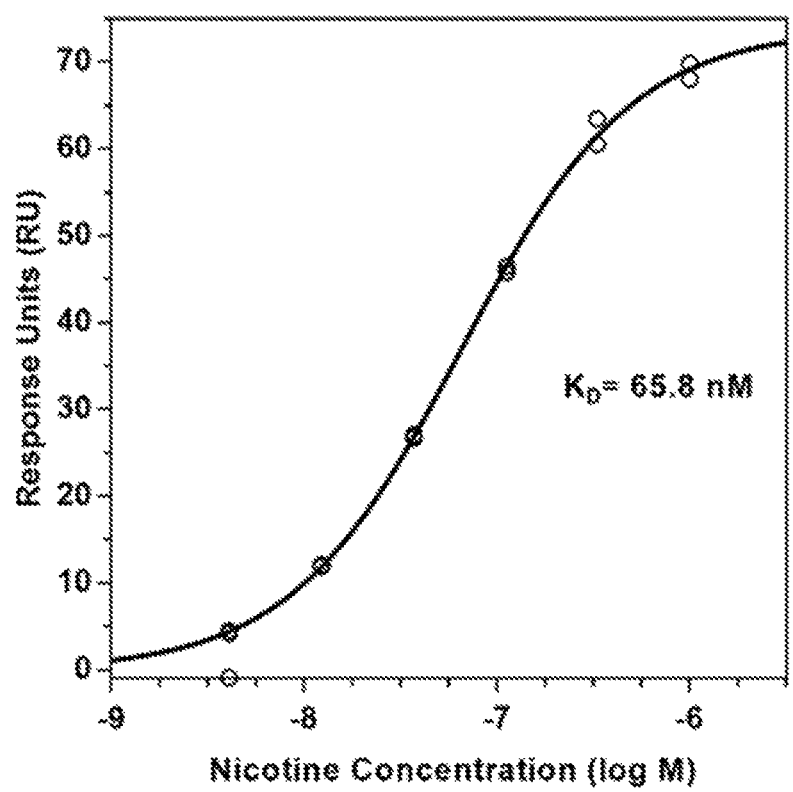

With a total of 58 individual variants with enhanced activity at 10 µM substrate (a concentration 100-fold over the published Km for wt NicA2; reflecting an enhanced kcat over wt), a novel secondary screening assay was designed to efficiently identify those variants that also had improved activity at the lower nicotine concentrations encountered in the blood of a smoker (e.g., 250 nM; a typical daily maximum). An automated nicotine biosensor assay that enabled efficient and accurate screening of variants without requiring full purification and quantification was implemented as described here briefly. As shown in FIGS. 12A and 12B, using Surface Plasmon Resonance (SPR), a nicotine-specific mAb immobilized on a sensor chip can give response curves where the SPR signal (expressed in response units, RU) at steady-state is proportional to the nicotine concentration in the buffer passed over the chip surface. This assay allowed for quantitation of unknown nicotine levels in buffer in a range of single digit nM to 1 µM for this particular antibody (ATI-1119) with a KD for S-(-)-nicotine of 66 nM. Briefly, FIG. 12A shows a sensorgram of 3-fold serial dilution of S-(-)-nicotine in running buffer passed over a sensor surface with immobilized anti-nicotine antibody over a range of nicotine concentrations (as indicated, in triplicate). After a steady-state level of binding was achieved, running buffer without nicotine was passed over the chip (starting at t=240 sec) to dissociate nicotine from the mAb. FIG. 12B shows a plot of sensor Response Units (RU) at steady-state (from experiment in panel C) vs. S-(-)-nicotine concentration.

Figure 13A:
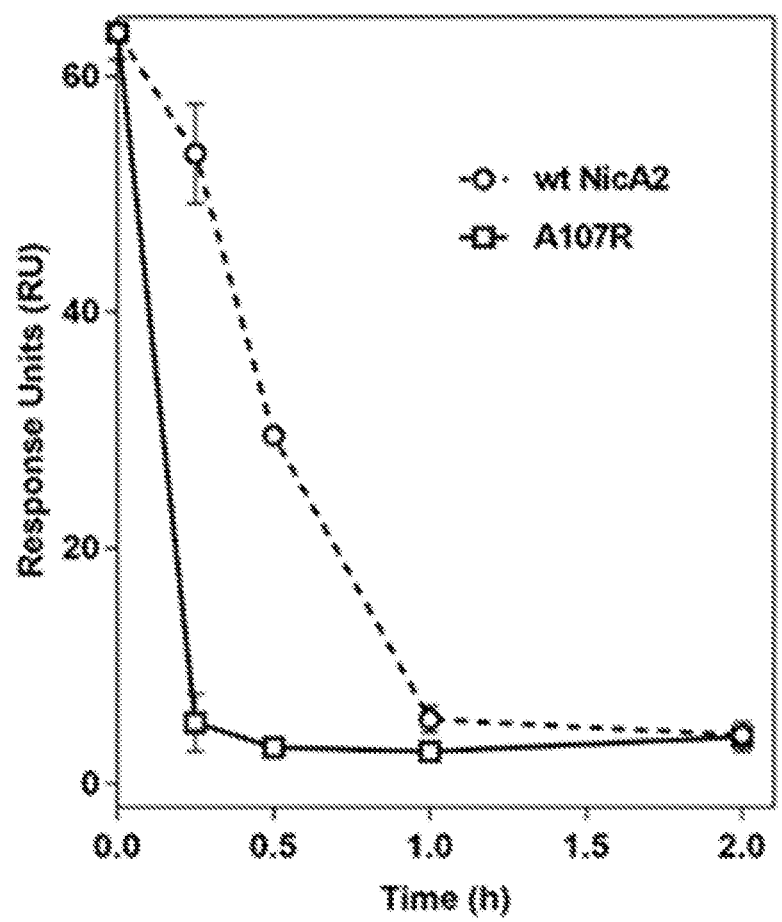
Figure 13B:
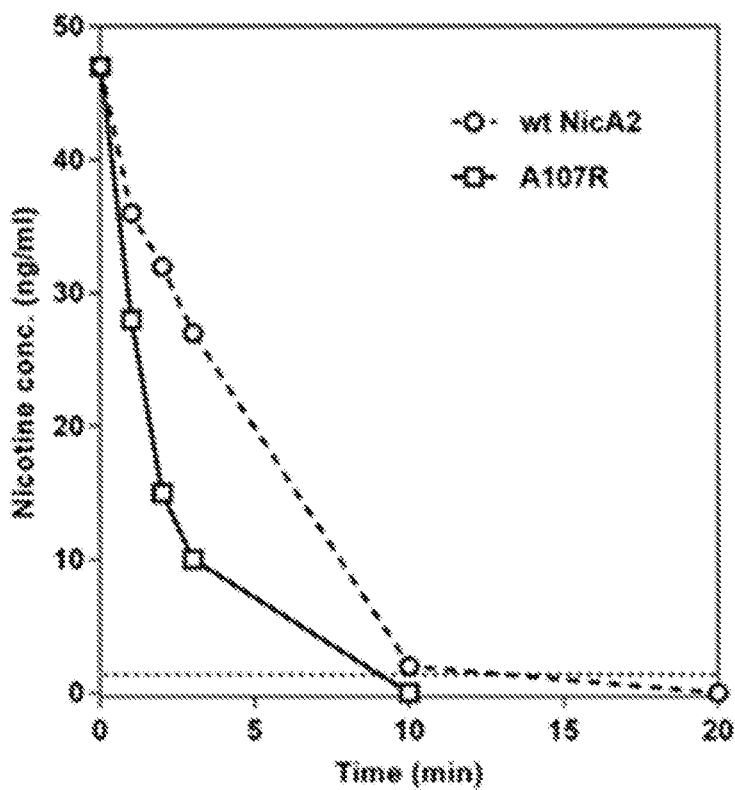
Figure 13C:
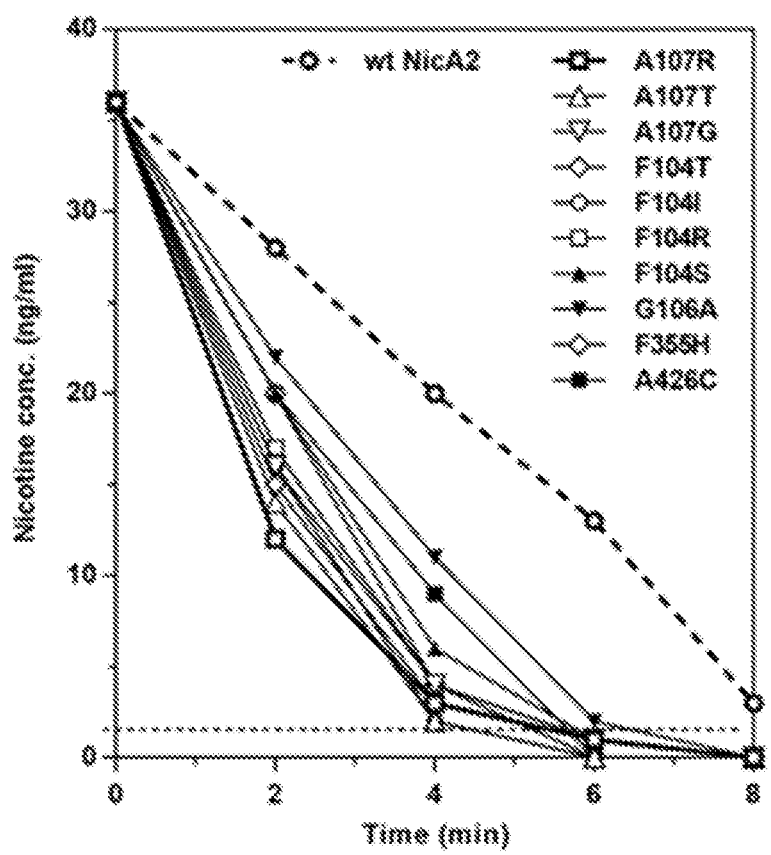

An assay was devised where residual nicotine concentrations could be measured as a function of incubation time with enzyme. Briefly, FIGS. 13A-C show the results of these secondary enzyme screening assays at nicotine concentrations found in smokers and the activity of purified enzyme variants. FIG. 13A shows His-tagged wt NicA2 enzyme (circles) or mutant NicA2A107R (squares) were captured from E. coli lysates by anti-His-tag mAb in assay wells. Buffer containing 250 nM S-nicotine was added, samples retrieved, and heat inactivated at the time points indicated. Samples were run on the biosensor instrument, and response units were plotted as a function of time. As seen in FIG. 13A, a decrease in RU over time was observed for lysates of wt NicA2. For lysate from the best variant in the primary screening assay, A107R, the rate of nicotine degradation was substantially faster than wt. To ensure the data would replicate using fully purified protein and in serum, wt and the improved variant's capacity to reduce nicotine concentrations in serum were compared using a highly-sensitive and quantitative Gas Chromatographic (GC) assay. The GC assay was only used in this final in vitro assay step since it is low-throughput and would have made it time-consuming to screen all initial hits. FIG. 13B shows purified enzyme or mutant NicA2A107R were added to rat serum containing 40 ng/mL S-(-)-nicotine, and samples were withdrawn and activity quenched by MeOH addition at the time points indicated. Residual nicotine concentration was measured by GC. As seen in FIG. 13B, the highest activity variant, NicA2A107R, has increased nicotine degrading activity compared to wt NicA2, in serum at nicotine concentrations found in smokers. This enhanced activity replicated and confirmed the biosensor assay results.

With the secondary assays implemented and validated, all variants with at least a 2-fold activity increase in the primary screening assay compared to wt NicA2 were tested at lower nicotine concentrations in the SPR assay, and variants F104T, I, R and S; G106A; A107R, T, G, F355H and A426C were found to be improved over wt. These were subsequently purified and tested in the serum/GC assay. FIG. 13C shows enhanced activity of 10 variants over wt NicA2 at 40 ng/mL nicotine in serum. Each purified variant (1.5 µg/mL) was added to rat serum containing 40 ng/mL nicotine at 37° C., and activity quenched with methanol at various time points. Open symbols indicate increased activity compared to wt of >3-fold in this assay. Nicotine concentrations were measured by GC. As shown in FIG. 13C, these variants were indeed improved in serum as well.

Simulations of the data in FIG. 13C (Table 2) suggest that at least for one variant (A107R) enhanced kcat comes at the expense of increased $K_M$ (the enzyme concentration needed to attain 50% of the maximum rate of catalysis, Vmax). As a validation of the kinetic modeling of low nicotine progress curves, we found wt NicA2 had an apparent kcat/$K_M$ of 6.4×10⁴ M-1 s-1 in close agreement with prior reports. The variants shown in FIG. 13C showed improved kcat/$K_M$ values ranging from 1.7-fold (G106A) to 3-fold higher (A107R) than wt NicA2 (Table 2). Simulation further suggested that compared to wt NicA2 only A107R displayed a significantly increased $K_M$ (830 nM), a value in close agreement with steady state kinetic analysis performed with this variant across a broad range of nicotine concentrations (data not shown).

TABLE 4

Results of GC Analysis

| Variant | $k_{cat}/K_M$ (M$^{-1}$s$^{-1}$) (apparent) | $k_{cat}$ (s$^{-1}$) (apparent) | $K_M$ (nM) (apparent) |
|---|---|---|---|
| wt NicA2 | $6.4 \times 10^4$ | 0.015 | 240 |
| A107R | $1.9 \times 10^5$ | 0.159 | 830 |
| A107T | $1.8 \times 10^5$ | 0.050 | 285 |
| A107G | $1.6 \times 10^5$ | 0.053 | 335 |
| F104T | $1.7 \times 10^5$ | 0.055 | 330 |
| F104I | $1.6 \times 10^5$ | 0.039 | 240 |
| F104R | $1.5 \times 10^5$ | 0.041 | 270 |
| F104S | $1.3 \times 10^5$ | 0.031 | 250 |
| G106A | $1.1 \times 10^5$ | 0.031 | 280 |
| F355H | $1.3 \times 10^5$ | 0.029 | 220 |
| A426C | $1.3 \times 10^5$ | 0.030 | 230 |

Apparent $k_{cat}/K_M$ values were calculated using the low nicotine assay results (FIG. 13C) using a form of the Michaelis-Menten equation ($v_{0[E]} = k_{cat}/K_M^*[S]$) and to construct progress curves that were fitted to a simple kinetic model (KinTek) to derive apparent $k_{cat}$ values. The resulting $k_{cat}/K_M$ and $k_{cat}$ values were used to calculate the apparent $K_M$ values.

Example 6—Improved In Vivo Activity of the A107R Mutant

Rat Nicotine Distribution Studies

Male and female Sprague Dawley rats weighing approximately 300 and 250 g, respectively, were purchased with jugular venous catheters in-place (Charles River Labs). Three groups of 8 rats (4 male+4 female per group) were pretreated with bovine serum albumin, wt NicA2, or NicA2Δ107R through the catheter at a dose of 0.625 mg/kg. A minimum of 5 min later each group received 0.03 mg/kg nicotine i.v. Rats were sacrificed at 3 min following the nicotine dose. Blood and brain samples were obtained by decapitation and quenching with methanol as previously described. Blood or brain nicotine concentrations were compared by one-way ANOVA with a Bonferroni correction for multiple comparisons.

Animal Husbandry

Equal numbers of age-matched male and female Sprague Dawley rats (Charles River Laboratories) or HLA transgenic mice per study group were used. Study animals with surgical modifications were housed individually in disposable microisolator cages (Innovive). Environmental controls were set to maintain the following conditions: a temperature range of 64 to 79° F., a relative humidity range of 30 to 70%, ten or greater air changes/hour, and a 12-hour light/12-hour dark cycle. Food and water were available ad libitum. Animal welfare followed the NIH guide for Care and Use of Laboratory Animals (8$^{th}$ ed.) and all protocols were approved by Noble Life Sciences (NLS) Institutional Animal Care and Use Committee. NLS is an AAALACi accredited and USDA Licensed (51-12-0092) and OLAW Assured (A4633-01) facility. Collection of blood from animals occurred while under isoflurane anesthesia and steps necessary to minimize animal suffering were undertaken. Study animals were euthanized after terminal blood collection by thoracotomy under isoflurane anesthesia consistent with AVMA Guidelines.

Results

Figure 14:
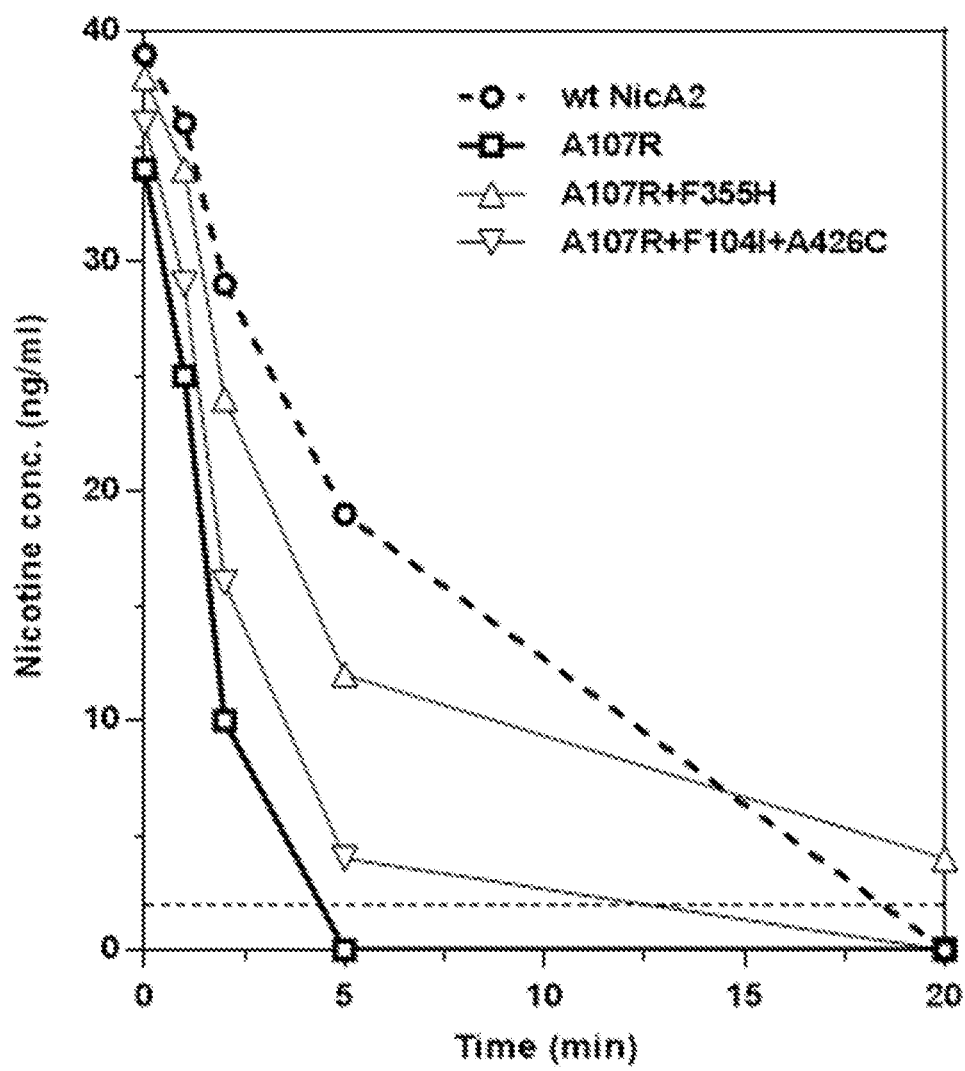
Figure 15:
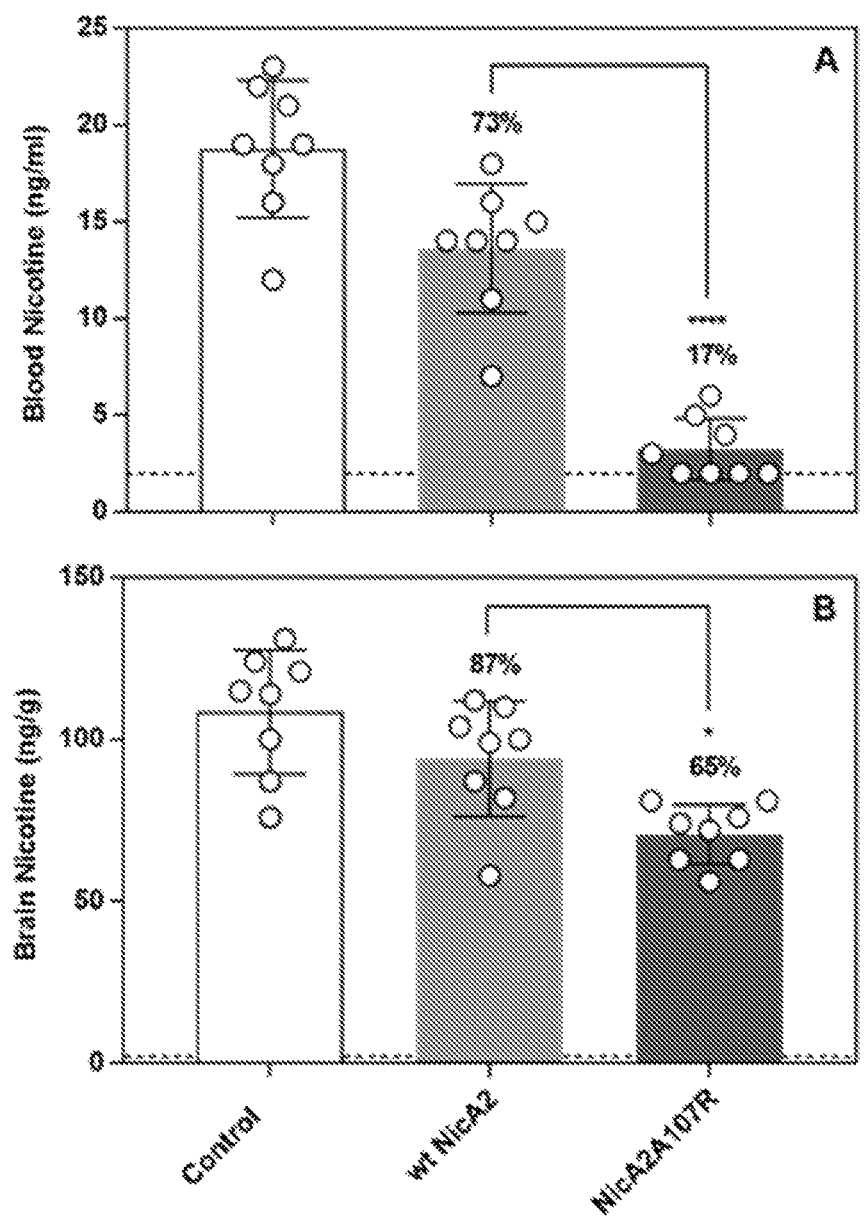

In order to ensure the enhanced in vitro efficacy shown in the previous assays translated to enhanced in vivo efficacy as well, the effects of dosing either wt NicA2 or NicA2A107R at 0.625 mg/kg on nicotine distribution to blood and brain were tested. Eight rats per group were pre-dosed with enzyme or bovine serum albumin (BSA; control), and 10 min later given a nicotine dose of 0.03 mg/kg by i.v. bolus injection delivered in under 10 s (a nicotine dose equivalent to 2 cigarettes in a human on a mg/kg basis). 3 min later, blood and brains were isolated, enzymatic activity was quenched immediately as previously described, and samples analyzed for nicotine content using gas chromatography (FIG. 14). NicA2A107R lowered nicotine blood concentrations to 3.25 f 1.5 ng/mL vs. 13.6 f 3.1 ng/mL for wt NicA2 (p<0.0001, one-way ANOVA with Bonferroni's correction comparing A107R to wt NicA2) or an 83% vs. 27% reduction, respectively, compared to controls (18.8 f 3.3 ng/mL). At the 0.625 mg/kg dose, brain nicotine levels were only partially reduced: 35% for NicA2A107R and 13% for wt NicA2 (p=0.02), as compared to a 95% reduction when 20 mg/kg wt NicA2 is dosed. These data suggest that NicA2Δ107R is approximately 3-fold more potent than wt NicA2 in vivo under these conditions.

The same serum-based analysis was carried out using combination variants including (i) a A107R mutation and a F355H mutation (SEQ ID NO: 34) and (ii) A107R, F104I, and A426C mutations (SEQ ID NO: 35). The results of this analysis are shown in FIG. 14.

Example 7—Pilot Chronic Toxicology Testing Indicates that NicA2 in the Presence of Nicotine is Well-Tolerated Toxicology Testing of NicA2 in the Presence of Nicotine The purpose of this study was to evaluate the repeat-dose tolerability of seven (7) fixed i.v. doses of 20 mg/kg NicA2-ABD (a long-acting form of NicA2 in which the enzyme is conjugated to an albumin binding domain (ABD)) dosed once every 4 days (140 mg/kg in total) in the presence of 1 mg/kg/day of nicotine given continuously by i.v. for 28 days using a rat model. This dose amount was selected since 20 mg/kg was sufficient to reduce brain nicotine levels by 95% in a rat nicotine-PK study and drug supply was limited.

Twenty (20) female and twenty (20) male Sprague Dawley rats (225-300 grams) were divided into two groups of sixteen (16) animals and one group of eight (8) animals. Animals were implanted with osmotic pumps delivering a continuous dose of nicotine or vehicle through the study period. NicA2-ABD (every four days) was delivered by intravenous injection. 16 animals received saline, 16 animals received nicotine only and only 8 animals received NicA2-ABD due to limited available drug supply.

All animals received the full dose (7×20 mg/kg i.v.) with no injection related behavioral changes, injection site reaction, and no mortality was induced in any of the animals. Daily clinical observations found no observable behavioral changes or modifications in feeding or grooming in any groups. Body weight was monitored twice weekly for the duration of the study and no significant differences between treatment groups were found. On Study day 28, blood was collected and analyzed for hematology, serum chemistry, and coagulation. Additional aliquots of blood plasma were taken for assaying blood levels of NicA2-ABD. After blood collection animals were placed under anesthesia with isoflurane and sacrificed by thoracotomy.

Assessment of toxicity was based on mortality, clinical observations, and body weight during the 28 day study; and at the end of study on organ weights, gross anatomic pathology, hematology, serum clinical chemistry, and coagulation.

At the end of the study animals were necropsied with no gross pathological finding noted in any animal. Major organs (liver, lung, spleen, heart, kidneys, testis or ovaries) were isolated and weighed. No gross pathological findings were noted in these tissues, and no statistically significant changes in organ weights were found (kidneys, testis, and ovaries weighted as a pair). Blood was collected, and complete blood count performed to determine any changes in hematological parameters. While occasional animals had values outside the normal range (e.g. slightly decreased lymphocytes or hemoglobin) no significant changes or trends were found in any group. There was a trend to have slight polychromasia in some of the control animals that received nicotine alone. Serum clinical chemistry of 23 different analytes and plasma coagulation measures did not find any notable changes between treatment groups.

Tissue histopathology evaluations for heart, liver, lung, kidney, spleen, skeletal muscle, brain, colon, stomach, ovary, and testis have been conducted. Tissues were fixed immediately in formalin, embedding in paraffin, staining with H&E, and were reviewed by a veterinary pathologist. Histopathological examination found no test article related lesions in any tissue examined. Tissues were specifically examined for any evidence of an immune histopathologic reaction and none were observed at the 20 mg/mL dose tested.

Assessment of Immunogenic Potential in a Human HLA-DR4 Mouse Model

The reduction of NicA2-specific antibody titers 10 days after subcutaneous (s.c.) injection in Freunds Incomplete Adjuvant in human DR4 transgenic mice (N=6; 3M+3F; Taconic Biosciences) was studied. This mouse model carries a hybrid MHC class II molecule with the antigen binding domains of human HLA-DRA and HLA-DRB*0401 (representative of the DR4 supertype) and does not express endogenous mouse MHC class II molecules. Titer was defined as serum dilution to achieve OD450=0.5 in ELISA using NicA2 coated plates, and detection by goat α-mouse IgG-γ-HRP. The lowest serum dilution tested was 50-fold (Limit of Detection (LOD)). Titers from NicA2-PEG1, -PEG2, and PEG3 were compared to unPEGylated NicA2 using one-way ANOVA using Kruskal-Wallis test and Dunn's test for multiple comparison.

T Cell Stimulation and IFN-γ Secretion Assays in Human T Cells

Local Research Ethics Committee (LREC, Northeast Newcastle, UK) approval was granted prior to study commencement. Peripheral blood (60 mL) was obtained from healthy volunteers (n=5) after receiving their written informed consent. Peripheral blood mononuclear cells (PBMCs) were isolated using density-gradient centrifugation (LYMPHOPREP™, Stemcell Technologies) and then used for positive selection of CD14+ monocytes. The CD14⁻ fraction was collected and used as a source of autologous lymphocytes. Monocyte-derived dendritic cells (MoDC) were generated as previously described. T cell proliferation assays were performed by incubating the test compounds with autologous MoDC and then activation by autologous T cells for 5 days. Each sample was set up in triplet wells. Both wt NicA2 and NicA2-PEG2 were tested at 24 µg/mL, 2.4 µg/mL and 0.24 µg/mL. Phytohemagglutinin (PHA), 5 µg/mL) was used as a positive control. To determine baseline proliferation untreated MoDCs were co-cultured with autologous lymphocytes. Supernatants were collected for IFN-γ analysis prior to [³H] thymidine addition on day 5.

T cell proliferation was measured by [³H]-Thymidine incorporation in counts per minute (cpm). Analysis was performed by calculating a stimulation index (SI) of T cell proliferation by dividing the cpm value obtained for test samples with the baseline cpm value. A fold increase in IFN-γ levels (pg/mL) (measured by flow cytometry using a Cytometric Bead Array kit, BD Biosciences) was calculated by dividing the value of cells treated with each drug with the baseline value. The cut off value of a 3-fold increase was considered to be a positive response. Statistical analysis was performed using one-way ANOVA using Kruskal-Wallis test and Dunn's test for multiple comparison.

Results

To assess the safety of NicA2 in the presence of nicotine, a 28 day repeat-dose toxicology study was conducted in rats dosing 20 mg/kg of NicA2-ABD by i.v. injection every 4th day plus nicotine at 1 mg/kg/day via continuous infusion pump (equivalent to >30 cigarettes' worth of nicotine/day on a mg/kg basis). Two control groups, saline or nicotine alone, were included. The long-acting NicA2-ABD made this study possible by significantly reducing the dosing frequency and amount of material needed. NicA2-ABD has a circulatory half-life of 61 h. Serum levels of NicA2-ABD at the end of the study averaged 81 µg/mL. NicA2-ABD was well-tolerated with no observed pathology in the treatment group, including assessments of hematology, serum clinical chemistry and histopathologic examination of liver, spleen, heart, lung, kidney, brain, skeletal muscle, stomach, colon, and ovary or testis.

Example 8—Treating Nicotine Addiction and/or Facilitating Smoking Cessation

This example illustrates methods of using a variant as described herein to treat nicotine addiction and/or facilitate smoking cessation in a human adult.

An adult human subject who regularly smokes cigarettes but wishes to quit is administered a therapeutically effective amount of a pharmaceutical compositions comprising a nicotine-degrading enzyme variant (e.g., SEQ ID NOs: 5-28, or a long-acting version thereof) orally or by intravenous or subcutaneous injection. The subject is evaluated for levels of nicotine circulating in plasma, as well as for the presence and/or severity of signs and symptoms associated with nicotine withdrawal, such as headache, irritability, anxiety, and sleeplessness, as well as the number of cigarettes smoked in a given day. The subject is treated with repeated administrations until levels of nicotine circulating in plasma reach a target (reduced) level, and/or until one or more signs/symptoms of nicotine withdrawal are reduced, ameliorated, or eliminated, and/or until the subject has reduced the level of consumption of nicotine products (e.g., is smoking fewer cigarettes per day), and/or until the subject has ceased consumption of nicotine products (e.g., has quit smoking).

Example 9—Treatment of a Pediatric Patient with a Nicotine-Degrading Enzyme Variant This example illustrates methods using nicotine-degrading enzyme variants in the treatment of nicotine poisoning in a pediatric patient.

A child known to have or suspected of having ingested nicotine is administered a therapeutically effective amount of a pharmaceutical composition comprising a nicotine-degrading enzyme variant, by intravenous, intramuscular, or subcutaneous injection. The child is evaluated for the presence and/or severity of signs and symptoms associated with nicotine poisoning, including, but not limited to, seizures, coma, shortness of breath, and increased heart rate, and the child is treated until one or more signs/symptoms is reduced, ameliorated, or eliminated. Optionally, another dose of the pharmaceutical composition is administered if signs/symptoms persist and/or if nicotine plasma/brain levels remain elevated.

What is claimed is:

1. A nicotine-degrading enzyme variant comprising an amino acid sequence that is a variant of the amino acid sequence of the wild-type NicA2 enzyme set forth in SEQ ID NO: 1, wherein the variant sequence has at least 90% sequence identity to a sequence selected from (i) SEQ ID NO: 1 and (ii) SEQ ID NO: 1 having an N-terminal deletion of up to 52 amino acids, and wherein the variant sequence comprises at least one substitution at one or more of positions 104, 106, 107, 249, 355, and 426 of SEQ ID NO: 1, provided that the substitution at position 104 is selected from F104R, F104K, F104I, F104S and F104T, the substitution at position 106 is G106A, the substitution at position 107 is A107G, and the substitution at position 355 is selected from F355H, F355K, and F355E.

2. The variant of claim 1, wherein the at least one substitution is selected from F104R, F104K, F104I, F104S, F104T, G106A, A107G, E249W, E249D, F355H, F355K, F355E, A426Q, A426W, A426P, and A426C.

3. The variant of claim 1, wherein the variant sequence comprises an amino acid sequence selected from SEQ ID NO: 5, SEQ ID NO: 6, SEQ ID NO: 7, SEQ ID NO: 9, SEQ ID NO: 10, SEQ ID NO: 28, SEQ ID NO: 12, SEQ ID NO: 16, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

4. The variant of claim 1, wherein the variant sequence comprises substitutions at two or more amino acid positions selected from 104, 106, 107, 249, 355, and 426 of SEQ ID NO: 1.

5. The variant of claim 1, wherein the nicotine-degrading activity of the variant is at least about 200% of the nicotine-degrading activity of the wild-type NicA2 enzyme.

6. The variant of claim 1, wherein the variant further comprises a conservative substitution, non-conservative substitution, addition, or deletion at one or more of positions 91, 217, 250, 340, 366, 381, 427, 462, and 463 of SEQ ID NO:1.

7. The variant of claim 1, wherein the variant further comprises one or more substitutions selected from F104L, G106S, A107H, A107P, A107R, A107K, A107T, F355C, F355V, W427Q, W427E, W427S, W427M, W427H, W427L, W427R, R91A, R91Q, R91F, R91G, R91T, R91L, R91S, R91N, T250G, T250L, T250R, T250V, T250P, K340P, K340I, K340V, K340D, K340E, Q366K, Q366E, Q366V, Q366L, Q366I, Q366Y, T381P, T381I, T381V, T381Q, T381N, T381L, T381M, N462L, N462Y, N462S, N462F, N462G, N462E, N462A, N462M, 1463F, 1463Y, 1463A, 1463V, 1463L, L217Q, L217G, L217E, L217I, L217C, and L217S.

8. The variant of claim 1, wherein the variant exhibits reduced immunogenicity relative to the wild-type NicA2 enzyme.

9. The variant of claim 1, wherein the variant further comprises at least one substitution at an amino acid position selected from 74, 77, 78, 80, 262-266, 303, 304, 306, 310, 374, 377, 378, 382, 383, 450-452, and 457 of SEQ ID NO:1 that reduces the immunogenicity of the variant.

10. The variant of claim 1, wherein the variant further comprises at least one substitution, addition, or deletion in an immunogenic T-cell epitope within a region selected from amino acids 10-32, 68-94, 189-225, 248-285, 296-327, 336-391, and 435-459 of SEQ ID NO: 1.

11. The variant of claim 1, wherein the variant further comprises at least one substitution, addition, or deletion in an immunogenic T-cell epitope selected from amino acids 16-24, 73-81, 258-266, 302-310, 373-381, and 447-455 of SEQ ID NO: 1.

12. The variant of claim 1, further comprising a deletion of at least amino acids 1-38 of SEQ ID NO:1.

13. The variant of claim 1, further comprising a deletion of amino acids 1-50 of SEQ ID NO:1.

14. The variant of claim 1, further comprising one or more mutations selected from the group consisting of F163A, Y214A, Y218A, Y242A, M246A, E249A, F353V, F355V, W364V, F353A, F355A, and W364A.

15. The variant of claim 1, wherein the variant is a long-acting variant comprising the variant fused to a moiety selected from an albumin-binding peptide, an albumin-binding protein domain, human serum albumin, and an inert polypeptide.

16. The variant of claim 15, wherein the variant is fused to an inert polypeptide selected from recombinant PEG (XTEN), a homo-amino acid polymer (HAP), a proline-alanine serine polymer (PAS), and an elastin-like peptide (ELP).

17. The variant of claim 1, wherein the variant is PEGylated.

18. A pharmaceutical composition comprising a nicotine-degrading enzyme variant of claim 1 and a pharmaceutically acceptable carrier.

19. A nicotine-degrading enzyme variant comprising an amino acid sequence selected from SEQ ID NO: 5, SEQ ID NO: 6, SEQ ID NO: 7, SEQ ID NO: 9, SEQ ID NO: 10, SEQ ID NO: 28, SEQ ID NO: 12, SEQ ID NO: 16, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

20. A nicotine-degrading enzyme variant comprising an amino acid sequence that is a variant of the amino acid sequence of the wild-type NicA2 enzyme set forth in SEQ ID NO: 1, wherein the variant sequence has at least one substitution selected from the group consisting of F163A, Y214A, Y218A, Y242A, M246A, E249A, F353V, W364V, F353A, F355A, and W364A, and comprises an N-terminal deletion of 1-52 amino acids relative to SEQ ID NO: 1.

21. The variant of claim 20, wherein the N-terminal deletion is 25, 38, or 50 amino acids.

22. A method of treating nicotine addiction or facilitating smoking cessation, comprising administering to a mammalian subject in need thereof a therapeutically effective amount of a nicotine-degrading enzyme variant according to claim 1.

23. The method of claim 22, wherein the mammalian subject is a human subject.

24. The method of claim 22, where the nicotine addiction is associated with the consumption of a nicotine product selected from tobacco products and electronic cigarettes.

25. A method of treating nicotine poisoning or nicotine toxicity, comprising administering to a mammalian subject in need thereof a therapeutically effective amount of a nicotine-degrading enzyme variant according to claim 1.

26. The method of claim 25, wherein the mammalian subject is a human subject.

27. The method of claim 26, where the human subject is a child.

* * * * *

```
                            SEQUENCE LISTING

<160> NUMBER OF SEQ ID NOS: 38

<210> SEQ ID NO 1
<211> LENGTH: 482
<212> TYPE: PRT
<213> ORGANISM: Pseudomonas putida

<400> SEQUENCE: 1

Met Ser Asp Lys Thr Lys Thr Asn Glu Gly Phe Ser Arg Arg Ser Phe
1               5                   10                  15

Ile Gly Ser Ala Ala Val Val Thr Ala Gly Val Ala Gly Leu Gly Ala
            20                  25                  30

Ile Asp Ala Ala Ser Ala Thr Gln Lys Thr Asn Arg Ala Ser Thr Val
        35                  40                  45

Lys Gly Gly Phe Asp Tyr Asp Val Val Val Gly Gly Gly Phe Ala
    50                  55                  60

Gly Ala Thr Ala Ala Arg Glu Cys Gly Leu Gln Gly Tyr Arg Thr Leu
65                  70                  75                  80

Leu Leu Glu Ala Arg Ser Arg Leu Gly Gly Arg Thr Phe Thr Ser Arg
                85                  90                  95

Phe Ala Gly Gln Glu Ile Glu Phe Gly Gly Ala Trp Val His Trp Leu
            100                 105                 110

Gln Pro His Val Trp Ala Glu Met Gln Arg Tyr Gly Leu Gly Val Val
        115                 120                 125

Glu Asp Pro Leu Thr Asn Leu Asp Lys Thr Leu Ile Met Tyr Asn Asp
130                 135                 140

Gly Ser Val Glu Ser Ile Ser Pro Asp Glu Phe Gly Lys Asn Ile Arg
145                 150                 155                 160

Ile Ala Phe Glu Lys Leu Cys His Asp Ala Trp Glu Val Phe Pro Arg
                165                 170                 175

Pro His Glu Pro Met Phe Thr Glu Arg Ala Arg Glu Leu Asp Lys Ser
            180                 185                 190

Ser Val Leu Asp Arg Ile Lys Thr Leu Gly Leu Ser Arg Leu Gln Gln
        195                 200                 205

Ala Gln Ile Asn Ser Tyr Met Ala Leu Tyr Ala Gly Glu Thr Thr Asp
    210                 215                 220

Lys Phe Gly Leu Pro Gly Val Leu Lys Leu Phe Ala Cys Gly Gly Trp
225                 230                 235                 240

Asn Tyr Asp Ala Phe Met Asp Thr Glu Thr His Tyr Arg Ile Gln Gly
                245                 250                 255

Gly Thr Ile Gly Leu Ile Asn Ala Met Leu Thr Asp Ser Gly Ala Glu
            260                 265                 270

Val Arg Met Ser Val Pro Val Thr Ala Val Glu Gln Val Asn Gly Gly
        275                 280                 285

Val Lys Ile Lys Thr Asp Asp Glu Ile Ile Thr Ala Gly Val Val
    290                 295                 300

Val Met Thr Val Pro Leu Asn Thr Tyr Lys His Ile Gly Phe Thr Pro
305                 310                 315                 320

Ala Leu Ser Lys Gly Lys Gln Arg Phe Ile Lys Glu Gly Gln Leu Ser
                325                 330                 335

Lys Gly Ala Lys Leu Tyr Val His Val Lys Gln Asn Leu Gly Arg Val
```

```
              340                 345                 350
Phe Ala Phe Ala Asp Glu Gln Gln Pro Leu Asn Trp Val Gln Thr His
            355                 360                 365
Asp Tyr Ser Asp Glu Leu Gly Thr Ile Leu Ser Ile Thr Ile Ala Arg
370                 375                 380
Lys Glu Thr Ile Asp Val Asn Asp Arg Asp Ala Val Thr Arg Glu Val
385                 390                 395                 400
Gln Lys Met Phe Pro Gly Val Glu Val Leu Gly Thr Ala Ala Tyr Asp
                405                 410                 415
Trp Thr Ala Asp Pro Phe Ser Leu Gly Ala Trp Ala Ala Tyr Gly Val
                420                 425                 430
Gly Gln Leu Ser Arg Leu Lys Asp Leu Gln Ala Ala Glu Gly Arg Ile
            435                 440                 445
Leu Phe Ala Gly Ala Glu Thr Ser Asn Gly Trp His Ala Asn Ile Asp
        450                 455                 460
Gly Ala Val Glu Ser Gly Leu Arg Ala Gly Arg Glu Val Lys Gln Leu
465                 470                 475                 480
Leu Ser

<210> SEQ ID NO 2
<211> LENGTH: 432
<212> TYPE: PRT
<213> ORGANISM: Pseudomonas putida

<400> SEQUENCE: 2

Gly Phe Asp Tyr Asp Val Val Val Gly Gly Gly Phe Ala Gly Ala
1               5                   10                  15
Thr Ala Ala Arg Glu Cys Gly Leu Gln Gly Tyr Arg Thr Leu Leu Leu
                20                  25                  30
Glu Ala Arg Ser Arg Leu Gly Gly Arg Thr Phe Thr Ser Arg Phe Ala
            35                  40                  45
Gly Gln Glu Ile Glu Phe Gly Gly Ala Trp Val His Trp Leu Gln Pro
        50                  55                  60
His Val Trp Ala Glu Met Gln Arg Tyr Gly Leu Gly Val Val Glu Asp
65                  70                  75                  80
Pro Leu Thr Asn Leu Asp Lys Thr Leu Ile Met Tyr Asn Asp Gly Ser
                85                  90                  95
Val Glu Ser Ile Ser Pro Asp Glu Phe Gly Lys Asn Ile Arg Ile Ala
            100                 105                 110
Phe Glu Lys Leu Cys His Asp Ala Trp Glu Val Phe Pro Arg Pro His
        115                 120                 125
Glu Pro Met Phe Thr Glu Arg Ala Arg Glu Leu Asp Lys Ser Ser Val
130                 135                 140
Leu Asp Arg Ile Lys Thr Leu Gly Leu Ser Arg Leu Gln Gln Ala Gln
145                 150                 155                 160
Ile Asn Ser Tyr Met Ala Leu Tyr Ala Gly Glu Thr Thr Asp Lys Phe
                165                 170                 175
Gly Leu Pro Gly Val Leu Lys Leu Phe Ala Cys Gly Gly Trp Asn Tyr
            180                 185                 190
Asp Ala Phe Met Asp Thr Glu Thr His Tyr Arg Ile Gln Gly Gly Thr
        195                 200                 205
Ile Gly Leu Ile Asn Ala Met Leu Thr Asp Ser Gly Ala Glu Val Arg
    210                 215                 220
Met Ser Val Pro Val Thr Ala Val Glu Gln Val Asn Gly Gly Val Lys
```

```
            225                 230                 235                 240
        Ile Lys Thr Asp Asp Glu Ile Ile Thr Ala Gly Val Val Met
                        245                 250                 255

Thr Val Pro Leu Asn Thr Tyr Lys His Ile Gly Phe Thr Pro Ala Leu
                        260                 265                 270

Ser Lys Gly Lys Gln Arg Phe Ile Lys Glu Gly Gln Leu Ser Lys Gly
                        275                 280                 285

Ala Lys Leu Tyr Val His Val Lys Gln Asn Leu Gly Arg Val Phe Ala
                        290                 295                 300

Phe Ala Asp Glu Gln Gln Pro Leu Asn Trp Val Gln Thr His Asp Tyr
        305                 310                 315                 320

Ser Asp Glu Leu Gly Thr Ile Leu Ser Ile Thr Ile Ala Arg Lys Glu
                        325                 330                 335

Thr Ile Asp Val Asn Asp Arg Asp Ala Val Thr Arg Glu Val Gln Lys
                        340                 345                 350

Met Phe Pro Gly Val Glu Val Leu Gly Thr Ala Ala Tyr Asp Trp Thr
                        355                 360                 365

Ala Asp Pro Phe Ser Leu Gly Ala Trp Ala Tyr Gly Val Gly Gln
                        370                 375                 380

Leu Ser Arg Leu Lys Asp Leu Gln Ala Ala Glu Gly Arg Ile Leu Phe
        385                 390                 395                 400

Ala Gly Ala Glu Thr Ser Asn Gly Trp His Ala Asn Ile Asp Gly Ala
                        405                 410                 415

Val Glu Ser Gly Leu Arg Ala Gly Arg Glu Val Lys Gln Leu Leu Ser
                        420                 425                 430

<210> SEQ ID NO 3
<211> LENGTH: 457
<212> TYPE: PRT
<213> ORGANISM: Pseudomonas putida

<400> SEQUENCE: 3

Gly Val Ala Gly Leu Gly Ala Ile Asp Ala Ala Ser Ala Thr Gln Lys
1               5                   10                  15

Thr Asn Arg Ala Ser Thr Val Lys Gly Gly Phe Asp Tyr Asp Val Val
                20                  25                  30

Val Val Gly Gly Gly Phe Ala Gly Ala Thr Ala Ala Arg Glu Cys Gly
            35                  40                  45

Leu Gln Gly Tyr Arg Thr Leu Leu Leu Glu Ala Arg Ser Arg Leu Gly
        50                  55                  60

Gly Arg Thr Phe Thr Ser Arg Phe Ala Gly Gln Glu Ile Glu Phe Gly
65                  70                  75                  80

Gly Ala Trp Val His Trp Leu Gln Pro His Val Trp Ala Glu Met Gln
                85                  90                  95

Arg Tyr Gly Leu Gly Val Val Glu Asp Pro Leu Thr Asn Leu Asp Lys
            100                 105                 110

Thr Leu Ile Met Tyr Asn Asp Gly Ser Val Glu Ser Ile Ser Pro Asp
        115                 120                 125

Glu Phe Gly Lys Asn Ile Arg Ile Ala Phe Glu Lys Leu Cys His Asp
    130                 135                 140

Ala Trp Glu Val Phe Pro Arg Pro His Glu Pro Met Phe Thr Glu Arg
145                 150                 155                 160

Ala Arg Glu Leu Asp Lys Ser Ser Val Leu Asp Arg Ile Lys Thr Leu
                165                 170                 175
```

```
Gly Leu Ser Arg Leu Gln Gln Ala Gln Ile Asn Ser Tyr Met Ala Leu
            180                 185                 190

Tyr Ala Gly Glu Thr Thr Asp Lys Phe Gly Leu Pro Gly Val Leu Lys
            195                 200                 205

Leu Phe Ala Cys Gly Gly Trp Asn Tyr Asp Ala Phe Met Asp Thr Glu
            210                 215                 220

Thr His Tyr Arg Ile Gln Gly Thr Ile Gly Leu Ile Asn Ala Met
225                 230                 235                 240

Leu Thr Asp Ser Gly Ala Glu Val Arg Met Ser Val Pro Val Thr Ala
            245                 250                 255

Val Glu Gln Val Asn Gly Gly Val Lys Ile Lys Thr Asp Asp Glu
            260                 265                 270

Ile Ile Thr Ala Gly Val Val Met Thr Val Pro Leu Asn Thr Tyr
            275                 280                 285

Lys His Ile Gly Phe Thr Pro Ala Leu Ser Lys Gly Lys Gln Arg Phe
            290                 295                 300

Ile Lys Glu Gly Gln Leu Ser Lys Gly Ala Lys Leu Tyr Val His Val
305                 310                 315                 320

Lys Gln Asn Leu Gly Arg Val Phe Ala Phe Ala Asp Glu Gln Gln Pro
            325                 330                 335

Leu Asn Trp Val Gln Thr His Asp Tyr Ser Asp Glu Leu Gly Thr Ile
            340                 345                 350

Leu Ser Ile Thr Ile Ala Arg Lys Glu Thr Ile Asp Val Asn Asp Arg
            355                 360                 365

Asp Ala Val Thr Arg Glu Val Gln Lys Met Phe Pro Gly Val Glu Val
            370                 375                 380

Leu Gly Thr Ala Ala Tyr Asp Trp Thr Ala Asp Pro Phe Ser Leu Gly
385                 390                 395                 400

Ala Trp Ala Ala Tyr Gly Val Gly Gln Leu Ser Arg Leu Lys Asp Leu
            405                 410                 415

Gln Ala Ala Glu Gly Arg Ile Leu Phe Ala Gly Ala Glu Thr Ser Asn
            420                 425                 430

Gly Trp His Ala Asn Ile Asp Gly Ala Val Glu Ser Gly Leu Arg Ala
            435                 440                 445

Gly Arg Glu Val Lys Gln Leu Leu Ser
            450                 455

<210> SEQ ID NO 4
<211> LENGTH: 444
<212> TYPE: PRT
<213> ORGANISM: Pseudomonas putida

<400> SEQUENCE: 4

Thr Gln Lys Thr Asn Arg Ala Ser Thr Val Lys Gly Gly Phe Asp Tyr
1               5                   10                  15

Asp Val Val Val Gly Gly Gly Phe Ala Gly Thr Ala Ala Arg
            20                  25                  30

Glu Cys Gly Leu Gln Gly Tyr Arg Thr Leu Leu Glu Ala Arg Ser
            35                  40                  45

Arg Leu Gly Gly Arg Thr Phe Thr Ser Arg Phe Ala Gly Gln Glu Ile
            50                  55                  60

Glu Phe Gly Gly Ala Trp Val His Trp Leu Gln Pro His Val Trp Ala
65                  70                  75                  80

Glu Met Gln Arg Tyr Gly Leu Gly Val Val Glu Asp Pro Leu Thr Asn
            85                  90                  95
```

```
Leu Asp Lys Thr Leu Ile Met Tyr Asn Asp Gly Ser Val Glu Ser Ile
                100                 105                 110

Ser Pro Asp Glu Phe Gly Lys Asn Ile Arg Ile Ala Phe Glu Lys Leu
            115                 120                 125

Cys His Asp Ala Trp Glu Val Phe Pro Arg Pro His Glu Pro Met Phe
        130                 135                 140

Thr Glu Arg Ala Arg Glu Leu Asp Lys Ser Ser Val Leu Asp Arg Ile
145                 150                 155                 160

Lys Thr Leu Gly Leu Ser Arg Leu Gln Gln Ala Gln Ile Asn Ser Tyr
                165                 170                 175

Met Ala Leu Tyr Ala Gly Glu Thr Thr Asp Lys Phe Gly Leu Pro Gly
            180                 185                 190

Val Leu Lys Leu Phe Ala Cys Gly Gly Trp Asn Tyr Asp Ala Phe Met
        195                 200                 205

Asp Thr Glu Thr His Tyr Arg Ile Gln Gly Gly Thr Ile Gly Leu Ile
    210                 215                 220

Asn Ala Met Leu Thr Asp Ser Gly Ala Glu Val Arg Met Ser Val Pro
225                 230                 235                 240

Val Thr Ala Val Glu Gln Val Asn Gly Gly Val Lys Ile Lys Thr Asp
                245                 250                 255

Asp Asp Glu Ile Ile Thr Ala Gly Val Val Met Thr Val Pro Leu
            260                 265                 270

Asn Thr Tyr Lys His Ile Gly Phe Thr Pro Ala Leu Ser Lys Gly Lys
        275                 280                 285

Gln Arg Phe Ile Lys Glu Gly Gln Leu Ser Lys Gly Ala Lys Leu Tyr
    290                 295                 300

Val His Val Lys Gln Asn Leu Gly Arg Val Phe Ala Phe Ala Asp Glu
305                 310                 315                 320

Gln Gln Pro Leu Asn Trp Val Gln Thr His Asp Tyr Ser Asp Glu Leu
                325                 330                 335

Gly Thr Ile Leu Ser Ile Thr Ile Ala Arg Lys Glu Thr Ile Asp Val
            340                 345                 350

Asn Asp Arg Asp Ala Val Thr Arg Glu Val Gln Lys Met Phe Pro Gly
        355                 360                 365

Val Glu Val Leu Gly Thr Ala Ala Tyr Asp Trp Thr Ala Asp Pro Phe
    370                 375                 380

Ser Leu Gly Ala Trp Ala Ala Tyr Gly Val Gly Gln Leu Ser Arg Leu
385                 390                 395                 400

Lys Asp Leu Gln Ala Ala Glu Gly Arg Ile Leu Phe Ala Gly Ala Glu
                405                 410                 415

Thr Ser Asn Gly Trp His Ala Asn Ile Asp Gly Ala Val Glu Ser Gly
            420                 425                 430

Leu Arg Ala Gly Arg Glu Val Lys Gln Leu Leu Ser
        435                 440

<210> SEQ ID NO 5
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5
```

```
Ser Asp Lys Thr Lys Thr Asn Glu Gly Phe Ser Arg Arg Ser Phe Ile
 1               5                  10                  15
Gly Ser Ala Ala Val Val Thr Ala Gly Val Ala Gly Leu Gly Ala Ile
             20                  25                  30
Asp Ala Ala Ser Ala Thr Gln Lys Thr Asn Arg Ala Ser Thr Val Lys
         35                  40                  45
Gly Gly Phe Asp Tyr Asp Val Val Val Gly Gly Phe Ala Gly
     50                  55                  60
Ala Thr Ala Ala Arg Glu Cys Gly Leu Gln Gly Tyr Arg Thr Leu Leu
 65                  70                  75                  80
Leu Glu Ala Arg Ser Arg Leu Gly Gly Arg Thr Phe Thr Ser Arg Phe
                 85                  90                  95
Ala Gly Gln Glu Ile Glu Arg Gly Gly Ala Trp Val His Trp Leu Gln
             100                 105                 110
Pro His Val Trp Ala Glu Met Gln Arg Tyr Gly Leu Gly Val Val Glu
         115                 120                 125
Asp Pro Leu Thr Asn Leu Asp Lys Thr Leu Ile Met Tyr Asn Asp Gly
     130                 135                 140
Ser Val Glu Ser Ile Ser Pro Asp Glu Phe Gly Lys Asn Ile Arg Ile
145                 150                 155                 160
Ala Phe Glu Lys Leu Cys His Asp Ala Trp Glu Val Phe Pro Arg Pro
                 165                 170                 175
His Glu Pro Met Phe Thr Glu Arg Ala Arg Glu Leu Asp Lys Ser Ser
             180                 185                 190
Val Leu Asp Arg Ile Lys Thr Leu Gly Leu Ser Arg Leu Gln Gln Ala
         195                 200                 205
Gln Ile Asn Ser Tyr Met Ala Leu Tyr Ala Gly Glu Thr Thr Asp Lys
     210                 215                 220
Phe Gly Leu Pro Gly Val Leu Lys Leu Phe Ala Cys Gly Gly Trp Asn
225                 230                 235                 240
Tyr Asp Ala Phe Met Asp Thr Glu Thr His Tyr Arg Ile Gln Gly Gly
                 245                 250                 255
Thr Ile Gly Leu Ile Asn Ala Met Leu Thr Asp Ser Gly Ala Glu Val
             260                 265                 270
Arg Met Ser Val Pro Val Thr Ala Val Glu Gln Val Asn Gly Gly Val
         275                 280                 285
Lys Ile Lys Thr Asp Asp Glu Ile Ile Thr Ala Gly Val Val Val
     290                 295                 300
Met Thr Val Pro Leu Asn Thr Tyr Lys His Ile Gly Phe Thr Pro Ala
305                 310                 315                 320
Leu Ser Lys Gly Lys Gln Arg Phe Ile Lys Glu Gly Gln Leu Ser Lys
                 325                 330                 335
Gly Ala Lys Leu Tyr Val His Val Lys Gln Asn Leu Gly Arg Val Phe
             340                 345                 350
Ala Phe Ala Asp Glu Gln Gln Pro Leu Asn Trp Val Gln Thr His Asp
         355                 360                 365
Tyr Ser Asp Glu Leu Gly Thr Ile Leu Ser Ile Thr Ile Ala Arg Lys
     370                 375                 380
Glu Thr Ile Asp Val Asn Asp Arg Asp Ala Val Thr Arg Glu Val Gln
385                 390                 395                 400
Lys Met Phe Pro Gly Val Glu Val Leu Gly Thr Ala Ala Tyr Asp Trp
                 405                 410                 415
Thr Ala Asp Pro Phe Ser Leu Gly Ala Trp Ala Ala Tyr Gly Val Gly
```

```
                420                 425                 430
Gln Leu Ser Arg Leu Lys Asp Leu Gln Ala Ala Glu Gly Arg Ile Leu
            435                 440                 445

Phe Ala Gly Ala Glu Thr Ser Asn Gly Trp His Ala Asn Ile Asp Gly
        450                 455                 460

Ala Val Glu Ser Gly Leu Arg Ala Gly Arg Glu Val Lys Gln Leu Leu
465                 470                 475                 480

Ser

<210> SEQ ID NO 6
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Ser Asp Lys Thr Lys Thr Asn Glu Gly Phe Ser Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Lys Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285
```

-continued

```
Lys Ile Lys Thr Asp Asp Glu Ile Ile Thr Ala Gly Val Val
    290                 295                 300
Met Thr Val Pro Leu Asn Thr Tyr Lys His Ile Gly Phe Thr Pro Ala
305                 310                 315                 320
Leu Ser Lys Gly Lys Gln Arg Phe Ile Lys Glu Gly Gln Leu Ser Lys
                325                 330                 335
Gly Ala Lys Leu Tyr Val His Val Lys Gln Asn Leu Gly Arg Val Phe
            340                 345                 350
Ala Phe Ala Asp Glu Gln Gln Pro Leu Asn Trp Val Gln Thr His Asp
        355                 360                 365
Tyr Ser Asp Glu Leu Gly Thr Ile Leu Ser Ile Thr Ile Ala Arg Lys
370                 375                 380
Glu Thr Ile Asp Val Asn Asp Arg Asp Ala Val Thr Arg Glu Val Gln
385                 390                 395                 400
Lys Met Phe Pro Gly Val Glu Val Leu Gly Thr Ala Ala Tyr Asp Trp
                405                 410                 415
Thr Ala Asp Pro Phe Ser Leu Gly Ala Trp Ala Ala Tyr Gly Val Gly
            420                 425                 430
Gln Leu Ser Arg Leu Lys Asp Leu Gln Ala Ala Glu Gly Arg Ile Leu
        435                 440                 445
Phe Ala Gly Ala Glu Thr Ser Asn Gly Trp His Ala Asn Ile Asp Gly
450                 455                 460
Ala Val Glu Ser Gly Leu Arg Ala Gly Arg Glu Val Lys Gln Leu Leu
465                 470                 475                 480
Ser
```

<210> SEQ ID NO 7
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Ser Asp Lys Thr Lys Thr Asn Glu Gly Phe Ser Arg Arg Ser Phe Ile
1               5                   10                  15
Gly Ser Ala Ala Val Val Thr Ala Gly Val Ala Gly Leu Gly Ala Ile
            20                  25                  30
Asp Ala Ala Ser Ala Thr Gln Lys Thr Asn Arg Ala Ser Thr Val Lys
        35                  40                  45
Gly Gly Phe Asp Tyr Asp Val Val Val Gly Gly Gly Phe Ala Gly
    50                  55                  60
Ala Thr Ala Ala Arg Glu Cys Gly Leu Gln Gly Tyr Arg Thr Leu Leu
65                  70                  75                  80
Leu Glu Ala Arg Ser Arg Leu Gly Gly Arg Thr Phe Thr Ser Arg Phe
                85                  90                  95
Ala Gly Gln Glu Ile Glu Ile Gly Gly Ala Trp Val His Trp Leu Gln
            100                 105                 110
Pro His Val Trp Ala Glu Met Gln Arg Tyr Gly Leu Gly Val Val Glu
        115                 120                 125
Asp Pro Leu Thr Asn Leu Asp Lys Thr Leu Ile Met Tyr Asn Asp Gly
    130                 135                 140
Ser Val Glu Ser Ile Ser Pro Asp Glu Phe Gly Lys Asn Ile Arg Ile
145                 150                 155                 160
```

Ala Phe Glu Lys Leu Cys His Asp Ala Trp Glu Val Phe Pro Arg Pro
            165                 170                 175

His Glu Pro Met Phe Thr Glu Arg Ala Arg Glu Leu Asp Lys Ser Ser
        180                 185                 190

Val Leu Asp Arg Ile Lys Thr Leu Gly Leu Ser Arg Leu Gln Gln Ala
    195                 200                 205

Gln Ile Asn Ser Tyr Met Ala Leu Tyr Ala Gly Glu Thr Thr Asp Lys
210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
            245                 250                 255

Thr Ile Gly Leu Ile Asn Ala Met Leu Thr Asp Ser Gly Ala Glu Val
        260                 265                 270

Arg Met Ser Val Pro Val Thr Ala Val Glu Gln Val Asn Gly Gly Val
    275                 280                 285

Lys Ile Lys Thr Asp Asp Glu Ile Ile Thr Ala Gly Val Val Val
290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
            325                 330                 335

Gly Ala Lys Leu Tyr Val His Val Lys Gln Asn Leu Gly Arg Val Phe
        340                 345                 350

Ala Phe Ala Asp Glu Gln Gln Pro Leu Asn Trp Val Gln Thr His Asp
    355                 360                 365

Tyr Ser Asp Glu Leu Gly Thr Ile Leu Ser Ile Thr Ile Ala Arg Lys
370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
            405                 410                 415

Thr Ala Asp Pro Phe Ser Leu Gly Ala Trp Ala Ala Tyr Gly Val Gly
        420                 425                 430

Gln Leu Ser Arg Leu Lys Asp Leu Gln Ala Ala Glu Gly Arg Ile Leu
    435                 440                 445

Phe Ala Gly Ala Glu Thr Ser Asn Gly Trp His Ala Asn Ile Asp Gly
450                 455                 460

Ala Val Glu Ser Gly Leu Arg Ala Gly Arg Glu Val Lys Gln Leu Leu
465                 470                 475                 480

Ser

<210> SEQ ID NO 8
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile

-continued

```
                20                  25                  30
Asp Ala Ala Ser Ala Thr Gln Lys Thr Asn Arg Ala Ser Thr Val Lys
             35                  40                  45
Gly Gly Phe Asp Tyr Asp Val Val Val Gly Gly Phe Ala Gly
     50                  55                  60
Ala Thr Ala Ala Arg Glu Cys Gly Leu Gln Gly Tyr Arg Thr Leu Leu
 65                  70                  75                  80
Leu Glu Ala Arg Ser Arg Leu Gly Gly Arg Thr Phe Thr Ser Arg Phe
                 85                  90                  95
Ala Gly Gln Glu Ile Glu Leu Gly Gly Ala Trp Val His Trp Leu Gln
            100                 105                 110
Pro His Val Trp Ala Glu Met Gln Arg Tyr Gly Leu Gly Val Val Glu
            115                 120                 125
Asp Pro Leu Thr Asn Leu Asp Lys Thr Leu Ile Met Tyr Asn Asp Gly
            130                 135                 140
Ser Val Glu Ser Ile Ser Pro Asp Glu Phe Gly Lys Asn Ile Arg Ile
145                 150                 155                 160
Ala Phe Glu Lys Leu Cys His Asp Ala Trp Glu Val Phe Pro Arg Pro
                165                 170                 175
His Glu Pro Met Phe Thr Glu Arg Ala Arg Glu Leu Asp Lys Ser Ser
            180                 185                 190
Val Leu Asp Arg Ile Lys Thr Leu Gly Leu Ser Arg Leu Gln Gln Ala
            195                 200                 205
Gln Ile Asn Ser Tyr Met Ala Leu Tyr Ala Gly Glu Thr Thr Asp Lys
            210                 215                 220
Phe Gly Leu Pro Gly Val Leu Lys Leu Phe Ala Cys Gly Gly Trp Asn
225                 230                 235                 240
Tyr Asp Ala Phe Met Asp Thr Glu Thr His Tyr Arg Ile Gln Gly Gly
                245                 250                 255
Thr Ile Gly Leu Ile Asn Ala Met Leu Thr Asp Ser Gly Ala Glu Val
            260                 265                 270
Arg Met Ser Val Pro Val Thr Ala Val Glu Gln Val Asn Gly Gly Val
            275                 280                 285
Lys Ile Lys Thr Asp Asp Glu Ile Ile Thr Ala Gly Val Val Val
            290                 295                 300
Met Thr Val Pro Leu Asn Thr Tyr Lys His Ile Gly Phe Thr Pro Ala
305                 310                 315                 320
Leu Ser Lys Gly Lys Gln Arg Phe Ile Lys Glu Gly Gln Leu Ser Lys
                325                 330                 335
Gly Ala Lys Leu Tyr Val His Val Lys Gln Asn Leu Gly Arg Val Phe
            340                 345                 350
Ala Phe Ala Asp Glu Gln Pro Leu Asn Trp Val Gln Thr His Asp
            355                 360                 365
Tyr Ser Asp Glu Leu Gly Thr Ile Leu Ser Ile Thr Ile Ala Arg Lys
            370                 375                 380
Glu Thr Ile Asp Val Asn Asp Arg Asp Ala Val Thr Arg Glu Val Gln
385                 390                 395                 400
Lys Met Phe Pro Gly Val Glu Val Leu Gly Thr Ala Ala Tyr Asp Trp
                405                 410                 415
Thr Ala Asp Pro Phe Ser Leu Gly Ala Trp Ala Ala Tyr Gly Val Gly
            420                 425                 430
Gln Leu Ser Arg Leu Lys Asp Leu Gln Ala Ala Glu Gly Arg Ile Leu
            435                 440                 445
```

Phe Ala Gly Ala Glu Thr Ser Asn Gly Trp His Ala Asn Ile Asp Gly
    450                 455                 460

Ala Val Glu Ser Gly Leu Arg Ala Gly Arg Glu Val Lys Gln Leu Leu
465                 470                 475                 480

Ser

<210> SEQ ID NO 9
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Ser Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
    290                 295                 300

Met Thr Val Pro Leu Asn Thr Tyr Lys His Ile Gly Phe Thr Pro Ala

```
305                 310                 315                 320
Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
                340                 345                 350

Ala Phe Ala Asp Glu Gln Pro Leu Asn Trp Val Gln Thr His Asp
                355                 360                 365

Tyr Ser Asp Glu Leu Gly Thr Ile Leu Ser Ile Thr Ile Ala Arg Lys
                370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                    405                 410                 415

Thr Ala Asp Pro Phe Ser Leu Gly Ala Trp Ala Ala Tyr Gly Val Gly
                420                 425                 430

Gln Leu Ser Arg Leu Lys Asp Leu Gln Ala Ala Glu Gly Arg Ile Leu
                435                 440                 445

Phe Ala Gly Ala Glu Thr Ser Asn Gly Trp His Ala Asn Ile Asp Gly
                450                 455                 460

Ala Val Glu Ser Gly Leu Arg Ala Gly Arg Glu Val Lys Gln Leu Leu
465                 470                 475                 480

Ser

<210> SEQ ID NO 10
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
                35                  40                  45

Gly Gly Phe Asp Tyr Asp Val Val Val Gly Gly Gly Phe Ala Gly
                50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Thr Gly Gly Ala Trp Val His Trp Leu Gln
                100                 105                 110

Pro His Val Trp Ala Glu Met Gln Arg Tyr Gly Leu Gly Val Val Glu
                115                 120                 125

Asp Pro Leu Thr Asn Leu Asp Lys Thr Leu Ile Met Tyr Asn Asp Gly
                130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175
```

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
    290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Phe Ala Asp Glu Gln Pro Leu Asn Trp Val Gln Thr His Asp
        355                 360                 365

Tyr Ser Asp Glu Leu Gly Thr Ile Leu Ser Ile Thr Ile Ala Arg Lys
370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
450                 455                 460

Ala Val Glu Ser Gly Leu Arg Ala Gly Arg Glu Val Lys Gln Leu Leu
465                 470                 475                 480

Ser

<210> SEQ ID NO 11
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

```
Gly Gly Phe Asp Tyr Asp Val Val Val Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Ser Ala Trp Val His Trp Leu Gln
                100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
                180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
    290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Phe Ala Asp Glu Gln Gln Pro Leu Asn Trp Val Gln Thr His Asp
        355                 360                 365

Tyr Ser Asp Glu Leu Gly Thr Ile Leu Ser Ile Thr Ile Ala Arg Lys
    370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
    450                 455                 460
```

Ala Val Glu Ser Gly Leu Arg Ala Gly Arg Glu Val Lys Gln Leu Leu
465                 470                 475                 480

Ser

<210> SEQ ID NO 12
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
            35                  40                  45

Gly Gly Phe Asp Tyr Asp Val Val Val Gly Gly Phe Ala Gly
        50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Ala Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
    290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
                340                 345                 350

Ala Phe Ala Asp Glu Gln Gln Pro Leu Asn Trp Val Gln Thr His Asp
            355                 360                 365

Tyr Ser Asp Glu Leu Gly Thr Ile Leu Ser Ile Thr Ile Ala Arg Lys
        370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
            450                 455                 460

Ala Val Glu Ser Gly Leu Arg Ala Gly Arg Glu Val Lys Gln Leu Leu
465                 470                 475                 480

Ser

<210> SEQ ID NO 13
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
            35                  40                  45

Gly Gly Phe Asp Tyr Asp Val Val Val Gly Gly Gly Phe Ala Gly
        50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Arg Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala

```
                195                 200                 205
Gln Ile Asn Ser Tyr Met Ala Leu Tyr Ala Gly Glu Thr Thr Asp Lys
        210                 215                 220
Phe Gly Leu Pro Gly Val Leu Lys Leu Phe Ala Cys Gly Gly Trp Asn
225                 230                 235                 240
Tyr Asp Ala Phe Met Asp Thr Glu Thr His Tyr Arg Ile Gln Gly Gly
                245                 250                 255
Thr Ile Gly Leu Ile Asn Ala Met Leu Thr Asp Ser Gly Ala Glu Val
            260                 265                 270
Arg Met Ser Val Pro Val Thr Ala Val Glu Gln Val Asn Gly Gly Val
            275                 280                 285
Lys Ile Lys Thr Asp Asp Glu Ile Ile Thr Ala Gly Val Val Val
        290                 295                 300
Met Thr Val Pro Leu Asn Thr Tyr Lys His Ile Gly Phe Thr Pro Ala
305                 310                 315                 320
Leu Ser Lys Gly Lys Gln Arg Phe Ile Lys Glu Gly Gln Leu Ser Lys
                325                 330                 335
Gly Ala Lys Leu Tyr Val His Val Lys Gln Asn Leu Gly Arg Val Phe
            340                 345                 350
Ala Phe Ala Asp Glu Gln Gln Pro Leu Asn Trp Val Gln Thr His Asp
            355                 360                 365
Tyr Ser Asp Glu Leu Gly Thr Ile Leu Ser Ile Thr Ile Ala Arg Lys
        370                 375                 380
Glu Thr Ile Asp Val Asn Asp Arg Asp Ala Val Thr Arg Glu Val Gln
385                 390                 395                 400
Lys Met Phe Pro Gly Val Glu Val Leu Gly Thr Ala Ala Tyr Asp Trp
                405                 410                 415
Thr Ala Asp Pro Phe Ser Leu Gly Ala Trp Ala Ala Tyr Gly Val Gly
            420                 425                 430
Gln Leu Ser Arg Leu Lys Asp Leu Gln Ala Ala Glu Gly Arg Ile Leu
            435                 440                 445
Phe Ala Gly Ala Glu Thr Ser Asn Gly Trp His Ala Asn Ile Asp Gly
        450                 455                 460
Ala Val Glu Ser Gly Leu Arg Ala Gly Arg Glu Val Lys Gln Leu Leu
465                 470                 475                 480
Ser

<210> SEQ ID NO 14
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gly Phe Asp Tyr Asp Val Val Val Gly Gly Phe Ala Gly Ala
1               5                   10                  15
Thr Ala Ala Arg Glu Cys Gly Leu Gln Gly Tyr Arg Thr Leu Leu Leu
                20                  25                  30
Glu Ala Arg Ser Arg Leu Gly Gly Arg Thr Phe Thr Ser Arg Phe Ala
            35                  40                  45
Gly Gln Glu Ile Glu Phe Gly Gly Arg Trp Val His Trp Leu Gln Pro
        50                  55                  60
```

His Val Trp Ala Glu Met Gln Arg Tyr Gly Leu Gly Val Val Glu Asp
 65                  70                  75                  80

Pro Leu Thr Asn Leu Asp Lys Thr Leu Ile Met Tyr Asn Asp Gly Ser
                 85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
    130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
    210                 215                 220

Met Ser Val Pro Val Thr Ala Val Glu Gln Val Asn Gly Gly Val Lys
225                 230                 235                 240

Ile Lys Thr Asp Asp Glu Ile Ile Thr Ala Gly Val Val Val Met
                245                 250                 255

Thr Val Pro Leu Asn Thr Tyr Lys His Ile Gly Phe Thr Pro Ala Leu
                260                 265                 270

Ser Lys Gly Lys Gln Arg Phe Ile Lys Glu Gly Gln Leu Ser Lys Gly
            275                 280                 285

Ala Lys Leu Tyr Val His Val Lys Gln Asn Leu Gly Arg Val Phe Ala
        290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365

Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430

<210> SEQ ID NO 15
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

```
Ser Asp Lys Thr Lys Thr Asn Glu Gly Phe Ser Arg Arg Ser Phe Ile
1               5                   10                  15
Gly Ser Ala Ala Val Val Thr Ala Gly Val Ala Gly Leu Gly Ala Ile
            20                  25                  30
Asp Ala Ala Ser Ala Thr Gln Lys Thr Asn Arg Ala Ser Thr Val Lys
        35                  40                  45
Gly Gly Phe Asp Tyr Asp Val Val Val Gly Gly Phe Ala Gly
    50                  55                  60
Ala Thr Ala Ala Arg Glu Cys Gly Leu Gln Gly Tyr Arg Thr Leu Leu
65                  70                  75                  80
Leu Glu Ala Arg Ser Arg Leu Gly Arg Thr Phe Thr Ser Arg Phe
                85                  90                  95
Ala Gly Gln Glu Ile Glu Phe Gly Gly Thr Trp Val His Trp Leu Gln
                100                 105                 110
Pro His Val Trp Ala Glu Met Gln Arg Tyr Gly Leu Gly Val Val Glu
            115                 120                 125
Asp Pro Leu Thr Asn Leu Asp Lys Thr Leu Ile Met Tyr Asn Asp Gly
        130                 135                 140
Ser Val Glu Ser Ile Ser Pro Asp Glu Phe Gly Lys Asn Ile Arg Ile
145                 150                 155                 160
Ala Phe Glu Lys Leu Cys His Asp Ala Trp Glu Val Phe Pro Arg Pro
                165                 170                 175
His Glu Pro Met Phe Thr Glu Arg Ala Arg Glu Leu Asp Lys Ser Ser
            180                 185                 190
Val Leu Asp Arg Ile Lys Thr Leu Gly Leu Ser Arg Leu Gln Gln Ala
        195                 200                 205
Gln Ile Asn Ser Tyr Met Ala Leu Tyr Ala Gly Glu Thr Thr Asp Lys
    210                 215                 220
Phe Gly Leu Pro Gly Val Leu Lys Leu Phe Ala Cys Gly Gly Trp Asn
225                 230                 235                 240
Tyr Asp Ala Phe Met Asp Thr Glu Thr His Tyr Arg Ile Gln Gly Gly
                245                 250                 255
Thr Ile Gly Leu Ile Asn Ala Met Leu Thr Asp Ser Gly Ala Glu Val
            260                 265                 270
Arg Met Ser Val Pro Val Thr Ala Val Glu Gln Val Asn Gly Gly Val
        275                 280                 285
Lys Ile Lys Thr Asp Asp Glu Ile Ile Thr Ala Gly Val Val Val
    290                 295                 300
Met Thr Val Pro Leu Asn Thr Tyr Lys His Ile Gly Phe Thr Pro Ala
305                 310                 315                 320
Leu Ser Lys Gly Lys Gln Arg Phe Ile Lys Glu Gly Gln Leu Ser Lys
                325                 330                 335
Gly Ala Lys Leu Tyr Val His Val Lys Gln Asn Leu Gly Arg Val Phe
            340                 345                 350
Ala Phe Ala Asp Glu Gln Gln Pro Leu Asn Trp Val Gln Thr His Asp
        355                 360                 365
Tyr Ser Asp Glu Leu Gly Thr Ile Leu Ser Ile Thr Ile Ala Arg Lys
    370                 375                 380
Glu Thr Ile Asp Val Asn Asp Arg Asp Ala Val Thr Arg Glu Val Gln
385                 390                 395                 400
Lys Met Phe Pro Gly Val Glu Val Leu Gly Thr Ala Ala Tyr Asp Trp
                405                 410                 415
```

```
Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
450                 455                 460

Ala Val Glu Ser Gly Leu Arg Ala Gly Arg Glu Val Lys Gln Leu Leu
465                 470                 475                 480

Ser
```

<210> SEQ ID NO 16
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

```
Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Gly Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
```

```
                275                 280                 285
Lys Ile Lys Thr Asp Asp Glu Ile Ile Thr Ala Gly Val Val Val
    290                 295                 300
Met Thr Val Pro Leu Asn Thr Tyr Lys His Ile Gly Phe Thr Pro Ala
305                 310                 315                 320
Leu Ser Lys Gly Lys Gln Arg Phe Ile Lys Glu Gly Gln Leu Ser Lys
                325                 330                 335
Gly Ala Lys Leu Tyr Val His Val Lys Gln Asn Leu Gly Arg Val Phe
                340                 345                 350
Ala Phe Ala Asp Glu Gln Gln Pro Leu Asn Trp Val Gln Thr His Asp
                355                 360                 365
Tyr Ser Asp Glu Leu Gly Thr Ile Leu Ser Ile Thr Ile Ala Arg Lys
        370                 375                 380
Glu Thr Ile Asp Val Asn Asp Arg Asp Ala Val Thr Arg Glu Val Gln
385                 390                 395                 400
Lys Met Phe Pro Gly Val Glu Val Leu Gly Thr Ala Ala Tyr Asp Trp
                405                 410                 415
Thr Ala Asp Pro Phe Ser Leu Gly Ala Trp Ala Ala Tyr Gly Val Gly
                420                 425                 430
Gln Leu Ser Arg Leu Lys Asp Leu Gln Ala Ala Glu Gly Arg Ile Leu
                435                 440                 445
Phe Ala Gly Ala Glu Thr Ser Asn Gly Trp His Ala Asn Ile Asp Gly
            450                 455                 460
Ala Val Glu Ser Gly Leu Arg Ala Gly Arg Glu Val Lys Gln Leu Leu
465                 470                 475                 480
Ser

<210> SEQ ID NO 17
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Ser Asp Lys Thr Lys Thr Asn Glu Gly Phe Ser Arg Arg Ser Phe Ile
1               5                   10                  15
Gly Ser Ala Ala Val Val Thr Ala Gly Val Ala Gly Leu Gly Ala Ile
                20                  25                  30
Asp Ala Ala Ser Ala Thr Gln Lys Thr Asn Arg Ala Ser Thr Val Lys
            35                  40                  45
Gly Gly Phe Asp Tyr Asp Val Val Val Gly Gly Gly Phe Ala Gly
        50                  55                  60
Ala Thr Ala Ala Arg Glu Cys Gly Leu Gln Gly Tyr Arg Thr Leu Leu
65                  70                  75                  80
Leu Glu Ala Arg Ser Arg Leu Gly Gly Arg Thr Phe Thr Ser Arg Phe
                85                  90                  95
Ala Gly Gln Glu Ile Glu Phe Gly Gly His Trp Val His Trp Leu Gln
                100                 105                 110
Pro His Val Trp Ala Glu Met Gln Arg Tyr Gly Leu Gly Val Val Glu
            115                 120                 125
Asp Pro Leu Thr Asn Leu Asp Lys Thr Leu Ile Met Tyr Asn Asp Gly
        130                 135                 140
```

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
            165                 170                 175

His Glu Pro Met Phe Thr Glu Arg Ala Arg Glu Leu Asp Lys Ser Ser
        180                 185                 190

Val Leu Asp Arg Ile Lys Thr Leu Gly Leu Ser Arg Leu Gln Gln Ala
    195                 200                 205

Gln Ile Asn Ser Tyr Met Ala Leu Tyr Ala Gly Glu Thr Thr Asp Lys
210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
            245                 250                 255

Thr Ile Gly Leu Ile Asn Ala Met Leu Thr Asp Ser Gly Ala Glu Val
        260                 265                 270

Arg Met Ser Val Pro Val Thr Ala Val Glu Gln Val Asn Gly Gly Val
    275                 280                 285

Lys Ile Lys Thr Asp Asp Glu Ile Ile Thr Ala Gly Val Val Val
290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
            325                 330                 335

Gly Ala Lys Leu Tyr Val His Val Lys Gln Asn Leu Gly Arg Val Phe
        340                 345                 350

Ala Phe Ala Asp Glu Gln Gln Pro Leu Asn Trp Val Gln Thr His Asp
    355                 360                 365

Tyr Ser Asp Glu Leu Gly Thr Ile Leu Ser Ile Thr Ile Ala Arg Lys
370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
            405                 410                 415

Thr Ala Asp Pro Phe Ser Leu Gly Ala Trp Ala Ala Tyr Gly Val Gly
        420                 425                 430

Gln Leu Ser Arg Leu Lys Asp Leu Gln Ala Ala Glu Gly Arg Ile Leu
    435                 440                 445

Phe Ala Gly Ala Glu Thr Ser Asn Gly Trp His Ala Asn Ile Asp Gly
450                 455                 460

Ala Val Glu Ser Gly Leu Arg Ala Gly Arg Glu Val Lys Gln Leu Leu
465                 470                 475                 480

Ser

<210> SEQ ID NO 18
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 18

Ser Asp Lys Thr Lys Thr Asn Glu Gly Phe Ser Arg Arg Ser Phe Ile
1               5                   10                  15

```
Gly Ser Ala Ala Val Val Thr Ala Gly Val Ala Gly Leu Gly Ala Ile
        20                  25                  30

Asp Ala Ala Ser Ala Thr Gln Lys Thr Asn Arg Ala Ser Thr Val Lys
            35                  40                  45

Gly Gly Phe Asp Tyr Asp Val Val Val Gly Gly Phe Ala Gly
50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Pro Trp Val His Trp Leu Gln
            100                 105                 110

Pro His Val Trp Ala Glu Met Gln Arg Tyr Gly Leu Gly Val Val Glu
            115                 120                 125

Asp Pro Leu Thr Asn Leu Asp Lys Thr Leu Ile Met Tyr Asn Asp Gly
        130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
        210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
        290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Phe Ala Asp Glu Gln Gln Pro Leu Asn Trp Val Gln Thr His Asp
        355                 360                 365

Tyr Ser Asp Glu Leu Gly Thr Ile Leu Ser Ile Thr Ile Ala Arg Lys
        370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430
```

```
Gln Leu Ser Arg Leu Lys Asp Leu Gln Ala Ala Glu Gly Arg Ile Leu
            435                 440                 445

Phe Ala Gly Ala Glu Thr Ser Asn Gly Trp His Ala Asn Ile Asp Gly
450                 455                 460

Ala Val Glu Ser Gly Leu Arg Ala Gly Arg Glu Val Lys Gln Leu Leu
465                 470                 475                 480

Ser

<210> SEQ ID NO 19
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Phe Ala Gly
50                  55                  60

Ala Thr Ala Ala Arg Glu Cys Gly Leu Gln Tyr Arg Thr Leu Leu
65                  70                  75                  80

Leu Glu Ala Arg Ser Arg Leu Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
210                 215                 220

Phe Gly Leu Pro Gly Val Leu Lys Leu Phe Ala Cys Gly Gly Trp Asn
225                 230                 235                 240

Tyr Asp Ala Phe Met Asp Thr Trp Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Asp Glu Ile Ile Thr Ala Gly Val Val Val
290                 295                 300
```

```
Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
            325                 330                 335

Gly Ala Lys Leu Tyr Val His Val Lys Gln Asn Leu Gly Arg Val Phe
        340                 345                 350

Ala Phe Ala Asp Glu Gln Pro Leu Asn Trp Val Gln Thr His Asp
    355                 360                 365

Tyr Ser Asp Glu Leu Gly Thr Ile Leu Ser Ile Thr Ile Ala Arg Lys
370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
    450                 455                 460

Ala Val Glu Ser Gly Leu Arg Ala Gly Arg Glu Val Lys Gln Leu Leu
465                 470                 475                 480

Ser

<210> SEQ ID NO 20
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
```

His Glu Pro Met Phe Thr Glu Arg Ala Arg Glu Leu Asp Lys Ser Ser
            165                 170                 175

Val Leu Asp Arg Ile Lys Thr Leu Gly Leu Ser Arg Leu Gln Gln Ala
180                 185                 190

Gln Ile Asn Ser Tyr Met Ala Leu Tyr Ala Gly Glu Thr Thr Asp Lys
            195                 200                 205

Phe Gly Leu Pro Gly Val Leu Lys Leu Phe Ala Cys Gly Gly Trp Asn
210                 215                 220

Tyr Asp Ala Phe Met Asp Thr Asp Thr His Tyr Arg Ile Gln Gly Gly
225                 230                 235                 240

Thr Ile Gly Leu Ile Asn Ala Met Leu Thr Asp Ser Gly Ala Glu Val
            245                 250                 255

Arg Met Ser Val Pro Val Thr Ala Val Glu Gln Val Asn Gly Gly Val
            260                 265                 270

Lys Ile Lys Thr Asp Asp Glu Ile Ile Thr Ala Gly Val Val Val
275                 280                 285

Met Thr Val Pro Leu Asn Thr Tyr Lys His Ile Gly Phe Thr Pro Ala
290                 295                 300

Leu Ser Lys Gly Lys Gln Arg Phe Ile Lys Glu Gly Gln Leu Ser Lys
305                 310                 315                 320

Gly Ala Lys Leu Tyr Val His Val Lys Gln Asn Leu Gly Arg Val Phe
            325                 330                 335

Ala Phe Ala Asp Glu Gln Gln Pro Leu Asn Trp Val Gln Thr His Asp
            340                 345                 350

Tyr Ser Asp Glu Leu Gly Thr Ile Leu Ser Ile Thr Ile Ala Arg Lys
            355                 360                 365

Glu Thr Ile Asp Val Asn Asp Arg Asp Ala Val Thr Arg Glu Val Gln
370                 375                 380

Lys Met Phe Pro Gly Val Glu Val Leu Gly Thr Ala Ala Tyr Asp Trp
385                 390                 395                 400

Thr Ala Asp Pro Phe Ser Leu Gly Ala Trp Ala Ala Tyr Gly Val Gly
            405                 410                 415

Gln Leu Ser Arg Leu Lys Asp Leu Gln Ala Ala Glu Gly Arg Ile Leu
            420                 425                 430

Phe Ala Gly Ala Glu Thr Ser Asn Gly Trp His Ala Asn Ile Asp Gly
            435                 440                 445

Ala Val Glu Ser Gly Leu Arg Ala Gly Arg Glu Val Lys Gln Leu Leu
450                 455                 460

Ser
465                 470                 475                 480

<210> SEQ ID NO 21
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

```
Asp Ala Ala Ser Ala Thr Gln Lys Thr Asn Arg Ala Ser Thr Val Lys
             35                  40                  45

Gly Gly Phe Asp Tyr Asp Val Val Val Gly Gly Phe Ala Gly
 50                  55                  60

Ala Thr Ala Ala Arg Glu Cys Gly Leu Gln Gly Tyr Arg Thr Leu Leu
 65                  70                  75                  80

Leu Glu Ala Arg Ser Arg Leu Gly Gly Arg Thr Phe Thr Ser Arg Phe
                 85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
            115                 120                 125

Asp Pro Leu Thr Asn Leu Asp Lys Thr Leu Ile Met Tyr Asn Asp Gly
            130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
            195                 200                 205

Gln Ile Asn Ser Tyr Met Ala Leu Tyr Ala Gly Glu Thr Thr Asp Lys
            210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
            275                 280                 285

Lys Ile Lys Thr Asp Asp Glu Ile Ile Thr Ala Gly Val Val Val
            290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala His Ala Asp Glu Gln Gln Pro Leu Asn Trp Val Gln Thr His Asp
            355                 360                 365

Tyr Ser Asp Glu Leu Gly Thr Ile Leu Ser Ile Thr Ile Ala Arg Lys
            370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
            435                 440                 445

Phe Ala Gly Ala Glu Thr Ser Asn Gly Trp His Ala Asn Ile Asp Gly
```

-continued

```
                450           455           460
Ala Val Glu Ser Gly Leu Arg Ala Gly Arg Glu Val Lys Gln Leu Leu
465                 470                 475                 480

Ser

<210> SEQ ID NO 22
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
                35                  40                  45

Gly Gly Phe Asp Tyr Asp Val Val Val Gly Gly Phe Ala Gly
50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
                100                 105                 110

Pro His Val Trp Ala Glu Met Gln Arg Tyr Gly Leu Gly Val Val Glu
                115                 120                 125

Asp Pro Leu Thr Asn Leu Asp Lys Thr Leu Ile Met Tyr Asn Asp Gly
                130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
                180                 185                 190

Val Leu Asp Arg Ile Lys Thr Leu Gly Leu Ser Arg Leu Gln Gln Ala
                195                 200                 205

Gln Ile Asn Ser Tyr Met Ala Leu Tyr Ala Gly Glu Thr Thr Asp Lys
                210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
                260                 265                 270

Arg Met Ser Val Pro Val Thr Ala Val Glu Gln Val Asn Gly Gly Val
                275                 280                 285

Lys Ile Lys Thr Asp Asp Glu Ile Ile Thr Ala Gly Val Val Val
                290                 295                 300

Met Thr Val Pro Leu Asn Thr Tyr Lys His Ile Gly Phe Thr Pro Ala
305                 310                 315                 320
```

-continued

```
Leu Ser Lys Gly Lys Gln Arg Phe Ile Lys Glu Gly Gln Leu Ser Lys
            325                 330                 335

Gly Ala Lys Leu Tyr Val His Val Lys Gln Asn Leu Gly Arg Val Phe
        340                 345                 350

Ala Lys Ala Asp Glu Gln Gln Pro Leu Asn Trp Val Gln Thr His Asp
    355                 360                 365

Tyr Ser Asp Glu Leu Gly Thr Ile Leu Ser Ile Thr Ile Ala Arg Lys
370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
    450                 455                 460

Ala Val Glu Ser Gly Leu Arg Ala Gly Arg Glu Val Lys Gln Leu Leu
465                 470                 475                 480

Ser
```

<210> SEQ ID NO 23
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

```
Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190
```

-continued

```
Val Leu Asp Arg Ile Lys Thr Leu Gly Leu Ser Arg Leu Gln Gln Ala
            195                 200                 205

Gln Ile Asn Ser Tyr Met Ala Leu Tyr Ala Gly Glu Thr Thr Asp Lys
        210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
    290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Glu Ala Asp Glu Gln Gln Pro Leu Asn Trp Val Gln Thr His Asp
        355                 360                 365

Tyr Ser Asp Glu Leu Gly Thr Ile Leu Ser Ile Thr Ile Ala Arg Lys
370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
    450                 455                 460

Ala Val Glu Ser Gly Leu Arg Ala Gly Arg Glu Val Lys Gln Leu Leu
465                 470                 475                 480

Ser
```

<210> SEQ ID NO 24
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 24

```
Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Val Gly Gly Gly Phe Ala Gly
```

```
               50                  55                  60

Ala Thr Ala Ala Arg Glu Cys Gly Leu Gln Gly Tyr Arg Thr Leu Leu
 65                  70                  75                  80

Leu Glu Ala Arg Ser Arg Leu Gly Gly Arg Thr Phe Thr Ser Arg Phe
                     85                  90                  95

Ala Gly Gln Glu Ile Glu Phe Gly Ala Trp Val His Trp Leu Gln
                    100                 105                 110

Pro His Val Trp Ala Glu Met Gln Arg Tyr Gly Leu Gly Val Val Glu
                    115                 120                 125

Asp Pro Leu Thr Asn Leu Asp Lys Thr Leu Ile Met Tyr Asn Asp Gly
                    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                    165                 170                 175

His Glu Pro Met Phe Thr Glu Arg Ala Arg Glu Leu Asp Lys Ser Ser
                    180                 185                 190

Val Leu Asp Arg Ile Lys Thr Leu Gly Leu Ser Arg Leu Gln Gln Ala
                    195                 200                 205

Gln Ile Asn Ser Tyr Met Ala Leu Tyr Ala Gly Glu Thr Thr Asp Lys
                    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                    245                 250                 255

Thr Ile Gly Leu Ile Asn Ala Met Leu Thr Asp Ser Gly Ala Glu Val
                    260                 265                 270

Arg Met Ser Val Pro Val Thr Ala Val Glu Gln Val Asn Gly Gly Val
                    275                 280                 285

Lys Ile Lys Thr Asp Asp Asp Glu Ile Ile Thr Ala Gly Val Val Val
                    290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                    325                 330                 335

Gly Ala Lys Leu Tyr Val His Val Lys Gln Asn Leu Gly Arg Val Phe
                    340                 345                 350

Ala Phe Ala Asp Glu Gln Gln Pro Leu Asn Trp Val Gln Thr His Asp
                    355                 360                 365

Tyr Ser Asp Glu Leu Gly Thr Ile Leu Ser Ile Thr Ile Ala Arg Lys
                    370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                    405                 410                 415

Thr Ala Asp Pro Phe Ser Leu Gly Gln Trp Ala Ala Tyr Gly Val Gly
                    420                 425                 430

Gln Leu Ser Arg Leu Lys Asp Leu Gln Ala Ala Glu Gly Arg Ile Leu
                    435                 440                 445

Phe Ala Gly Ala Glu Thr Ser Asn Gly Trp His Ala Asn Ile Asp Gly
                    450                 455                 460

Ala Val Glu Ser Gly Leu Arg Ala Gly Arg Glu Val Lys Gln Leu Leu
465                 470                 475                 480
```

Ser

<210> SEQ ID NO 25
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

```
Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
    290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
```

```
                340             345             350
Ala Phe Ala Asp Glu Gln Pro Leu Asn Trp Val Gln Thr His Asp
        355                 360                 365

Tyr Ser Asp Glu Leu Gly Thr Ile Leu Ser Ile Thr Ile Ala Arg Lys
    370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Trp Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
    450                 455                 460

Ala Val Glu Ser Gly Leu Arg Ala Gly Arg Glu Val Lys Gln Leu Leu
465                 470                 475                 480

Ser
```

<210> SEQ ID NO 26
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

```
Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys
        35                  40                  45

Gly Gly Phe Asp Tyr Asp Val Val Val Gly Gly Gly Phe Ala Gly
    50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205
```

```
Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Phe Ala Asp Glu Gln Gln Pro Leu Asn Trp Val Gln Thr His Asp
        355                 360                 365

Tyr Ser Asp Glu Leu Gly Thr Ile Leu Ser Ile Thr Ile Ala Arg Lys
370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Pro Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
450                 455                 460

Ala Val Glu Ser Gly Leu Arg Ala Gly Arg Glu Val Lys Gln Leu Leu
465                 470                 475                 480

Ser

<210> SEQ ID NO 27
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
            35                  40                  45

Gly Gly Phe Asp Tyr Asp Val Val Val Gly Gly Phe Ala Gly
        50                  55                  60

Ala Thr Ala Ala Arg Glu Cys Gly Leu Gln Gly Tyr Arg Thr Leu Leu
65                  70                  75                  80
```

```
Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
            115                 120                 125

Asp Pro Leu Thr Asn Leu Asp Lys Thr Leu Ile Met Tyr Asn Asp Gly
130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
            195                 200                 205

Gln Ile Asn Ser Tyr Met Ala Leu Tyr Ala Gly Glu Thr Thr Asp Lys
            210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
            275                 280                 285

Lys Ile Lys Thr Asp Asp Asp Glu Ile Ile Thr Ala Gly Val Val Val
            290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Phe Ala Asp Glu Gln Gln Pro Leu Asn Trp Val Gln Thr His Asp
            355                 360                 365

Tyr Ser Asp Glu Leu Gly Thr Ile Leu Ser Ile Thr Ile Ala Arg Lys
            370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Cys Trp Ala Ala Tyr Gly Val Gly
            420                 425                 430

Gln Leu Ser Arg Leu Lys Asp Leu Gln Ala Ala Glu Gly Arg Ile Leu
            435                 440                 445

Phe Ala Gly Ala Glu Thr Ser Asn Gly Trp His Ala Asn Ile Asp Gly
450                 455                 460

Ala Val Glu Ser Gly Leu Arg Ala Gly Arg Glu Val Lys Gln Leu Leu
465                 470                 475                 480

Ser
```

```
<210> SEQ ID NO 28
<211> LENGTH: 432
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Gly Phe Asp Tyr Asp Val Val Val Gly Gly Phe Ala Gly Ala
1               5                   10                  15

Thr Ala Ala Arg Glu Cys Gly Leu Gln Gly Tyr Arg Thr Leu Leu Leu
                20                  25                  30

Glu Ala Arg Ser Arg Leu Gly Gly Arg Thr Phe Thr Ser Arg Phe Ala
            35                  40                  45

Gly Gln Glu Ile Glu Ile Gly Gly Arg Trp Val His Trp Leu Gln Pro
        50                  55                  60

His Val Trp Ala Glu Met Gln Arg Tyr Gly Leu Gly Val Val Glu Asp
65                  70                  75                  80

Pro Leu Thr Asn Leu Asp Lys Thr Leu Ile Met Tyr Asn Asp Gly Ser
                85                  90                  95

Val Glu Ser Ile Ser Pro Asp Glu Phe Gly Lys Asn Ile Arg Ile Ala
            100                 105                 110

Phe Glu Lys Leu Cys His Asp Ala Trp Glu Val Phe Pro Arg Pro His
        115                 120                 125

Glu Pro Met Phe Thr Glu Arg Ala Arg Glu Leu Asp Lys Ser Ser Val
130                 135                 140

Leu Asp Arg Ile Lys Thr Leu Gly Leu Ser Arg Leu Gln Gln Ala Gln
145                 150                 155                 160

Ile Asn Ser Tyr Met Ala Leu Tyr Ala Gly Glu Thr Thr Asp Lys Phe
                165                 170                 175

Gly Leu Pro Gly Val Leu Lys Leu Phe Ala Cys Gly Gly Trp Asn Tyr
            180                 185                 190

Asp Ala Phe Met Asp Thr Glu Thr His Tyr Arg Ile Gln Gly Gly Thr
        195                 200                 205

Ile Gly Leu Ile Asn Ala Met Leu Thr Asp Ser Gly Ala Glu Val Arg
210                 215                 220

Met Ser Val Pro Val Thr Ala Val Glu Gln Val Asn Gly Gly Val Lys
225                 230                 235                 240

Ile Lys Thr Asp Asp Asp Glu Ile Ile Thr Ala Gly Val Val Val Met
                245                 250                 255

Thr Val Pro Leu Asn Thr Tyr Lys His Ile Gly Phe Thr Pro Ala Leu
            260                 265                 270

Ser Lys Gly Lys Gln Arg Phe Ile Lys Glu Gly Gln Leu Ser Lys Gly
        275                 280                 285

Ala Lys Leu Tyr Val His Val Lys Gln Asn Leu Gly Arg Val Phe Ala
290                 295                 300

Phe Ala Asp Glu Gln Gln Pro Leu Asn Trp Val Gln Thr His Asp Tyr
305                 310                 315                 320

Ser Asp Glu Leu Gly Thr Ile Leu Ser Ile Thr Ile Ala Arg Lys Glu
                325                 330                 335

Thr Ile Asp Val Asn Asp Arg Asp Ala Val Thr Arg Glu Val Gln Lys
            340                 345                 350

Met Phe Pro Gly Val Glu Val Leu Gly Thr Ala Ala Tyr Asp Trp Thr
        355                 360                 365
```

```
Ala Asp Pro Phe Ser Leu Gly Ala Trp Ala Ala Tyr Gly Val Gly Gln
    370                 375                 380

Leu Ser Arg Leu Lys Asp Leu Gln Ala Ala Glu Gly Arg Ile Leu Phe
385                 390                 395                 400

Ala Gly Ala Glu Thr Ser Asn Gly Trp His Ala Asn Ile Asp Gly Ala
                405                 410                 415

Val Glu Ser Gly Leu Arg Ala Gly Arg Glu Val Lys Gln Leu Leu Ser
            420                 425                 430
```

```
<210> SEQ ID NO 29
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (28)..(29)
<223> OTHER INFORMATION: a, c, t, g, unknown or other

<400> SEQUENCE: 29
gcaggtcaag aaattgaatt tggtgscnnk tgggttcatt ggttacagc          49

<210> SEQ ID NO 30
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (28)..(29)
<223> OTHER INFORMATION: a, c, t, g, unknown or other

<400> SEQUENCE: 30
gcaggtcaag aaattgaacg tggtgscnnk tgggttcatt ggttacagc          49

<210> SEQ ID NO 31
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (28)..(29)
<223> OTHER INFORMATION: a, c, t, g, unknown or other

<400> SEQUENCE: 31
gcaggtcaag aaattgaaab cggtgscnnk tgggttcatt ggttacagc          49

<210> SEQ ID NO 32
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32
```

Gly Gly Gly Gly Ser Gly Ser Gly His His His His His His
1               5               10

<210> SEQ ID NO 33

<400> SEQUENCE: 33

000

<210> SEQ ID NO 34
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
            35                  40                  45

Gly Gly Phe Asp Tyr Asp Val Val Val Gly Gly Phe Ala Gly
        50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Arg Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
    130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
    210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
    290                 295                 300

```
Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
                340                 345                 350

Ala His Ala Asp Glu Gln Gln Pro Leu Asn Trp Val Gln Thr His Asp
                355                 360                 365

Tyr Ser Asp Glu Leu Gly Thr Ile Leu Ser Ile Thr Ile Ala Arg Lys
                370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
                420                 425                 430

Gln Leu Ser Arg Leu Lys Asp Leu Gln Ala Ala Glu Gly Arg Ile Leu
                435                 440                 445

Phe Ala Gly Ala Glu Thr Ser Asn Gly Trp His Ala Asn Ile Asp Gly
450                 455                 460

Ala Val Glu Ser Gly Leu Arg Ala Gly Arg Glu Val Lys Gln Leu Leu
465                 470                 475                 480

Ser

<210> SEQ ID NO 35
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
                35                  40                  45

Gly Gly Phe Asp Tyr Asp Val Val Val Gly Gly Gly Phe Ala Gly
50                  55                  60

Ala Thr Ala Ala Arg Glu Cys Gly Leu Gln Gly Tyr Arg Thr Leu Leu
65                  70                  75                  80

Leu Glu Ala Arg Ser Arg Leu Gly Gly Arg Thr Phe Thr Ser Arg Phe
                85                  90                  95

Ala Gly Gln Glu Ile Glu Ile Gly Gly Arg Trp Val His Trp Leu Gln
                100                 105                 110

Pro His Val Trp Ala Glu Met Gln Arg Tyr Gly Leu Gly Val Val Glu
                115                 120                 125

Asp Pro Leu Thr Asn Leu Asp Lys Thr Leu Ile Met Tyr Asn Asp Gly
                130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175
```

His Glu Pro Met Phe Thr Glu Arg Ala Arg Glu Leu Asp Lys Ser Ser
                180                 185                 190

Val Leu Asp Arg Ile Lys Thr Leu Gly Leu Ser Arg Leu Gln Gln Ala
            195                 200                 205

Gln Ile Asn Ser Tyr Met Ala Leu Tyr Ala Gly Glu Thr Thr Asp Lys
        210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Ile Thr Ala Gly Val Val Val
290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys
                325                 330                 335

Gly Ala Lys Leu Tyr Val His Val Lys Gln Asn Leu Gly Arg Val Phe
            340                 345                 350

Ala Phe Ala Asp Glu Gln Gln Pro Leu Asn Trp Val Gln Thr His Asp
        355                 360                 365

Tyr Ser Asp Glu Leu Gly Thr Ile Leu Ser Ile Thr Ile Ala Arg Lys
    370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Cys Trp Ala Ala Tyr Gly Val Gly
            420                 425                 430

Gln Leu Ser Arg Leu Lys Asp Leu Gln Ala Ala Glu Gly Arg Ile Leu
        435                 440                 445

Phe Ala Gly Ala Glu Thr Ser Asn Gly Trp His Ala Asn Ile Asp Gly
    450                 455                 460

Ala Val Glu Ser Gly Leu Arg Ala Gly Arg Glu Val Lys Gln Leu Leu
465                 470                 475                 480

Ser

<210> SEQ ID NO 36
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
            20                  25                  30

Asp Ala Ala Ser Ala Thr Gln Lys Thr Asn Arg Ala Ser Thr Val Lys

```
            35                  40                  45
Gly Gly Phe Asp Tyr Asp Val Val Val Gly Gly Phe Ala Gly
 50                  55                  60
Ala Thr Ala Ala Arg Glu Cys Gly Leu Gln Gly Tyr Arg Thr Leu Leu
 65                  70                  75                  80
Leu Glu Ala Arg Ser Arg Leu Gly Gly Arg Thr Phe Thr Ser Arg Phe
                 85                  90                  95
Ala Gly Gln Glu Ile Glu Phe Gly Gly Lys Trp Val His Trp Leu Gln
                100                 105                 110
Pro His Val Trp Ala Glu Met Gln Arg Tyr Gly Leu Gly Val Val Glu
                115                 120                 125
Asp Pro Leu Thr Asn Leu Asp Lys Thr Leu Ile Met Tyr Asn Asp Gly
            130                 135                 140
Ser Val Glu Ser Ile Ser Pro Asp Glu Phe Gly Lys Asn Ile Arg Ile
145                 150                 155                 160
Ala Phe Glu Lys Leu Cys His Asp Ala Trp Glu Val Phe Pro Arg Pro
                165                 170                 175
His Glu Pro Met Phe Thr Glu Arg Ala Arg Glu Leu Asp Lys Ser Ser
                180                 185                 190
Val Leu Asp Arg Ile Lys Thr Leu Gly Leu Ser Arg Leu Gln Gln Ala
                195                 200                 205
Gln Ile Asn Ser Tyr Met Ala Leu Tyr Ala Gly Glu Thr Thr Asp Lys
            210                 215                 220
Phe Gly Leu Pro Gly Val Leu Lys Leu Phe Ala Cys Gly Gly Trp Asn
225                 230                 235                 240
Tyr Asp Ala Phe Met Asp Thr Glu Thr His Tyr Arg Ile Gln Gly Gly
                245                 250                 255
Thr Ile Gly Leu Ile Asn Ala Met Leu Thr Asp Ser Gly Ala Glu Val
                260                 265                 270
Arg Met Ser Val Pro Val Thr Ala Val Glu Gln Val Asn Gly Gly Val
            275                 280                 285
Lys Ile Lys Thr Asp Asp Glu Ile Ile Thr Ala Gly Val Val Val
            290                 295                 300
Met Thr Val Pro Leu Asn Thr Tyr Lys His Ile Gly Phe Thr Pro Ala
305                 310                 315                 320
Leu Ser Lys Gly Lys Gln Arg Phe Ile Lys Glu Gly Gln Leu Ser Lys
                325                 330                 335
Gly Ala Lys Leu Tyr Val His Val Lys Gln Asn Leu Gly Arg Val Phe
                340                 345                 350
Ala Phe Ala Asp Glu Gln Gln Pro Leu Asn Trp Val Gln Thr His Asp
                355                 360                 365
Tyr Ser Asp Glu Leu Gly Thr Ile Leu Ser Ile Thr Ile Ala Arg Lys
            370                 375                 380
Glu Thr Ile Asp Val Asn Asp Arg Asp Ala Val Thr Arg Glu Val Gln
385                 390                 395                 400
Lys Met Phe Pro Gly Val Glu Val Leu Gly Thr Ala Ala Tyr Asp Trp
                405                 410                 415
Thr Ala Asp Pro Phe Ser Leu Gly Ala Trp Ala Ala Tyr Gly Val Gly
                420                 425                 430
Gln Leu Ser Arg Leu Lys Asp Leu Gln Ala Ala Glu Gly Arg Ile Leu
            435                 440                 445
Phe Ala Gly Ala Glu Thr Ser Asn Gly Trp His Ala Asn Ile Asp Gly
            450                 455                 460
```

Ala Val Glu Ser Gly Leu Arg Ala Gly Arg Glu Val Lys Gln Leu Leu
465                 470                 475                 480

Ser

<210> SEQ ID NO 37
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Ser Asp Lys Thr Lys Thr Asn Glu Gly Phe Ser Arg Arg Ser Phe Ile
1               5                   10                  15

Gly Ser Ala Ala Val Val Thr Ala Gly Val Ala Gly Leu Gly Ala Ile
                20                  25                  30

Asp Ala Ala Ser Ala Thr Gln Lys Thr Asn Arg Ala Ser Thr Val Lys
            35                  40                  45

Gly Gly Phe Asp Tyr Asp Val Val Val Gly Gly Phe Ala Gly
        50                  55                  60

Ala Thr Ala Ala Arg Glu Cys Gly Leu Gln Gly Tyr Arg Thr Leu Leu
65              70                  75                  80

Leu Glu Ala Arg Ser Arg Leu Gly Gly Arg Thr Phe Thr Ser Arg Phe
                85                  90                  95

Ala Gly Gln Glu Ile Glu Phe Gly Gly Ala Trp Val His Trp Leu Gln
            100                 105                 110

Pro His Val Trp Ala Glu Met Gln Arg Tyr Gly Leu Gly Val Val Glu
        115                 120                 125

Asp Pro Leu Thr Asn Leu Asp Lys Thr Leu Ile Met Tyr Asn Asp Gly
130                 135                 140

Ser Val Glu Ser Ile Ser Pro Asp Glu Phe Gly Lys Asn Ile Arg Ile
145                 150                 155                 160

Ala Phe Glu Lys Leu Cys His Asp Ala Trp Glu Val Phe Pro Arg Pro
                165                 170                 175

His Glu Pro Met Phe Thr Glu Arg Ala Arg Glu Leu Asp Lys Ser Ser
            180                 185                 190

Val Leu Asp Arg Ile Lys Thr Leu Gly Leu Ser Arg Leu Gln Gln Ala
        195                 200                 205

Gln Ile Asn Ser Tyr Met Ala Leu Tyr Ala Gly Glu Thr Thr Asp Lys
210                 215                 220

Phe Gly Leu Pro Gly Val Leu Lys Leu Phe Ala Cys Gly Gly Trp Asn
225                 230                 235                 240

Tyr Asp Ala Phe Met Asp Thr Glu Thr His Tyr Arg Ile Gln Gly Gly
                245                 250                 255

Thr Ile Gly Leu Ile Asn Ala Met Leu Thr Asp Ser Gly Ala Glu Val
            260                 265                 270

Arg Met Ser Val Pro Val Thr Ala Val Glu Gln Val Asn Gly Gly Val
        275                 280                 285

Lys Ile Lys Thr Asp Asp Glu Ile Thr Ala Gly Val Val Val
                290                 295                 300

Met Thr Val Pro Leu Asn Thr Tyr Lys His Ile Gly Phe Thr Pro Ala
305                 310                 315                 320

Leu Ser Lys Gly Lys Gln Arg Phe Ile Lys Glu Gly Gln Leu Ser Lys

-continued

```
                    325                 330                 335
Gly Ala Lys Leu Tyr Val His Val Lys Gln Asn Leu Gly Arg Val Phe
                340                 345                 350

Ala Cys Ala Asp Glu Gln Gln Pro Leu Asn Trp Val Gln Thr His Asp
                355                 360                 365

Tyr Ser Asp Glu Leu Gly Thr Ile Leu Ser Ile Thr Ile Ala Arg Lys
        370                 375                 380

Glu Thr Ile Asp Val Asn Asp Arg Asp Ala Val Thr Arg Glu Val Gln
385                 390                 395                 400

Lys Met Phe Pro Gly Val Glu Val Leu Gly Thr Ala Ala Tyr Asp Trp
                405                 410                 415

Thr Ala Asp Pro Phe Ser Leu Gly Ala Trp Ala Ala Tyr Gly Val Gly
                420                 425                 430

Gln Leu Ser Arg Leu Lys Asp Leu Gln Ala Ala Glu Gly Arg Ile Leu
                435                 440                 445

Phe Ala Gly Ala Glu Thr Ser Asn Gly Trp His Ala Asn Ile Asp Gly
        450                 455                 460

Ala Val Glu Ser Gly Leu Arg Ala Gly Arg Glu Val Lys Gln Leu Leu
465                 470                 475                 480

Ser

<210> SEQ ID NO 38
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 38

His His His His His His
1               5
```